United States Patent
Steinbüchel et al.

(10) Patent No.: US 6,524,831 B2
(45) Date of Patent: *Feb. 25, 2003

(54) SYNTHETIC ENZYMES FOR THE PRODUCTION OF CONIFERYL ALCOHOL, CONIFERYLALDEHYDE, FERULIC ACID, VANILLIN AND VANILLIC ACID AND THEIR USE

(75) Inventors: Alexander Steinbüchel, Altenberge (DE); Horst Priefert, Telgte (DE); Jürgen Rabenhorst, Höxter (DE)

(73) Assignee: Haarmann & Reimer GmbH, Holzminden (DE)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/976,063

(22) Filed: Nov. 21, 1997

(65) Prior Publication Data

US 2002/0182697 A1 Dec. 5, 2002

(30) Foreign Application Priority Data

Nov. 29, 1996 (DE) .......................... 196 49 655

(51) Int. Cl.⁷ .............................. C12N 9/02; C12P 7/22; C12Q 1/26; C07H 21/04
(52) U.S. Cl. .................... 435/156; 435/189; 435/25; 435/325; 435/320.1; 435/69.1; 435/252.3; 536/23.1; 536/23.2
(58) Field of Search .................. 435/189, 25, 156, 435/325, 320.1, 69.1; 536/23.1, 23.2

(56) References Cited

U.S. PATENT DOCUMENTS

| | | | |
|---|---|---|---|
| 4,847,422 A | 7/1989 | Klemola et al. | 568/438 |
| 5,017,388 A | 5/1991 | Rabenhorst et al. | 426/44 |
| 5,128,253 A | 7/1992 | Labuda et al. | 435/147 |
| 5,358,861 A | 10/1994 | Markus et al. | 435/147 |
| 5,510,252 A | 4/1996 | Hopp et al. | 435/146 |
| 5,712,132 A | 1/1998 | Mane et al. | 435/147 |

FOREIGN PATENT DOCUMENTS

| | | | |
|---|---|---|---|
| EP | 0 583 687 A2 | | 2/1984 |
| EP | 0 761 817 A2 | | 3/1997 |
| WO | WO 94/02621 | | 2/1994 |
| WO | WO 95/02062 | * | 1/1995 |
| WO | WO 97/35999 | | 10/1997 |

OTHER PUBLICATIONS

Fraaije, M. et al., Eur. J. Biochem., vol. 234, pp. 271–277, 1995.*

Lee, C. et al., Science, vol. 239, pp. 1288–1291, 1988.*

Studier, F. et al., Meth. Enzymol., vol. 185, pp. 60–89, 1990.*

Matthews, C. et al., Biochemistry, The Benjamin/Cummings Publishing Co., Inc., Redwood City, CA, Chapter 1, p. 13, 1990.*

Tadasa, Agric.Biol.Chem., 41 (6), 925–929 (1977): "Degradation of Eugenol by a Microorganism".

Tadasa et al., Agric.Biol.Chem., 47 (11), 2639–2640 (1983): "Initial Steps of Eugenol Degradation Pathway of a Microorganism".

Sutherland et al., Can.J.of Microbiology, 29, 1253–1257 (1983): "Metabolism of cinnamic, p–coumaric, , and ferulic acids by *Streptomyces setonii*".

Ötük, J.Ferment.Technol., vol. 63, No. 6, 501–506 (1985): "Degradation of Ferulic Acid by *Escherichia coli*".

Abraham et al., Bioflavour '87,399–413 (1987): "Microbial Transformations of Some Terpenoids and Natural Compounds".

Omori et al., Appl.Microbiol.Biotechnol, 29, 497–500 (1988): "Protocatechuic acid production from trans–ferulic acid . . . acid catabolism".

Rahouti et al., Applied and Environmental Microbiology, vol. 55, No. 9, 2391–2398 (1989): "Metabolism o Ferulic Acid by *Paecilomyces variotii* and *Pestalotia palmarum*".

English Abstract of JP 2195–871: 25.10.88–JP–267 284 (02.08.90) 09.03.89 as 055111 (1988).

English Abstract of JP 2200–192: 25.10.88–JP–267 285 (08.08.90) 09.03.89 as 055112 (1988).

English Abstract of JP 05227 980 (1992).

Labuda et al., Prog.Flavour Precursor Stud.Int.Conf. 477–482 (1992): "Microbial Bioconversion Process for the Production of Vanillin".

Rosazza et al., J.of Ind.Microbiology 15, 457–471 (1995): "Review: Biocatalytic transformations of ferulic acid: an abundant aromatic natural product".

Jaeger et al., Current Microbiology, vol. 6, 333–336 (1981): "Partial Purification and Characterization of a Conniferyl Alcohol Dehydrogenase from *Rhodococcus erythropolis*".

Lowry et al., J.Biol.Chem., 193, 265–275 (1951): "Protein Measurement with the Folin Phenol Reagent".

Stegemann et al., Z.Naturforsch, 28c, 722–732 (1973): "Potato Proteins: Genetic and Physiological Changes, Evaluated by One– and Two–dimensional PAA–Gel–techniques".

(List continued on next page.)

*Primary Examiner*—Rebecca E. Prouty
*Assistant Examiner*—Delia Ramirez
(74) *Attorney, Agent, or Firm*—Norris McLaughlin & Marcus

(57) ABSTRACT

The present invention relates to synthetic enzymes for the production of coniferyl alcohol, coniferylaldehyde, ferulic acid, vanillin and vanillic acid, the use thereof for the production of coniferyl alcohol, coniferylaldehyde, ferulic acid, vanillin and vanillic acid, DNA coding for these enzymes and microorganisms transformed with this DNA.

7 Claims, 1 Drawing Sheet

OTHER PUBLICATIONS

Laemmli, Nature, vol. 227, 680–685 (1970): "Cleavage of Structural Proteins during the Assembly of the Head of Bacteriophase T4".

Marmur, J.Mol.Biol. 3, 208–218 (1961): "A Procedure for the Isolation of Deoxyribonucleic Acid from Micro–organisms".

Nies et al., J.of Bacteriology, vol. 169, No. 10, 4865–4868 (1987): "Cloning of Plasmid Genes Encoding Resistance to Cadmium, Zinc, and Cobalt in *Alcaligenes eutrophus* CH34".

Hanahan, J.Mol.Biol. 166, 557–580 (1983): "Studies of Transformation of *Escherichia coli* with Plasmids".

Friedrich et al., J.of Bacteriology, vol. 147, No. 1, 198–205 (1981): "Naturally Occurring Genetic Transfer o Hydrogen–Oxidizing Ability Between Strains of *Alcaligenes eutrophus*".

Beaucage et al., Tetrahedron Letters, vol. 22, No. 20, 1859–1862 (1981): "Deoxynucleoside Phosphoramidites—A New Class of Key Intermediates for Deoxypolynucleotide Synthesis".

Sanger et al., Proc.Natl.Acad.Sci., vol. 74, No. 12, 5463–5467 (1977): "DNA sequencing with chain–terminating inhibitors".

Mizusawa et al., Nucleic Acids Research, vol. 14, No. 3, 1319–1325 (1986): "Improvement of the dideoxy chain termination method for DNA sequencing by use of deoxy–7–deazaguanosine triphosphate in place of dGTP".

Strauss et al., Analytical Biochemistry 154, 353–360 (1986): "Specific–Primer–Directed DNA Sequencing".

Rabenhorst, J., Appl. Microbiol. Biotechnol. (1996) 46, 470–474: "Production of methoxyphenol–type natural aroma chemicals by biotransformation of eugenol with a new *Pseudomonas* sp.".

English Abstract of EP 761817 (1997).

* cited by examiner

SEQUENCE LISTING

<160> NUMBER OF SEQ ID NOS: 45

<210> SEQ ID NO 1
<211> LENGTH: 32679
<212> TYPE: DNA
<213> ORGANISM: Pseudomonas sp.
<220> FEATURE:

<221> NAME/KEY: CDS
<222> LOCATION: (3146)..(3997)
<223> OTHER INFORMATION: gene = "ORF1"

<400> SEQUENCE: 1

```
gaattcatcc tcatggagca cttctacaag cagcaggcag gccaccctcc ccagaccgat      60
gacgtgcata ttatcgcgat cggcggaacg agctttaaac gctacctgga gctcggaaag     120
ctcctgaaca tcagagttgc cgcaattcga gataacgacg gtgactatca gcagaactgt     180
gtagcgaact acgaaggcta cctgtacgag tcggccaaga ttttcgccgc cccagatcct     240
gaccgaagca ccttcgaaat agggctgtac cgtgacaacc agaaagcctg tgacgatctc     300
tttgttgcgg gtcgcaaaaa actgaccgtg caagagtaca tgctcaaaaa taaagcggat     360
gccgctttcg agctgctgac caagaagtcc gctgaactga tcgccccgaa gtacatacag     420
gaagcgatcg aatggataag agcgtaattt tctccgtcgc aggatccggg aaaaccagcc     480
tgatcatcga gcgtctcagc cttgatcagc gggcattggt catcacttac acggacaaca     540
atcaccggca cctgcgcaac aggatcattc agagattcgg ggtgatccca tccaacatca     600
cgctcatgac gtacttctcg ttcctgcatg ggttctgcta tcggcccttg atgcaattgc     660
agctaggaac acgaggccta aatttcagac gtccgcccaa caggcagtac ccctgaacg      720
atctcaatcg gtatcgcgat ggaagcggca ggctctatca ctgccgcctc gcgaaactgc     780
tggacgttgc gcaggcctta ccggatgtgc gtgcccgcct ggagcgcttt tacgactgcc     840
tgtacgtcga cgaggtacag gatttcgcgg gtcacgactt caacctcctg ctggaggttt     900
cacgggcgaa gatcggcatg acgttcgtcg gtgatttcca ccagcacacc ttcgatacca     960
gccgagacgg agcggtaaac aaaacccttc acgacgatgc cgttcgctac gagaagcgct    1020
ttcgtgatgc cggcatttcg gtggacaagc aaacgttgaa ccgcagctgg cgatgcgcca    1080
aaacggtctg tgacttcatc agcgcaaagc tgaaaattgg cgatggacgc tcacgaggag    1140
cggggcagcc ggatcattag agttgatgac caagagcagg ccaacttgtt gcacgttgac    1200
ccaaccatcg tgaagctgtt tttgagcgaa cactacaagt acggctgcca ctccgaaaac    1260
tgggggggcaa gcaaggcatg gatcacttta cgatgtctg cgttgtgatg ggcccgggta     1320
tctggaaaga ctatgtggct gagaggttac accaggccaa cccgcaaacc cgaaacaagc    1380
tgtacgtggc ctgcactagg gcgcggggtg atctgtattt cgtgcctgag aagctcttga    1440
gggccttcaa acagggaaat taggcgataa agctgaaaaa ggattttcaa gtaaagacca    1500
ctccttcctt actcgatgtc cgcttttggc cgatttctgc cagtcacgac cggcaaagaa    1560
cggccaaaag cggactgatg cggttactaa gcctgcctct tattgaagct tggtgggctt    1620
taagaatgtg gtgcgatcca gcctgatgat gttccgcttt atgcacgcag ccaagcctat    1680
cgaccgccgt ctgcacgttg taaccgacta cgcctgtgcc tttgccgctg gtggccatgg    1740
agcgtgcatc cggatcggtg agtgagactt gcccatccgg tgcttcacgt agctgctgct    1800
ccatctcctt gagcgcctgc atctgctggc ggagtttctc gatttatcc tggaggcggc     1860
tggctttggc ttcggcgaca tcggattgag ttctgtcggc ggtgtccatc gctgccagat    1920
agcggtcgat gattttatca atctggtcca tccgggcgcg cacccgctat gatccggagt    1980
cctccgatat cgatgaggcc tatctgggct ggaagagcgg ttcggtgttc tcagaccttg    2040
gcgagaacgc ggtcaagctc agcttcgggc gccaagcctt caagatcggc aacggcttcc    2100
tgatcggcga aggccacgtc gaccaaggta acgatgcggc tactggctg gccctacct      2160
aggcgttcga caacaccgtc ctagcccaac tggacaccgg caagctgcat gtcgacctgt    2220
```

-continued

```
tcgacctcca ggcgggcatg gatctggacg tcgccgacat caaggagaaa gtccgggtgc    2280 gcggggcaa cgtcgagtgg cgcgacgaga cctacggcac ggtagggttc accggcttcc    2340
atacgctgga cgctgacaat ccgctgcgcg acggcatgaa tgtctacgac gtacgcgcat    2400
cgggcagccc gatccgagcc ctgccgcagg tggccctggc ggcggagtac gcctggcagc    2460
gcggcggcga ggcggacaag acgagtgagg cctggtacct acagggcagc tacacctttc    2520
gggatgcccc ctggacgcca gtgctgatgt accgtcacgc ggtcttctcc gacgactacg    2580
actccctgct gtacggctaa gggggcaaca acatgggctg gaaaggagca ttgcgttgaa    2640
acgatgctga agggcgtcac tcttttactg ctgtccgctc acgtcgaaac tgcatgattt    2700
cgggcagcct ttcttctatc cagtcggcca gcacctgaac atgagccgct acttcctggc    2760
caagcggcgt caggctgtac tcgacatgtg ggggaacgac cgggagcgaa tgtcgagcta    2820
tgaaaccgtc tccctccagg ccttgtaggg tctgcgcaag cattcttttc gctgacaccg    2880
ccgattcttc cgacgcaggt cgctgaatcg atggacaccg tccaccaaga tgatcagcac    2940
gagcacgccc agcggcttgt cacgtgcttg agcacgtccc gcgacggcat tcagcactca    3000
gcaattcccg cgccgtgctt gcatggagag actggtaagg gcggccagcg tgagtttcat    3060
ggcactaacc tttatgtatg tacttacttt tagttgctag tagggatatg gtgacgcctt    3120
catcctacga aacaagtgaa gactg atg atc gcc atc aca ggt gcc tcc gga    3172
                              Met Ile Ala Ile Thr Gly Ala Ser Gly
                                1               5 caa ctt ggt cgg ttg act ata gag gcg cta ctg aag cgc ctg cca gca    3220
Gln Leu Gly Arg Leu Thr Ile Glu Ala Leu Leu Lys Arg Leu Pro Ala
 10              15                  20                  25 tcc gaa att att gcc ctc gtc cgg gat ccg aat aag gcc gga gac ctt    3268
Ser Glu Ile Ile Ala Leu Val Arg Asp Pro Asn Lys Ala Gly Asp Leu
             30                  35                  40 acc gca cgt ggc atc gtg gtg cgc cag gcc gat tac aac cgg ccg gaa    3316
Thr Ala Arg Gly Ile Val Val Arg Gln Ala Asp Tyr Asn Arg Pro Glu
         45                  50                  55 aca ctc cac cgg gcc ctg att ggg gtc aac cgg ttg ctg ttg att tcc    3364
Thr Leu His Arg Ala Leu Ile Gly Val Asn Arg Leu Leu Leu Ile Ser
     60                  65                  70 tcc agt gag gtg ggt caa cga act gcg caa cac cgg gca gtg atc gac    3412
Ser Ser Glu Val Gly Gln Arg Thr Ala Gln His Arg Ala Val Ile Asp
 75                  80                  85 gct gcg aag caa gaa ggt atc gag ttg ctg gct tat acg agt ctg ctt    3460
Ala Ala Lys Gln Glu Gly Ile Glu Leu Leu Ala Tyr Thr Ser Leu Leu
 90                  95                 100                 105 cat gcc gat aaa tcg gcg ctg ggc cta gcg act gaa cac cga gac acg    3508
His Ala Asp Lys Ser Ala Leu Gly Leu Ala Thr Glu His Arg Asp Thr
            110                 115                 120 gaa cag gcc ctg aca gag tcc ggt att cct cat gtc ctg ttg cgc aac    3556
Glu Gln Ala Leu Thr Glu Ser Gly Ile Pro His Val Leu Leu Arg Asn
        125                 130                 135 ggt tgg tat cac gag aac tac acg gcg ggc atc cca gtc gcg ctg gtt    3604
Gly Trp Tyr His Glu Asn Tyr Thr Ala Gly Ile Pro Val Ala Leu Val
    140                 145                 150 cat ggc gtg ttg ctg ggc tgt gcc cag gat ggc ttg att gct tct gct    3652
His Gly Val Leu Leu Gly Cys Ala Gln Asp Gly Leu Ile Ala Ser Ala
155                 160                 165 gca cgt gct gac tac gcc gaa gca gcg gct gtg gtg ctc acc ggt gag    3700
Ala Arg Ala Asp Tyr Ala Glu Ala Ala Ala Val Val Leu Thr Gly Glu
170                 175                 180                 185
```

-continued

| | |
|---|---|
| aat cag gca ggt cgc gtc tac gag ctg gcc ggt gaa ccg gca tat acg<br>Asn Gln Ala Gly Arg Val Tyr Glu Leu Ala Gly Glu Pro Ala Tyr Thr<br>190                              195                              200 | 3748 |
| ctc acc gaa ctg gca gct gag gtg gcg ccg caa gca gga aag acc gtc<br>Leu Thr Glu Leu Ala Ala Glu Val Ala Pro Gln Ala Gly Lys Thr Val<br>205                              210                              215 | 3796 |
| gtg tat tcg aac cta tcc gag agc gat tac cga tct gcg ttg atc agt<br>Val Tyr Ser Asn Leu Ser Glu Ser Asp Tyr Arg Ser Ala Leu Ile Ser<br>220                              225                              230 | 3844 |
| gcg ggc ctt ccc gat ggt ttt gcg gca ttg ctc gca gac tct gat gca<br>Ala Gly Leu Pro Asp Gly Phe Ala Ala Leu Leu Ala Asp Ser Asp Ala<br>235                              240                              245 | 3892 |
| ggc gca gcc aag ggg tat ttg ttt gat tcc agt gga gac agt cgc aag<br>Gly Ala Ala Lys Gly Tyr Leu Phe Asp Ser Ser Gly Asp Ser Arg Lys<br>250                              255                              260                              265 | 3940 |
| ctg atc ggt cgc cca acc act ccg atg tcg gaa gcc atc gcg gca gca<br>Leu Ile Gly Arg Pro Thr Thr Pro Met Ser Glu Ala Ile Ala Ala Ala<br>270                              275                              280 | 3988 |
| att ggc cgc taaaactgca ttttcgcgac ttgagtgaca cctgggttag<br>Ile Gly Arg | 4037 |
| ataacccagg tgtctcgcac cgctttgggt tagtggtggg caatagcggt gtctggtcac | 4097 |
| cgcttgcccg gcggcgcgcc cgctattgga tgattctcaa cttcctggtg ccggcgtctt | 4157 |
| gttgggggccc aaacaggcgg gcataacgca atgtggcatt gcactgtcg cgcatgatgg | 4217 |
| cttctgctcg agcaccttgc ccgctaatca gcgcgtctac cacagcatga tgctgcatgt | 4277 |
| tggcaaaatt gaaccggcgg tactcttggg gaggttgcta ccgtcgacgg ccagtgaact | 4337 |
| gacagaggca aagggcaggt gttcattccg agccaatgct tcacctatgg cagcgttacc | 4397 |
| gctggcatcc acgatagctt gatggaagcg cttgttgatg tcgtggtatt cggcgaggtc | 4457 |
| gtcttcgctg acataacctt tctcaaatag ggcatcgccc tgggccaagc actgcaagag | 4517 |
| gatctcttgc gtttcactgg atagccctcg ctcggcagcc tgccttgcgg ccagtccttc | 4577 |
| aagtacccct cgaacctcca ccgcgcctgc aggtcatttt gggtcatttt gccgcactgc | 4637 |
| atagccacgt gcgccttggc gatcagtaac ccttcctgtt ctagcgctcg gaacgcaatg | 4697 |
| cggataggtg tgcgccgaca ctcccaggcg ctcggcagtg gggatttcgg cgatgcgctc | 4757 |
| tcctgccggg agttcgccat ccacaatcat tttgcgcagt agattgagta ctcgctgccc | 4817 |
| gggcccgctc atttcagcct ccgattggat ccagtaatgg tttgagagaa ttttactcgc | 4877 |
| aagggatttc tgggcaatag ccccgctgat tgctggtttt tgtatgtggc gtgcgactat | 4937 |
| cgcacagaat tggatccacc ttggcgcaaa aaaactggag ctacctcatc ggtcgtggtt | 4997 |
| atattggatc ccataaggtc aagttcatag ctgattttgg ctttagatgt ccattgtgga | 5057 |
| tccaaaaaca agatcgccat tgaggaacgc gccatgtttc gaaaaacgc ctggtatgtc | 5117 |
| gcttgcactc cggatgaaat cgcagataag ccgctaggcc gtcagatctg caacgaaaag | 5177 |
| attgtcttct atcgggggcc ggaaggacgt gttgccgcgg tagaggattt ctgccctcat | 5237 |
| cgcggggcac cgttgtccct gggtttcgtt cgcgacggta agctgatttg cggctaccac | 5297 |
| ggtttggaaa tgggctgcga gggcaaaacg ctcgcgatgc ccgggcagcg cgttcaaggc | 5357 |
| ttcccttgca tcaaaagcta cgcggtagaa gagcgatacg gctttatctg ggtatggcct | 5417 |
| ggtgatcgcg agctggcgga tccggcgctt attcaccacc tggagtgggc cgataatccg | 5477 |
| gagtgggcct atggtggcgg tctctaccac atcgcttgtg attaccgcct gatgatcgac | 5537 |
| aacctcatgg atctcacccca tgagacctat gtgcatgcct ccagcatcgg tcaaaaggaa | 5597 |

-continued

```
attgacgagg caccggtcag tactcgtgtc gagggcgaca ccgtgattac cagccggtac      5657
atggataacg tcatggcccc tccgttctgg cgtgctgcgc ttcgtggcaa cggcttggcc      5717
gacgatgtac cggttgatcg ctggcagatc tgccgattcg ctcctccgag tcacgtactg      5777
atcgaagtag gtgtggctca tgcgggcaaa ggcggatatg acgcgccggc ggaatacaag      5837
gccggcagca tagtggtcga cttcatcacg ccggagagtg atacctcgat ttggtacttc      5897 tgggcatgg ctcgcaactt ccgtccgcag ggcacggagc tgactgaaac cattcgtgtt       5957
ggtcagggca agatttttgc cgaggacctg gacatgctgg agcagcagca gcgcaatctg      6017
ctggcctacc cggagcgcca gttgctcaag ctgaatatcg atgccggcgg ggttcagtca      6077
cggcgcgtca ttgatcggat tctcgcagct gaacaagagg ccgcagacgc agcgctgatc      6137
gcgagaagtg catcatgatt gaggtaatca tttcggcgat gcgcttggtt gctcaggaca      6197
tcattagcct tgagtttgtc cgggctgacg gtggcttgct tccgcctgtc gaggccggcg      6257
cccacgtcga tgtgcatctt cctggcggcc tgattcggca gtactcgctc tggaatcaac      6317
caggggcgca gagccattac tgcatcggtg ttctgaagga cccggcgtct cgtggtggtt      6377
cgaaggcggt gcacgagaat cttcgcgtcg ggatgcgcgt gcaaattagc gagccgagga      6437
acctattccc attggaagag ggggtggagc ggagtctgct gttcgcgggc gggattggca      6497
ttacgccgat tctgtgtatg gctcaagaat tagcagcacg cgagcaagat ttcgagttgc      6557
attattgcgc gcgttcgacc gaccgagcgg cgttcgttga atggcttaag gttttgcgact     6617 ttgctgatca cgtacgtttc cactttgaca atggcccgga tcagcaaaaa ctgaatgccg      6677
cagcgctgct agcggccgag gccgaaggta cccaccttta tgtctgtggg cccggcgggt      6737 tcatgggca tgtgcttgat accgcgaagg agcagggctg ggctgacaat cgactgcatc       6797
gagagtattt cgccgcggcg ccgaatgtga gtgctgacga tggcagtttc gaggtgcgga      6857
ttcacagcac cggacaagtg cttcaggtcc cgcggatca aacggtctcc caggtgctcg       6917
atgcggccgg aattatcgtt cccgtttctt gtgagcaggg catctgcggt acttgcatca      6977
ctcgggtggt agacgagag cctgatcatc gtgacttctt cctcacggat gcggagaagg       7037
caaagaacga ccagttcacc ccctgttgct cgcgagccaa gagcgcctgt ttggtcttgg      7097
atctctaact catcccgtg tccggtcccc tgctttggtg cggcggactg tgcgcgggta       7157
agtaaacagg ctcaaccgtt tttagcggga taaccattct tgaggatgaa ggagggttat      7217
cccgctcttt tcatgcacca agccattcat agtcaccagc tgcttctacg tgctgctgcg      7277
ttacaagttt attcagaagg aaatcggaat gatcaaatcc cgcgccgctg tggcgttcgc      7337
acccaatcag ccattgcaga tcgtcgaagt ggacgtggct ccgcccaagg ccggtgaagt      7397
cctggtgcgg gtcgtggcca ccggcgtttg ccacaccgat gcctacaccc tgtccggcgc      7457
tgattccgag ggcgttttcc cctgcatcct tggtcacgaa gcggcggca ttgtcgaagc       7517 ggtgggcgag ggcgtcacct cgctggcggt cggcgaccac gtgatcccgc tctacacggc      7577
cgaatgccgt gagtgcaagt tcttcaagtc cggcaagacc aacctgtgcc agaaagtgcg      7637
tgctactcag ggcaagggtc tgatgccgga cggcacctcc cgcttcagct acaacggtca      7697
gccgatctac cactacatgg gctgctcgac cttctccgag tacaccgtgc tgccggaaat      7757
ctccctggcg aagattccca agaatgcgcc gctggagaaa gtctgcctgc tgggctgcgg      7817
cgtgaccacc ggcattggcg cggtgctgaa cactgccaag gtggaggagg gtgctaccgt      7877
ggccatcttc ggcctgggcg gcatcggctt ggcggcgatc atcggcgcga agatggccaa      7937
ggcctcgcgc atcatcgcca tcgacatcaa tccgtccaag ttcgatgtgg ctcgcgagct      7997
```

-continued

```
gggcgccact gacttcgtca atccgaacga tcacgcgaag ccgatccagg atgtcatcgt      8057
cgagatgact gatggcggtg tggactacag cttcgagtgc atcggcaacg ttcgactcat      8117
gcgcgcagca ctcgagtgct gccacaaggg ctggggcgaa tccgtgatca tcggcgtggc      8177
gccggcgggg gccgaaatca acacccgtcc gttccacctg gtgaccggtc gcgtctggcg      8237
gggttcggcg ttcggtggcg taaagggccg caccgaactc ccgagctacg tggagaaggc      8297
acagcagggc gagatcccgc tggacacctt catcactcac accatgggcc tggacgacat      8357
caacacggcc ttcgacctga tggacgaagg gaagagcatc cgctctgttg ttcaattgag      8417
tcgctagtga agtggggtga ggaaattgga ttaggaggcg atggttcct gccgcttaac       8477 caccttgtcc cagcttctgg ctgagatttc caagattcgg tgaaatttgc catgccgcaa      8537
actcttgctg gacggttgag tctgttatcc ggcaccgacg aattaaccct gcttcttcgg      8597
ggtggtcggg gcattgagcg tgaagccttg cgggtcgatg ttcaaggtga actggcgctg      8657
acgcctcacc cggcggcgct tggctctgcg ttgacccatc cgacaattac tacggattac      8717
gccgaggccc tgcttgagtt gatcactcgg ccggcaaccg attgtgcgca agccttggct      8777
gagctggagg agcttcaccg tttcgttcat tcgagacttg aggggagta tctctggaat       8837 ctgtccatgc ctggcagatt gccggttgat gagcaaatcc cgattgcttg gtatggacca      8897
tcaaatccag gcatgttgcg ccacgtttat cgccgtggcc tagctctgcg ttatggcaag      8957
cgaatgcaat gcatcgcagg gattcactac aactactcac tgccgccaga cttttcgct      9017 gtcctgacca aggcagaggt cgggtctccc aagttactgg agcgccagtc agcagcttac      9077
atgcgccaaa ttcgcaacct tcggcaatac ggttggttgc tggcctactt gttcggcgct      9137
tcccccgcca tctgcaagag cttcttgggg ggcgagagag atgagctagc tcgcatgggg     9197
ggcgatacgc tttacatgcc ctatgcaacc agcttgcgca tgagtgacat cgggtaccgc     9257
aaccgtgcca tggatgatct atctcccagc ctgaatgatc tgggtgccta tattcgcgat     9317
atttgccgtg ctcttcacac tcccgatgcc cagtaccagg cgctgggtgt gtttgcacag     9377
ggcgagtggc ggcagttaaa cgccaatcta ttgcagttgg atagtgagta ctacgcactg     9437
gcgcgaccga agtcagcgcc cgagcggggg gagcgaaacc tggatgctct cgctaggcgt     9497
ggagtccagt atgtggagct cgcgcactg gatctcgatc cattctcccc gttaggcatt     9557
ggcctgacct cgcgccaagtt cctcgatggc ttttttgcttt tctgcttgtt gtctgaggcg    9617
ccggttgatg atcgaaatgc ccagcgttca agaccgggaa atctgagcc tggccggcaa     9677 gtacgggcgt cacctggctt aaagctgcat cggaatggtc agtccattct cctcaaggat     9737
tgggcgcagg aagtgttgac ggaggttcag gcctgtgtgg aattgctcga cagtgcaaat    9797
gggggctcat ctcacgcatt ggcttggtca gcacaggagg aaaaggtgct taatccggat    9857
tgtgcgccat cagctcaggt gctcgcagag atacacagac acgtgggag cttcacggca     9917 tttggtcgcc aattagctat cgaccatgca aaacacttca gtgcctcctc gcttgaggct     9977
ggcgtagcca aagcgcttga cctccaggcg acgtcgtctc tgcgcgagca gcatcaattg    10037
gaggccaacg accgtgcgcc attttctgac taccttcagc aattctccct ggctttcggt    10097
caatccgtcg gcgcctctcg tgcgcccaac cctaccgcgc acctcatcga tctgacccct    10157
cctgtctaag gttgtcgtgg gagcagatcc gtgggccgag cttcctccag ggcctggccg    10217
cagcgatcca gttgctaggt ccctatgctc ttgcataggg taaaaattag ttattgtgtt    10277
taacgaaacg tctggcatac tggctttagg cacgagcttc cacgccgaag ttgagagcgt    10337
```

-continued

```
catgaacgat ttttcgtgtg gagagacgat gcccgatgcg gtcgacgagg ttcaggtcct    10397
aatggcagtg ccggcggcta acggaacgt gccgtatttt gaggcttgga gcgtggtgaa     10457
gcagcttggc tgctccctgg gcctgtcagg atcacgctgt gtcggcagtg acacttcaaa    10517
acaagaaggg cattaagatg atgaatgtta attataaggc tgtcggggcg agcctactcc    10577
tcgccttcat ctctcaggga gcttgggcag agagccccgc agcctctggc aatacccctg    10637
acatttatcg aaagacctgc acctactgcc atgagcctac tgtcaacaat ggccgggtca    10697
ttgcccgaag cctcgggccg actctgcgag gcgccagat ccctccacag tacacggagt     10757
acatggtgcg tcatggacgc ggggcaatgc ctgcattctc tgaagcagaa gtgcctccgg    10817
cggagctgaa agttctgggc gattggattc agcaaagcag tgctcccaaa gacgctggag    10877
tcgcgccatg actacccgtc gcaactttct aataggcgcg tcgcaggtgg gggcattggt    10937
gatgatgtcg ccgaaattgg tcttccgtac gccgctcaag cagaagcccg tgcgcatcct    10997
gtcgaccggg ctggccggtg agcaagagtt tcactcgatg cttcgcgcgc gattgaccca    11057
tacgggtcag gtcgacatcg cgtcggtacc gctggacgca gctatttggg cttctcccgc    11117
tcgacttgcc caggcaatgg atgcgttgaa tggtacgcgt ctgatcgctt ttgttgagcc    11177
caggaacgaa ttgatactga tgcaattctt gatggatcgc ggggctgcgg tgcttattca    11237
aggtgagcat gcggtggaca gcaagggggt ctctcggcac gactttctga gtaccccatc    11297
cagtgcggga attggagggg cgctagccga cagcctggca aaaggggggct cgccgttctc    11357
tatttccgtc cgagcgcttg gctcggtaac tgctcagcca agaagtaatc agagtgaggt    11417
ggccacccac tggacgaccg ctctggggac ctattatgcc gatatcgcag tggggcgctg    11477
ggagccgcag cgcgaagtgg ccagctatgg aagtggacta atcatggcgg aacggcttga    11537
tcgtgttgcc tcaaccttca ttgcagatct ctgagtcagg gtattgatat ggaaagcacc    11597
gtagttcttc ccgagggtgt caccccggag cagttcacca aagccatcag cgagttccgt    11657
caggtattgg gtgaggacag tgttcttgtc actgctgaac gagttgttcc ctatacgaaa    11717
ctcctcattc ctacacagga tgatgcccag tacacccgg ccgtgccttt gactccttct     11777
tcggtggagc aggtccagaa agtcatgggg atctgcaata agtacaagat cccggtatgg    11837
ccaatctcta ccgtcggaa ctgggggtat gggtccgctt cgcctgcaac tcctgggcag     11897
atgattcttg accttcgcaa gatgaacaag atcattgaga tcgatgttga ggggtgtact    11957
gccctgctcg agccgggcgt tacctaccag cagcttcacg attacatcaa ggagcacaat    12017
ctgcccttga tgctggatgt gccgactatt gggcctatgg ttggcccggt gggtaacacg    12077
ctggatcgag gcgttggtta tacgccgtac ggcgagcact tcatgatgca gtgtggtatg    12137
gaagtcgtca tggccgatgg cgaaatcctc cgtactggta tgggctcggt gcccaaagcc    12197
aagacttggc aggcattcaa atggggctat ggtccatatc tggacggtat ctttacccag    12257
tccaactttg gtgttgtgac aaagctcggg atttggttga tgcccaagcc gccagtgatc    12317
aagtcgttta tgatccgtta tcccaatgaa gctgatgtgg ttaaggcaat tgatgctttt    12377
cgcccgctgc gtattactca gctgattcct aacgtcgttt tgttcatgca cggcatgtac    12437
gaaacggcaa tctgccggac gcgtgctgag gttacttcgg acccaggtcc tatttctgaa    12497
gcggacgccc gcaaagcatt caaagagcta ggcgttggct actggaacgt ttacttcgcg    12557
ctttacggca cagaagagca gatagccgtc aatgaaaaga tcgtccgcgg catcctcgaa    12617
ccgacggggg gtgagatcct caccgaagag gaggctgagg ataacattct tttccatcac    12677
cataagcagc tcatgaacgg cgagatgaca ttggaggaaa tgaatatcta ccagtggcgc    12737
```

```
ggagcaggtg gcggtgcttg ctggtttgca ccggttgctc aggtcaaggg gcatgaggca    12797
gagcagcagg tcaagcttgc tcagaaggtg cttgcaaagc atgggttcga ttacacggcg    12857
ggctttgcga ttggttggcg cgatcttcac catgtgatcg atgtgctgta cgaccgtagc    12917
aatgccgacg agaaaaagcg cgcttacgct tgctttgatg aattgatcga cgtctttgcg    12977
gccgaaggct tgcaagttac aggaccaat attgccttta tggacaaagt cgcctctaag     13037
ttcggcgctg agaataagag ggtcaatcag aagatcaagg ctgcccttga tccaaacggc    13097
atcatcgctc ccggcaagtc gggcattcat cttcccaaat aatgcgtgtt cgtgaggcgg    13157
ctgctagccg cctcatttga agaaagagtc gtatcggcga tgcatgatgc gtcgttcgct    13217
ctcggctgtt gattcttcga aagaagcgta tggggggga atgattgcaa tcactgcggg     13277
caccggaagt cttggtcggg ctatcgttga gcgactaggg gactgcggtc ttatcggtca    13337
agttcgattg acgctcgcg atcctaaaag gcttcgtgcc gctgccgagg aagggtttca     13397
ggtcgctaag gcggattacg ccgatattgg gagtcttgac caggcattac aggggtaga    13457 cgtattactc ctgatttctg gtactgcacc caatgaaata aggatccaac agcataagtc    13517
ggtcatcgac gcggcaaaac gaaacggcgt gtcgcgtatt gtgtatacca gcttcataaa    13577
tccaagtact cgcagcaggt ctatttgggc ctccattcat cgtgaaactg agacttacct    13637
caggcagtct ggggtgaagt ttacgattgt ccgaaataat cagtatgcgt ctaacctgga    13697
tctgttgctg ctgagggctc aagacagcgg aatatttgcc attcccgggg cgaaggggcg    13757
ggtggcgtac gtctctcatc gcgacgttgc cgctgccatc tgtagtgtcc tgacgaccgc    13817
cggacacgat aacaggatct accagctcac aggctctgag gctctcaatg ggctcgagat    13877
cgcggagatt cttggtgggg tgctcgggcg tccagtgcgc gcgatggatg cctcgcctga    13937
cgagtttgct gccagcttc gcgaggctgg attccctgag tttatggttg aaggcctact      13997
aagcatttat gccgcttcag gtgctgggga gtaccaatcc gtcagtcctg atgttgggtt    14057
gttgacggga cgacgtgccg aatcgatgcg aacttacata cagcgtctag tttggccttg    14117
agggaggtga ccgacgtatg aaggcttatg agcttcacaa gatttcggaa caggtagagg    14177
tcaggctcca gccaactcgg ccccgcccgc agttgaatca tggcgaggtc ctcatcaggg    14237
tccatgcagc ctcgctcaac tttcgcgatt tgatgatctt ggccggtcgc tatccgggtc    14297 aaaatgaaacc cgatgtgatc ccgctgtccg atggtgctgg cgagattgtg gaggtcgggc    14357
ctggcgtatc ttcggaggtg cagggtcagc gcgtagccag caccttttc cctaactggc     14417 gggccgaaaa gattaccgag ccggctattg aggtgtcgtt gggcttcggt atggacggga    14477
tgctcgcgga atacgttgct ctgccctatg aggcaacgat accgataccg gagcacctgt    14537
cgtacgagga ggctgcaaca ttgccttgcg cggcgctaac cgcttggaat gcgttgaccg    14597
aagtggggcg tgtcaaggcc ggtgatacgg tcttgttgct tggcactggc ggtgtctcga    14657
tgttcgcgtt gcagttcgcc aagctcttgg gggcgacggt cattcacacc tcgagcagtg    14717
aacaaaagct ggagagggtg aaagcgatgg gggctgatca tctgatcaac taccgcaatt    14777
cgccagggtg ggaccgtact gtcctggatc tcaccgcggg gcgagggggtt gacctggtag    14837 tcgaggtagg ggggcgggg accttggagc gctcacttcg tgcggtcaag gtaggcgta     14897 ttgtcgccac gattgggcta gtggctggcg ttggcccgat tgacccattg ccgcttatct    14957
ccagggctat tcagctctcg ggcgtctatg tcggttcccg ggaaatgttt ctctcaatga    15017
acaaagccat tgcatcagcc gaaatcaagc cagtgatcga ttgctgcttc cccatcgacg    15077
```

-continued

```
aggttggaga tgcttatgag tacatgcgta gcggcaatca ccttggcaaa gtagttatca    15137
cgatctaact gccgctaaac ccgttgtgcg gcaatttgcg ggagctagta ccgggctttc    15197
ggtttggctc ttggatggtc ttcgcatgca cgctttacga aggggggccag ggacagacgc   15257
cccgggggcgt aatcaatggc cttgcgtgca ggctctcacc gtcgtgatcg ggattggaaa   15317
ttcgtgcgag gacagcggcc acgtaccggc gccctgaagg gctggaaggt tggagtttcg    15377
ttaaggtctg gtacccagca gccatggaga gcggcccta gccggaatgg cagcttgatg     15437
gttgccacgg gaccagactg gatgtcttga gtgtcgagaa ttaccagatc gctgcgattt    15497
tcatcgaggc gaccaaccac ggtcagcaag tacccgtcac cttcggcggc ggtcggactt    15557
ctagggacga aggccggctc ctgggccgcc gaggcttcgc cggagtacca gaggtcgtag    15617
tcacctcggt ggttgtccca gatgccgagt gagttgtacg cgaatatctt ctcggcctgc    15677
tgatgcgcaa gtggtttgcg tggatcgtcc accccataa agccatagcg gttgcattgc     15737
agggcgaacg aagaatccat gattggcatt tccgcaaaga aatcgtgtag ccgggttcgc    15797
ttgatctcgt cgctgctgct atcgaggtca atttcccaac gagtcaggcg tggtacggct    15857
ttctcagggg cgaagggttg gttttgtgag ttggggaagg ggaacggcag gatttcactt    15917
tccataaggt cgatataaat cttggttccg acttcccaag cattcacaac atgaaatacc    15977
cagagcgccg gtgccttgag ccagcgaatc agactgccct ggcgcggcgc gagtacgcca    16037
atgtagctgc ccagttccgg ctcccacata taaattggct gtttcgcctt gaggcgggac    16097
aggctgttgg tggccggcat aattgggaaa atggaccaat ttcgggtaat ggcaaagtcg    16157
tgcatgaatg cgccataggg ctgctcaaac caagtttcat gtgtcacctt gccgtgcttg    16217
tcgacaatgt aataggccat gtctggagtt gcttcgccct tagctgccga accgaagaac    16277
aacaagtcac ccgtttccgg gtcatatttt ggatgggcgg tgtgggtttg gctggtaact    16337
tggccgtcgt agtcgaagtg tccgcgagtt tcaagtgtac gaggatccag ttcgtacggt    16397
aggccgtctt ccttcaccgc cagcaccttg ccgtgatggc taatgatgct tgtattggca    16457
acggtgcggt ctagtccttt tacactggtg tcgtcggtat aggggtttct gtacatgcca    16517
aatagcgatt ttcgcgctag tcgttcggcc gtgaatcgag cggttttaac ccagcgactg    16577
atgaagtcga catgaccatc ttcgaagtgg aaggcagagg ccattccatc tccatctatg    16637
aaggtgtgga attttttgtgg ggtaacttga ggctctggcg tattacggta gaacgttcca    16697
tttattgatt ttgggatttc gccgtcaacc tctagatcga acaagtctgc ctctatacgg    16757
gtggggagaa gtgttcctac taattgcggg tcgttgcggt tgaatctcgc catggcacgg    16817
tctcctttgt tgttctgaat ggcctaaatg cgcggcttgc cggggttggag tttatgttta   16877
ggactgaccg gatttcatgt gtgccggtga agtgaagatg tctgtgagtg caatggtggt    16937
ggtattgaaa atgggccgag gctggcctat tgtttagaat ttcaagaatg acaactattc    16997
ggtggcggcg tatgtccatt cactctgagg ggatcactct cgcggattcg ccgctgcatt    17057
gggcgcatac cctgaatgga tcaatgcgta ctcatttcga agtccagcgt cttgagcggg    17117
gtagaggtgc ctcccttgcc cgatctagat ttggcgcggg tgagctgtac agtgccattg    17177
caccaagcca ggtacttcgc cacttcaacg accagcgaaa tgctgatgag gctgagcaca    17237
gctatttgat tcagatacga agtggcgctt tgggcgttgc atccggcgga agaaaggtga    17297
tcttggcaaa tggtgattgc tccatagttg atagtcgcca agacttcaca ctttcctcga    17357
actcttcgac ccaaggtgtc gtaatacgct ttccggtgag ttggctggga gcgtgggtgt    17417
ccaatccgga ggatcttatc gcccgacgag ttgatgctga ggtagggtgg ggtagggcgc    17477
```

```
taagcgcatc ggtttctaat ctagatccat tgcgcatcga cgatttaggt agcaatgtaa    17537
atggcattgc agagcatgtt gctatgttaa tttcactagc aagttctgcg gttagttctg    17597
aagatggggg tgtggctctt cggaaaatga gggaagtgaa gagagtactc gagcagagtt    17657
tcgcagacgc taatctcggg ccggaaagtg tttcaagtca attaggaatt tcgaaacgct    17717
atttgcatta tgtctttgct gcgtgcggta cgacctttgg tcgcgagctg ttggaaatac    17777
gcctgggcaa agcttatcga atgctctgtg cggcgagtga ctcgggtgct gtgctgaagg    17837
tggccatgtc ctcaggtttt tcggattcaa gccatttcag caagaaattt aaggaaagat    17897
acggtgtttc gcctgtctcc ttggtgaggc aggcttgatt tcccatagcg ttattgcggt    17957
cgtcgttgca aatgcggacc tgcgtgatca tcaaggctaa gactgccaca ttaggtgtcg    18017
actcgagcgt ccctctatcc gcctgaccgc gctccgtccc tagtacctag gaaattgagt    18077
gggcctactt gccagggcca gttggattcg gtgctggtga gcgctgcggg tgacagaatc    18137
ctgatcgtgg cgatcacgat ggcgataaag ttgcccggtg tcgtagatcg cagggtgacc    18197
aagacgggga ctcatggcgc ggatcccgcc agtgatgcct tcgcatgacg ccacctctct    18257
cctccgctca gccttcatgc ctgactaatt aagtcgtata tcaatctggc tctgtgccgc    18317
attcagttcc tccagctgca ttgtctctcg gcgggagggc attccctgc attggccaaa     18377
tgggtcccct tgttcacgac cggacaagcg caccgtgctg cccgttcgtc gtgtgccctg    18437
tcaaaaagcc tggcgacgaa agggcggcag gccgcatggc cacggctggg cggtaactga    18497
tgcttgcgtt aatcgttaac cgtttgaaat tccttgccaa atttcggcga gagaatcatg    18557
cgggtacgcc tttccgtgcg ctttgatctg cgcttccgtg ccttgaatca gaaaaatagt    18617
taattgacag aactataggt tcgcagtagc ttttgctcac ccaccaaatc cacagcactg    18677
gggtgcacga tgaatagcta cgatggccgt tggtctaccg ttgatgtgaa ggttgaagaa    18737
ggtatcgctt gggtcacgct gaaccgcccg gagaagcgca acgcaatgag cccaactctc    18797
aatcgagaga tggtcgaggt tctggaggtg ctggagcagg acgcagatgc tcgcgtgctt    18857
gttctgactg gtgcaggcga atcctggacc gcgggcatgg acctgaagga gtatttccgc    18917
gagaccgatg ctggccccga aattctgcaa gagaagattc gtcgcgaagc gtcgacctgg    18977
cagtggaagc tcctgcggat gtacaccaag ccgaccatcg cgatggtcaa tggctggtgc    19037
ttcggcggcg gcttcagccc gctggtggcc tgtgatctgg ccatctgtgc cgacgaggcc    19097
accttggcc tgtccgagat caactggggc atcccgccgg gcaacctggt gagtaaggct    19157
atggccgaca ccgtgggtca ccgcgagtcc ctttactaca tcatgactgg caagacattt    19217
ggcggtcagc aggccgccaa gatggggctt gtgaaccaga gtgttccgct ggccgagctg    19277
cgcagtgtca ctgtagagct ggctcagaac ctgctggaca agaacccgt agtgctgcgt     19337
gccgccaaaa taggcttcaa gcgttgccgc gagctgactt gggagcagaa cgaggactac    19397
ctgtacgcca agctcgacca atcccgtttg ctcgatccgg aaggcggtcg cgagcagggc    19457
atgaagcagt tccttgacga gaaaagcatc aagccgggct tgcagaccta caagcgctga    19517
taaatgcgcc ggggccctcg ctgcgccccc ggccttccaa taatgacaat aatgaggagt    19577
gcccaatgtt tcacgtgccc ctgcttattg gtggtaagcc ttgttcagca tctgatgagc    19637
gcaccttcga gcgtcgtagc ccgctgaccg gagaagtggt atcgcgcgtc gctgctgcca    19697
gtttggaaga tgcggacgcc gcagtggccg ctgcacaggc tgcgtttcct gaatgggcgg    19757
cgcttgctcc gagcgaacgc cgtgcccgac tgctgcgagc ggcggatctt ctagaggacc    19817
```

-continued

```
gttcttccga gttcaccgcc gcagcgagtg aaactggcgc agcggaaac tggtatgggt      19877
ttaacgttta cctggcggcg ggcatgttgc gggaagccgc ggccatgacc acacagattc    19937
agggcgatgt cattccgtcc aatgtgcccg gtagctttgc catggcggtt cgacagccat    19997
gtggcgtggt gctcggtatt gcgccttgga atgctccggt aatccttggc gtacgggctg   20057
ttgcgatgcc gttggcatgc ggcaataccg tggtgttgaa aagctctgag ctgagtccct   20117
ttacccatcg cctgattggt caggtgttgc atgatgctgg tctggggat ggcgtggtga     20177
atgtcatcag caatgccccg caagacgctc ctgcggtggt ggagcgactg attgcaaatc    20237
ctgcggtacg tcgagtgaac ttcaccggtt cgacccacgt tggacggatc attggtgagc    20297
tgtctgcgcg tcatctgaag cctgctgtgc tggaattagg tggtaaggct ccgttcttgg    20357
tcttggacga tgccgacctc gatgcggcgg tcgaagcggc ggcctttggt gcctacttca    20417
atcagggtca aatctgcatg tccactgagc gtctgattgt gacagcagtc gcagacgcct    20477
ttgttgaaaa gctggcgagg aaggtcgcca cactgcgtgc tggcgatcct aatgatccgc    20537
aatcggtctt gggttcgttg attgatgcca atgcaggtca acgcatccag gttctggtcg    20597
atgatgcgct cgcaaaaggc gcgcggcagg tcgtcggtgg tggcttagat ggcagcatca    20657
tgcagccgat gctgcttgat caggtcactg aagagatgcg gctctaccgt gaggagtcct    20717
ttggccctgt tgccgttgtc ttgcgcggcg atggtgatga agaactgctg cgtcttgcca    20777
acgattcgga gtttggtctt tcggccgcca ttttcagccg tgacgtctcg cgcgcaatgg    20837
aattggccca gcgcgtcgat tcgggcattt gccatatcaa tggaccgact gtgcatgacg    20897
aggctcagat gccattcggt ggggtgaagt ccagcggcta cggcagcttc ggcagtcgag    20957
catcgattga gcactttacc cagctgcgct ggctgaccat tcagaatggc ccgcggcact    21017
atccaatcta aatcgatctt cgggcgccgc gggcatcatg cccgcggcgc tcgcctcatt    21077
tcaatctcta acttgataaa aacagagctg ttctccggtc ttggtggatc aaggccagtc    21137
gcggagagtc tcgaagagga gagtacagtg aacgccgagt ccacattgca accgcaggca    21197
tcatcatgct ctgctcagcc acgctaccgc agtgtgtcga ttggtcatcc tccggttgag    21257
gttacgcaag acgctggagg tattgtccgg atgcgttctc tcgaggcgct tcttcccttc    21317
ccgggtcgaa ttcttgagcg tctcgagcat tgggctaaga cccgtccaga acaaacctgc    21377
gttgctgcca gggcggcaaa tggggaatgg cgtcgtatca gctacgcgga atgttccac    21437
aacgtccgcg ccatcgcaca gagcttgctt ccttacggac tatcggcaga gcgtccgctg    21497
cttatcgtct ctggaaatga cctggaacat cttcagctgg catttggggc tatgtatgcg    21557
ggcattccct attgcccggt gtctcctgct tattcactgc tgtcgcaaga tttggcgaag    21617
ctgcgtcaca tcgtaggtct tctgcaaccg ggactggtct tgctgccga tgcagcacct     21677
ttccagcgcg caattgagac cattctgccg gacgacgtgc ccgcaatctt cactcgaggc    21737
gaattggccg ggcggcgcac ggtgagtttt gacagcctgc tggagcagcc tggtgggatt    21797
gaggcagata atgcctttgc ggcaactggc cccgatacga ttgccaagtt cttgttcact    21857
tctggctcta ccaaactgcc taaggcggtg ccgactactc agcgaatgct ctgcgccaat    21917
cagcagatgc ttctgcaaac tttccggtt tttggtgaag agccgccggt gctggtggac    21977
tggttgccgt ggaaccacac cttcggcggc agccacaaca tcggcatcgt gttgtacaac    22037
ggcggcacgt actaccttga cgacggtaaa ccaaccgccc aagggttcgc cgagacgctt    22097
cgcaacttga gcgaaatctc tcccactgcg tacctcactg tgccgaaagg ctgggaggaa    22157
ttagtgggtg cccttgagcg agacagtacc ctgcgcgaac gcttcttcgc tcgcatgaag    22217
```

```
ctgttcttct tcgcggcggc tgggttgtcg caagggatct gggatcgttt ggaccgggtc    22277
gctgaacagc actgtggtga gcgcattcgc atgatggcgg gtctgggcat gacggagact    22337
gctccttcct gcactttac caccggaccg ctgtcgatgc ctggttacat tgggctgcca    22397
gcgcctggct gcgaggtcaa gctcgttccg gtcgatggga aattggaagg gcgtttccat    22457
ggtccgcacg tcatgagcgg ctactggcgt gctcctgaac aaaatgccca agcgttcgac    22517
gaggaaggct attactgctc cggtgatgcc atcaaattgg cagatcctgc cgatcctcag    22577
aaaggtctga tgtttgacgg tcgaattgct gaagacttca agctgtcctc aggggtattt    22637
gtcagcgttg ggccattgcg cacgcgggcg gttctggaag gcggctctta cgtcctggac    22697
gtagtggttg ctgctcctga tcgtgaatgc cttggattgc tcgtgtttcc gcgtcttctc    22757
gactgccgtg ccttgtcggg gctaggaaaa gaggcgtcgg acgccgaggt gcttgccagt    22817
gagccggttc gggcctggtt tgctgactgg ctcaaacgac tcaatcgaga agcaactggc    22877
aatgccagtc gcatcatgtg ggtagggctc ctcgatacgc cgccgtcgat tgataagggc    22937
gaggtcactg acaagggctc gatcaaccag cgcgctgttt gcaatggcg gtcggcgaaa    22997 gttgatgcgc tgtatcgtgg tgaagatcaa tccatgctgc gtgacgaggc cacactgtga    23057
gttggtcagg gggggcttac tcggcgtttt ccgacactgc gttggttgcg gcagtgcgca    23117
ccccctggat tgattgcggg ggtgccctgt cgctggtgtc gcctatcgac ttagggggtaa    23177 aggtcgctcg cgaagttctg atgcgtgcgt cgcttgaacc acaaatggtc gatagcgtac    23237
tcgcaggctc tatggctcaa gcaagctttg atgcttacct gctcccgcgg cacattggct    23297
tgtacagcgc tgttcccaag tcggttccgg ccttgggggt gcagcgcatt tgcggcacag    23357
gcttcgaact gcttcggcag gccggcgagc agatttccca aggcgctgat cacgtgctgt    23417
gtgtcgcggc agagtccatg tcgcgtaacc ccatcgcgtc gtatacacac cggggcgggt    23477
tccgcctcgg tgcgcccgtt gagttcaagg attttttgtg ggaggcattg tttgatcctg    23537
ctccaggact cgacatgatc gctaccgcag aaaacctggc gcgcctgtac ggaatcacca    23597
ggggagaagc taattcctac gcggtaagca gcttcgagcg cgcattgagg gcgcaagagg    23657
agaaatggat tgaccaagag atcgtggctg ttacggatga acagttcgat ttagagggct    23717
acaacagtcg agcaattgaa ctgcctcgga aggcaaaatt gttgatcgtg acagtcatcc    23777
gcggcctagc agtctttgaa gccctttccc gattgaagcc tgttcattct ggcggggtgc    23837
agactgcggg caacagctgt gccgtagtgg acggcgccgc ggcggctttg gtggctcgag    23897
agtcgtctgc gacacagccg gtcttggcta ggatactggc tacctccgta gtcgggatcg    23957
agcccgagca tatgggggctc ggccctgcgc ccgcgattcg cctgctgctt gcgcgtagtg    24017
atcttagttt gagggatatc gacctctttg agataaacga ggcgcaggcc gcccaagttc    24077
tagcggtaca gcatgaattg ggtattgagc actcaaaact taatatttgg ggcggggcca    24137
ttgcacttgg acacccgctt gccgcgaccg gattgcgtct ctgcatgacc ctcgctcacc    24197
aattgcaagc taataacttt cgatatggaa ttgcctcggc atgcattggt gggggacagg    24257
ggatggcggt tcttttagag aatcccact tcggttcgtc ctctgcacga agttcgatga    24317
ttaacagagt tgaccactat ccactgagct aacgggcatc tcctttgttg ctttgaggtg    24377
gcgcacgaag gagggctcga aaatctctgc taaaacaag aagaaggaac agggaacatg    24437 attagttttcg ctcgtatggc agaaagttta ggagtccagg ctaaacttgc ccttgccttc    24497
gcactcgtat tatgtgtcgg gctgattgtt accggcacgg gtttctacag tgtacatacc    24557
```

```
ttgtcagggt tggtggaaaa gagcgcgata gctggtgagt tgcgggcgaa aattcaggaa    24617
ctgaaggttc tggagcagcg cgccttattc atcgccgatg aagggtcgct gaagcagcgc    24677
tcgatcctcc taagtcaggt gatagctgaa gttaatgatg ctatagatat ttttgacttt    24737
cagcgcggac gatctgagtt acttaaattc gctgcttctt cgcgcgaagc aagttactcc    24797
attgaggtcg gtagtaacgc tgcggccgat aagttgcagt cgggcgaacc aagtgacgca    24857
ttgatggttg ccgataaaaa gctgaatgtt gagtatgagc aattgagttc tgctgtgaat    24917
gcactgatgg ggcatttaat tgaggatcag aatgaaaaag ttccactaat ctactatatg    24977
cttggcggcg taactttgtt tacgatgctc atgagtgctt attcggtctg gttcatttcg    25037
cgtcagttag ttccgccatt aaagtcgacg gtgcagcttg ccgagcggat tgcatcaggc    25097
gacttggctg atgtcgggga cagcaggcgc aaggatgaaa tcggtcagtt gcaaagtgca    25157
actaggcgga tggcgattgg actgcgtaat ctggtcggtg atattggtca aagtcgtgcg    25217
caactggttt catcgtccag cgacctttcg gccatctgtg ctcaggctca gattgatgtc    25277
gagtgccaga agctttcggt cgcccaggtc tctaccgccg tgaacgagtt ggttgaaacc    25337
gtccaggcaa tagcaaaaag caccgaagag gcagcaacag tcgccgtctt ggccgatgaa    25397
aaggcacgcg gtggtgaaag tgtcgttaac aaggccgttg atttcattga gcacctctcc    25457
ggagatatgg cggaactggg agacgcaatg gagcggcttc agaacgacag tgcgcagatc    25517
aataaggtag tagacgtcat taaggctgtg gcggagcaga ccaatctgct agccctgaat    25577
gcggcgatag aggcggcccg tgcaggagag cagggcaggg gctttgcggt cgtggcggat    25637
gaggttcgtg ctttggcgat gcgcacccaa caatcgacca agaaattga gaggctagtg    25697 gtttcattgc agcagggaag tgaagctgcg ggcgagttga tgcggcgtgg caaggtccgg    25757
acgcatgacg tcgttggatt ggcccagcaa gccgcgcgcc gcgctactcg aaattaccca    25817
gctgtcgccg gcatccaagc gatgaactat cagatcgccg ctggagcaga gcagcaaggg    25877
gctgctgtgg ttcaaatcaa ccagaatatg cttgaagtgc ataagatggc tgacgagtcc    25937
gccattaaag cgggacagac catgaagtca tcgaaggagc ttgctcacct cggcagtgcg    25997
ctacaaaaat ccgttgatcg attccagctg tagcgctccg ggtggctgaa acgcgcattt    26057
tcgttaaggt cttcagcgcg gtctgctggt gcgtgggccg ctagcctaac tgttgcgctt    26117
caggctccgc atggatcttg tgcagcagca atagcaattg ttcacgttcg tcatcactca    26177
gcatcgacgt cgcgtcttgg tcgctctgta ccacgatctt cttcagctct ttgagctgcg    26237
tctccccagc tttgctgaga aatatcccat aggaacgctt gtccggcttg cagcgcacgc    26297
gcacagcaag gccgagcttc tcgagcttgt tcagcaaggg aaccagttgt ggtggttcga    26357
ttgcgagcat ccgcgctagg tcagcctgca taagcccagg gctcgcttcg atgattagaa    26417
gtgccgacag ctgcgccggg cgtaggtcat atggcgtcag gcttcaatc aggccctgag    26477 cgagcttcag ctgtgagccg gcgtaaggca tagccaatca attgattcag gagcgtatcg    26537
cccggttcta tcagcgggcc gctttcgaaa gtcatggtgt tagccggtag ggtctttttc    26597
ttggccatgc ttgttgcctg aaccttcgtt gacatagggc agaggtgcgt ttgccgcttc    26657
gcttcgcgat gaaccgcatc gagatgctga ggtcaggatt tttccttaac tcgcgtaagc    26717
attctgtcat tttttttggtg gctttgaaca gcctgatgaa aggtggtctc gccctttgag    26777
gccgattctt gggcgcttgg cggcgtcgaa gcgatgctcc actaccgatt aagataatta    26837
aaataaggaa accgcatggt ttcttatgtg aatttgtctg gcatactcca gctcaagggc    26897
aatttttggg ctattggctg agcagttgcc tctatatggt tattcagaat aacaattgac    26957
```

```
tcctcaggag gtcagcgatg agcattcttg gtttgaatgg tgccccggtc ggagctgagc   27017
agctgggctc ggctcttgat cgcatgaaga aggcgcacct ggagcagggg cctgcaaact   27077
tggagctgcg tctgagtagg ctggatcgtg cgattgcaat gcttctggaa aatcgtgaag   27137
caattgccga cgcggtttct gctgactttg gcaatcgcag ccgtgagcaa acactgcttt   27197
gcgacattgc tggctcggtg gcaagcctga aggatagccg cgagcacgtg gccaaatgga   27257
tggagcccga acatcacaag gcgatgtttc caggggcgga ggcacgcgtt gagtttcagc   27317
cgctgggtgt cgttggggtc attagtccct ggaacttccc tatcgtactg gcctttgggc   27377
cgctggccgg catattcgca gcaggtaatc gcgccatgct caagccgtcc gagcttaccc   27437
cgcggacttc tgccctgctt gcggagctaa ttgctcgtta cttcgatgaa actgagctga   27497
ctacagtgct gggcgacgct gaagtcggtg cgctgttcag tgctcagcct ttcgatcatc   27557
tgatcttcac cggcggcact gccgtggcca agcacatcat gcgtgccgcg gcggataacc   27617
tagtgcccgt tacccctggaa ttgggtggca aatcgccggt gatcgtttcc cgcagtgcag   27677
atatggcgga cgttgcacaa cgggtgttga cggtgaaaac cttcaatgcc gggcaaatct   27737
gtctggcacc ggactatgtg ctgctgccgg aagaatcgct ggatagcttt gtcgccgagg   27797
cgacgcgctt cgtggccgca atgtatccct cgcttctaga taatccggat tacacgtcga   27857
tcatcaatgc ccgaaatttc gaccgtctgc atcgctacct gactgatgcg caggcaaagg   27917
gagggcgcgt cattgaaatc aatcctgcgg ccgaagagtt gggggatagt ggtatcagga   27977
agatcgcgcc cactttgatc gtgaatgtgt cggatgaaat gctggtcttg aacgaggaga   28037
tctttggtcc gctgctcccg atcaagactt atcgtgattt cgactcggct atcgactacg   28097
tcaacagcaa gcagcgacca cttgcctcgt acttcttcgg cgaagatgcg gttgagcgtg   28157
agcaagtgct taagcgtacg gtttcgggcg ccgtggtcgt gaacgatgtc atgagccatg   28217
tgatgatgga tacgcttcca tttggtggtg tggggcactc ggggatgggg gcatatcacg   28277
gcatttatgg tttccgaacc ttcagccatg ccaagcctgt tctcgtgcaa agtcctgtgg   28337
gtgagtcgaa cttggcgatg cgcgcaccct acggagaagc gatccacgga ctgctctctg   28397
tcctcctttc aacggagtgt tagaaccgtt ggtagtggtt ttggacgggc ccaggagcat   28457
gcgcttctgg gcccgtttct tgagtattca ttggatagtc acgcgtggta gcttcgagcc   28517
tgcacagctg atgagcaccc tggaaggcgc gctgtacgcg gacgactggg ttcatcttcg   28577
ccattcatga cggaactccg ttccccagta ccgcgatgac tattttgcct cttccgatgt   28637
ccgattccac gccgcctgac gctaagcggg ggcgggggcg cccgcatccc agcccagaca   28697
gcaacaaatg agtaggctct tggatgccgc ggcggctgag attggtaacg gcaatttcgt   28757
caatgtgacg atggattcga ttgcccgtgc tgccggcgtc tcaaaaaaaa cgctgtacgt   28817
cttggtggcg agcaaggaag aactcattttc ccggttagtg gctcgagaca tgtccaacct   28877
tgagctgctg ctttgtcacg aggttgagtc tgcggaggcc cttcaggatg agttgcgaaa   28937
ctatctgctg ctctgggcgc gcttgacctt gtccctctt gctttgggca ttttctgat   28997 ggccgtgcag gggcgtgaaa gtgcccccggg cctggcgaga atctggtatc gagaggggc    29057 agagcgttgc ctcagcttgc ttcggggatg gttggcaagg atggcaagcc gggagctgat   29117
cgctcctgga gatatcgact ccgcagtgga gcttatcgat tcgctcctga tctcacagcc   29177
tttgaaatta tttggcctgg ggatccgag cggctggacc gatgatcaga tcaatcaacg    29237
ggtcacaatc gctctcgatg cattccgtcg gtgctatgtc gtttagcacc gttctcgcgg   29297
```

-continued

```
gctgtggcgg cgtgacctat ttgtctagtg gtcggcgcga aattcgataa gaaagctggg   29357
cgcgagtgag gccgagccgg cgggcagctt ccgagacatt gccttccacc tggcccagag   29417
catggctaat catcgcgtcc tccacttctt gcagcgtcat cgcgctcagg tcctttgagt   29477
caagcggcga gtcgattgtg ctggtcggtt tggagaagga agtacttggg ctgccagttt   29537
cctgtggctg attatcttga gcggtggcca ggatgccgct ggccccaatg agaacatcg    29597 gttgagtcag tcgttcaccg ctagtgaaga ggtggctcac gtcaatggct ccatcctccg   29657
gagcgctgat gactccgcgc tccaccaaat tttgaagctc ccggatgttt cctgaaagt    29717 cgtagccaag cagggcattg gctgcacgtg gagtgaatcc gctgaccacc cggctatgac   29777
gctgattgaa gcggtgcagg aaataggtca tcaggagggg aatgtcttcc ttcctctctc   29837
gaagcggcgg gaggtggatc gggtaaacat tgaggcggaa aaaaaggtcc tcgcggaact   29897
cgccgcgctg gacgcctgcg cgaagatcga cattggttgc ggctaccaca cggacgtcaa   29957
ccttgagtgt cctgcttccg ccaacccgtt cgacctccga ctcttgcagg gcgcgaagta   30017
acttcccttg ggccacgagg cttagcgtcc ctatctcgtc aaggaatagt gtgccgcccg   30077
aagcgcgctc gaaccgtcct gctcgagatt gggtggcgcc ggtaaacgcc cccgttcga    30137 cgccgaacaa ctcggactcc atcagggttt cgggaatacg tgcgcaattg accgcaacaa   30197
acgggccgtc gtgtctgggg ctgatgcggt gaagcatgcg ggcgaacatc tccttgccca   30257
cacctgattc acccgtaaac agtaccgtcg cctccgtggg tgctacgcgc ttcagcatgt   30317
ggcaggcagc attgaatgcc gaggaaattc ccaccatgtc gtgttccgat gcagtgcttg   30377
agtctgcggc ggagtgatgg ggagtgttcc tttgtccctg ctgcgttctt cgtctctgcg   30437
gcgtgcttgg ttgccgacaa atggttgcgc taagcgccgc caagtcctct tcggcgtctt   30497
cccattcttc cgctggcttg ccgatcatgc ggcagatctg cgaacccgtg gagcggcatt   30557
ccacctctcg gtaaaggatg aggcgaccaa ccagcgcgga cgtatagcca atggcataac   30617
ccgtctgcgt ccagcacgcg ggctcggtgc cgatgccgta gtgcgcaata tgttcatcat   30677
cttcgctcga atggtgccag aggaattcgc cgtagtaggt ccccaaatcc atgtcgaagt   30737
cgaagtggat cggctccacg cgtactgcgc cttccagaga gtgcaagttc gggccggcgg   30797
caaataggga gagcggatcg gcgttgctga agcgctcctt cagaagggcg gcatctttgg   30857
cgccgcagtg gtaaccggtt cgcagcatga ttccgcgggc gcgggcgaag cccacgcttt   30917
caattaattc gcgtcgcaat gcacccagtc cgctgctgtg gaggagcagc attcgcgcgc   30977
cgttcaacca gatgcgtcca tcgccagggc tgaaaaggag ggattcagtg aggtcatgaa   31037
gggaggggac ggcgcctggc tccaattgct cgatggcgcc gcgattgagt gtcttgggcg   31097
cggtcttgga gagttcggct agggagataa atttgctggc catggtggcg gccctgatg    31157 ggttggatga ttttctgcat tctgcatcat gaaattcatg aaatcatcac ttttcggggg   31217
gtgggtgcac gggattgaag gttgctagga gagtgcattg ctcgtaagcc caggaagcac   31277
gcgggtttca ggatggtgca tggaaatggc atgagctttg ctggatatga ttagagacat   31337
taactatttt ggcggaatgg aagcacgatt cctcgcccgg tagagcggta accgcgacat   31397
tcaggaccgt aaaaggaaa gagcatgcaa ctgaccaaca agaaaatcgt cgtcaccgga   31457
gtgtcctccg gtatcggtgc cgaaactgcc cgcgttctgc gctctcacgg cgccacagtg   31517
attggcgtag atcgcaacat gccgagcctg actctggatg cttcgttcca ggctgacctg   31577
agccatcctg aaggcatcga taaggccatc tctcagctgc ggagaaaat tgacggactc   31637 tgcaatatcg ccggggtgcc cggcactgcc gatcctcagc tcgtcgcaaa cgtgaactac   31697
```

-continued

```
ctgggtctaa agtatctgac cgaggcagtc ctgtcgcgca ttcaacccgg tggttcgatt      31757
gtcaacgtgt cctctgtgct tggcgccgag tggccggccc gccttcagtt gcataaggag      31817
ctggggagtg ttgttggatt ctccgaaggc caggcatggc ttaagcagaa tccagtggcc      31877
cccgaattct gctaccagta tttcaaagaa gcactgatcg tttggtctca agttcaggcg      31937
caggaatggt tcatgaggac gtctgtacgc atgaactgca tcgcccccgg ccctgtattc      31997
actcccattc tcaatgagtt cgtcaccatg ctgggtcaag agcggactca ggcggacgct      32057
catcgtatta agcgcccagc atatgccgat gaagtggccg cggtgattgc attcatgtgt      32117
gctgaggagt cacgttggat caacggcata aatattccag tggacggagg tttggcatcg      32177
acctacgtgt aagttcgtgg acgcccttTg cacgcgcact atatctctat gcagcagctg      32237
aaagcagctt tggttttgat cggaggtagc gggcggaaag gtgcagaatg tctaaataat      32297
aaaggattct tgtgaagctt tagttgtccg taaacgaaaa taaaaataaa gaggaatgat      32357
atgaaagcaa gtagatcagt ctgcactttc aaaatagcta ccctggcagg cgccatttat      32417
gcagcgctgc caatgtcagc tgcaaactcg atgcagctgg atgtaggtag ctcggattgg      32477
acggtgcgtt ggggacaaca ccctcaagta tagccttgcc tctcgcctga atgagcaaga      32537
ctcaagtctg acaaatgcgc cgactgtcaa tggttatatc cggatattca aagtcagggt      32597
gatcgtaact tgaccggggg cttggtatc caatcgtctc gatattctgt cggagcttga       32657
tgtcagtcgt gactggttgg tg                                               32679
```

<210> SEQ ID NO 2
<211> LENGTH: 284
<212> TYPE: PRT
<213> ORGANISM: Pseudomonas sp.

<400> SEQUENCE: 2

```
Met Ile Ala Ile Thr Gly Ala Ser Gly Gln Leu Gly Arg Leu Thr Ile
  1               5                  10                  15

Glu Ala Leu Leu Lys Arg Leu Pro Ala Ser Glu Ile Ile Ala Leu Val
                 20                  25                  30

Arg Asp Pro Asn Lys Ala Gly Asp Leu Thr Ala Arg Gly Ile Val Val
             35                  40                  45

Arg Gln Ala Asp Tyr Asn Arg Pro Glu Thr Leu His Arg Ala Leu Ile
         50                  55                  60

Gly Val Asn Arg Leu Leu Leu Ile Ser Ser Glu Val Gly Gln Arg
     65                  70                  75                  80

Thr Ala Gln His Arg Ala Val Ile Asp Ala Lys Gln Glu Gly Ile
                 85                  90                  95

Glu Leu Leu Ala Tyr Thr Ser Leu Leu His Ala Asp Lys Ser Ala Leu
                100                 105                 110

Gly Leu Ala Thr Glu His Arg Asp Thr Glu Gln Ala Leu Thr Glu Ser
            115                 120                 125

Gly Ile Pro His Val Leu Leu Arg Asn Gly Trp Tyr His Glu Asn Tyr
        130                 135                 140

Thr Ala Gly Ile Pro Val Ala Leu Val His Gly Val Leu Leu Gly Cys
145                 150                 155                 160

Ala Gln Asp Gly Leu Ile Ala Ser Ala Arg Ala Asp Tyr Ala Glu
                165                 170                 175

Ala Ala Ala Val Val Leu Thr Gly Glu Asn Gln Ala Gly Arg Val Tyr
                180                 185                 190
```

```
Glu Leu Ala Gly Glu Pro Ala Tyr Thr Leu Thr Glu Leu Ala Ala Glu
            195                 200                 205

Val Ala Pro Gln Ala Gly Lys Thr Val Val Tyr Ser Asn Leu Ser Glu
        210                 215                 220

Ser Asp Tyr Arg Ser Ala Leu Ile Ser Ala Gly Leu Pro Asp Gly Phe
225                 230                 235                 240

Ala Ala Leu Leu Ala Asp Ser Asp Ala Gly Ala Lys Gly Tyr Leu
                245                 250                 255

Phe Asp Ser Ser Gly Asp Ser Arg Lys Leu Ile Gly Arg Pro Thr Thr
                260                 265                 270

Pro Met Ser Glu Ala Ile Ala Ala Ile Gly Arg
            275                 280

<210> SEQ ID NO 3
<211> LENGTH: 1065
<212> TYPE: DNA
<213> ORGANISM: not required under old rule
<220> FEATURE:
<221> NAME/KEY: CDS
<222> LOCATION: (1)..(1062)
<223> OTHER INFORMATION: product = "Vanillinsaeure-O-Demethylase" / gene
      = "vanA"

<400> SEQUENCE: 3 atg ttt ccg aaa aac gcc tgg tat gtc gct tgc act ccg gat gaa atc      48
Met Phe Pro Lys Asn Ala Trp Tyr Val Ala Cys Thr Pro Asp Glu Ile
1               5                   10                  15 gca gat aag ccg cta ggc cgt cag atc tgc aac gaa aag att gtc ttc      96
Ala Asp Lys Pro Leu Gly Arg Gln Ile Cys Asn Glu Lys Ile Val Phe
            20                  25                  30 tat cgg ggg ccg gaa gga cgt gtt gcc gcg gta gag gat ttc tgc cct    144
Tyr Arg Gly Pro Glu Gly Arg Val Ala Ala Val Glu Asp Phe Cys Pro
        35                  40                  45 cat cgc ggg gca ccg ttg tcc ctg ggt ttc gtt cgc gac ggt aag ctg    192
His Arg Gly Ala Pro Leu Ser Leu Gly Phe Val Arg Asp Gly Lys Leu
    50                  55                  60 att tgc ggc tac cac ggt ttg gaa atg ggc tgc gag ggc aaa acg ctc    240
Ile Cys Gly Tyr His Gly Leu Glu Met Gly Cys Glu Gly Lys Thr Leu
65                  70                  75                  80 gcg atg ccc ggg cag cgc gtt caa ggc ttc cct tgc atc aaa agc tac    288
Ala Met Pro Gly Gln Arg Val Gln Gly Phe Pro Cys Ile Lys Ser Tyr
                85                  90                  95 gcg gta gaa gag cga tac ggc ttt atc tgg gta tgg cct ggt gat cgc    336
Ala Val Glu Glu Arg Tyr Gly Phe Ile Trp Val Trp Pro Gly Asp Arg
            100                 105                 110 gag ctg gcg gat ccg gcg ctt att cac cac ctg gag tgg gcc gat aat    384
Glu Leu Ala Asp Pro Ala Leu Ile His His Leu Glu Trp Ala Asp Asn
        115                 120                 125 ccg gag tgg gcc tat ggt ggc ggt ctc tac cac atc gct tgt gat tac    432
Pro Glu Trp Ala Tyr Gly Gly Gly Leu Tyr His Ile Ala Cys Asp Tyr
    130                 135                 140 cgc ctg atg atc gac aac ctc atg gat ctc acc cat gag acc tat gtg    480
Arg Leu Met Ile Asp Asn Leu Met Asp Leu Thr His Glu Thr Tyr Val
145                 150                 155                 160 cat gcc tcc agc atc ggt caa aag gaa att gac gag gca ccg gtc agt    528
His Ala Ser Ser Ile Gly Gln Lys Glu Ile Asp Glu Ala Pro Val Ser
                165                 170                 175 act cgt gtc gag ggc gac acc gtg att acc agc cgg tac atg gat aac    576
Thr Arg Val Glu Gly Asp Thr Val Ile Thr Ser Arg Tyr Met Asp Asn
            180                 185                 190
```

```
gtc atg gcc cct ccg ttc tgg cgt gct gcg ctt cgt ggc aac ggc ttg        624
Val Met Ala Pro Pro Phe Trp Arg Ala Ala Leu Arg Gly Asn Gly Leu
    195                 200                 205 gcc gac gat gta ccg gtt gat cgc tgg cag atc tgc cga ttc gct cct        672
Ala Asp Asp Val Pro Val Asp Arg Trp Gln Ile Cys Arg Phe Ala Pro
210                 215                 220 ccg agt cac gta ctg atc gaa gta ggt gtg gct cat gcg ggc aaa ggc        720
Pro Ser His Val Leu Ile Glu Val Gly Val Ala His Ala Gly Lys Gly
225                 230                 235                 240 gga tat gac gcg ccg gcg gaa tac aag gcc ggc agc ata gtg gtc gac        768
Gly Tyr Asp Ala Pro Ala Glu Tyr Lys Ala Gly Ser Ile Val Val Asp
                245                 250                 255 ttc atc acg ccg gag agt gat acc tcg att tgg tac ttc tgg ggc atg        816
Phe Ile Thr Pro Glu Ser Asp Thr Ser Ile Trp Tyr Phe Trp Gly Met
            260                 265                 270 gct cgc aac ttc cgt ccg cag ggc acg gag ctg act gaa acc att cgt        864
Ala Arg Asn Phe Arg Pro Gln Gly Thr Glu Leu Thr Glu Thr Ile Arg
        275                 280                 285 gtt ggt cag ggc aag att ttt gcc gag gac ctg gac atg ctg gag cag        912
Val Gly Gln Gly Lys Ile Phe Ala Glu Asp Leu Asp Met Leu Glu Gln
290                 295                 300 cag cag cgc aat ctg ctg gcc tac ccg gag cgc cag ttg ctc aag ctg        960
Gln Gln Arg Asn Leu Leu Ala Tyr Pro Glu Arg Gln Leu Leu Lys Leu
305                 310                 315                 320 aat atc gat gcc ggc ggg gtt cag tca cgg cgc gtc att gat cgg att       1008
Asn Ile Asp Ala Gly Gly Val Gln Ser Arg Arg Val Ile Asp Arg Ile
                325                 330                 335 ctc gca gct gaa caa gag gcc gca gac gca gcg ctg atc gcg aga agt       1056
Leu Ala Ala Glu Gln Glu Ala Ala Asp Ala Ala Leu Ile Ala Arg Ser
            340                 345                 350 gca tca tga                                                           1065
Ala Ser <210> SEQ ID NO 4
<211> LENGTH: 354
<212> TYPE: PRT
<213> ORGANISM: not required under old rule

<400> SEQUENCE: 4

Met Phe Pro Lys Asn Ala Trp Tyr Val Ala Cys Thr Pro Asp Glu Ile
1               5                   10                  15

Ala Asp Lys Pro Leu Gly Arg Gln Ile Cys Asn Glu Lys Ile Val Phe
            20                  25                  30

Tyr Arg Gly Pro Glu Gly Arg Val Ala Ala Val Glu Asp Phe Cys Pro
        35                  40                  45

His Arg Gly Ala Pro Leu Ser Leu Gly Phe Val Arg Asp Gly Lys Leu
    50                  55                  60

Ile Cys Gly Tyr His Gly Leu Glu Met Gly Cys Glu Gly Lys Thr Leu
65                  70                  75                  80

Ala Met Pro Gly Gln Arg Val Gln Gly Phe Pro Cys Ile Lys Ser Tyr
                85                  90                  95

Ala Val Glu Glu Arg Tyr Gly Phe Ile Trp Val Trp Pro Gly Asp Arg
            100                 105                 110

Glu Leu Ala Asp Pro Ala Leu Ile His His Leu Glu Trp Ala Asp Asn
        115                 120                 125

Pro Glu Trp Ala Tyr Gly Gly Leu Tyr His Ile Ala Cys Asp Tyr
    130                 135                 140

Arg Leu Met Ile Asp Asn Leu Met Asp Leu Thr His Glu Thr Tyr Val
```

```
                        145                 150                 155                 160
His Ala Ser Ser Ile Gly Gln Lys Glu Ile Asp Ala Pro Val Ser
                165                 170                 175

Thr Arg Val Glu Gly Asp Thr Val Ile Thr Ser Arg Tyr Met Asp Asn
            180                 185                 190

Val Met Ala Pro Pro Phe Trp Arg Ala Ala Leu Arg Gly Asn Gly Leu
        195                 200                 205

Ala Asp Asp Val Pro Val Asp Arg Trp Gln Ile Cys Arg Phe Ala Pro
        210                 215                 220

Pro Ser His Val Leu Ile Glu Val Gly Val Ala His Ala Gly Lys Gly
225                 230                 235                 240

Gly Tyr Asp Ala Pro Ala Glu Tyr Lys Ala Gly Ser Ile Val Val Asp
                245                 250                 255

Phe Ile Thr Pro Glu Ser Asp Thr Ser Ile Trp Tyr Phe Trp Gly Met
                260                 265                 270

Ala Arg Asn Phe Arg Pro Gln Gly Thr Glu Leu Thr Glu Thr Ile Arg
            275                 280                 285

Val Gly Gln Gly Lys Ile Phe Ala Glu Asp Leu Asp Met Leu Glu Gln
        290                 295                 300

Gln Gln Arg Asn Leu Leu Ala Tyr Pro Glu Arg Gln Leu Leu Lys Leu
305                 310                 315                 320

Asn Ile Asp Ala Gly Gly Val Gln Ser Arg Arg Val Ile Asp Arg Ile
                325                 330                 335

Leu Ala Ala Glu Gln Glu Ala Ala Asp Ala Ala Leu Ile Ala Arg Ser
                340                 345                 350

Ala Ser
```

<210> SEQ ID NO 5
<211> LENGTH: 954
<212> TYPE: DNA
<213> ORGANISM: not required under old rule
<220> FEATURE:
<221> NAME/KEY: CDS
<222> LOCATION: (1)..(951)
<223> OTHER INFORMATION: product = "Vanillin-O-Demethylase"/ gene = "vanB"

<400> SEQUENCE: 5

```
atg att gag gta atc att tcg gcg atg cgc ttg gtt gct cag gac atc        48
Met Ile Glu Val Ile Ile Ser Ala Met Arg Leu Val Ala Gln Asp Ile
 1               5                  10                  15 att agc ctt gag ttt gtc cgg gct gac ggt ggc ttg ctt ccg cct gtc        96
Ile Ser Leu Glu Phe Val Arg Ala Asp Gly Gly Leu Leu Pro Pro Val
            20                  25                  30 gag gcc ggc gcc cac gtc gat gtg cat ctt cct ggc ggc ctg att cgg       144
Glu Ala Gly Ala His Val Asp Val His Leu Pro Gly Gly Leu Ile Arg
        35                  40                  45 cag tac tcg ctc tgg aat caa cca ggg gcg cag agc cat tac tgc atc       192
Gln Tyr Ser Leu Trp Asn Gln Pro Gly Ala Gln Ser His Tyr Cys Ile
    50                  55                  60 ggt gtt ctg aag gac ccg gcg tct cgt ggt ggt tcg aag gcg gtg cac       240
Gly Val Leu Lys Asp Pro Ala Ser Arg Gly Gly Ser Lys Ala Val His
65                  70                  75                  80 gag aat ctt cgc gtc ggg atg cgc gtg caa att agc gag ccg agg aac       288
Glu Asn Leu Arg Val Gly Met Arg Val Gln Ile Ser Glu Pro Arg Asn
                85                  90                  95 cta ttc cca ttg gaa gag ggg gtg gag cgg agt ctg ctg ttc gcg ggc       336
Leu Phe Pro Leu Glu Glu Gly Val Glu Arg Ser Leu Leu Phe Ala Gly
```

-continued

|     |     |     |     | 100 |     |     |     |     | 105 |     |     |     |     | 110 |     |     |
| --- | --- | --- | --- | --- | --- | --- | --- | --- | --- | --- | --- | --- | --- | --- | --- | --- |
| ggg | att | ggc | att | acg | ccg | att | ctg | tgt | atg | gct | caa | gaa | tta | gca | gca | 384 |
| Gly | Ile | Gly | Ile | Thr | Pro | Ile | Leu | Cys | Met | Ala | Gln | Glu | Leu | Ala | Ala |     |
|     |     |     |     | 115 |     |     |     |     | 120 |     |     |     |     | 125 |     |     |

| cgc | gag | caa | gat | ttc | gag | ttg | cat | tat | tgc | gcg | cgt | tcg | acc | gac | cga | 432 |
| Arg | Glu | Gln | Asp | Phe | Glu | Leu | His | Tyr | Cys | Ala | Arg | Ser | Thr | Asp | Arg |     |
|     |     | 130 |     |     |     |     | 135 |     |     |     |     | 140 |     |     |     |     |

| gcg | gcg | ttc | gtt | gaa | tgg | ctt | aag | gtt | tgc | gac | ttt | gct | gat | cac | gta | 480 |
| Ala | Ala | Phe | Val | Glu | Trp | Leu | Lys | Val | Cys | Asp | Phe | Ala | Asp | His | Val |     |
| 145 |     |     |     |     | 150 |     |     |     |     | 155 |     |     |     |     | 160 |     |

| cgt | ttc | cac | ttt | gac | aat | ggc | ccg | gat | cag | caa | aaa | ctg | aat | gcc | gca | 528 |
| Arg | Phe | His | Phe | Asp | Asn | Gly | Pro | Asp | Gln | Gln | Lys | Leu | Asn | Ala | Ala |     |
|     |     |     |     | 165 |     |     |     |     | 170 |     |     |     |     | 175 |     |     |

| gcg | ctg | cta | gcg | gcc | gag | gcc | gaa | ggt | acc | cac | ctt | tat | gtc | tgt | ggg | 576 |
| Ala | Leu | Leu | Ala | Ala | Glu | Ala | Glu | Gly | Thr | His | Leu | Tyr | Val | Cys | Gly |     |
|     |     |     | 180 |     |     |     |     | 185 |     |     |     |     | 190 |     |     |     |

| ccc | ggc | ggg | ttc | atg | ggg | cat | gtg | ctt | gat | acc | gcg | aag | gag | cag | ggc | 624 |
| Pro | Gly | Gly | Phe | Met | Gly | His | Val | Leu | Asp | Thr | Ala | Lys | Glu | Gln | Gly |     |
|     |     | 195 |     |     |     |     | 200 |     |     |     |     | 205 |     |     |     |     |

| tgg | gct | gac | aat | cga | ctg | cat | cga | gag | tat | ttc | gcc | gcg | gcg | ccg | aat | 672 |
| Trp | Ala | Asp | Asn | Arg | Leu | His | Arg | Glu | Tyr | Phe | Ala | Ala | Ala | Pro | Asn |     |
|     | 210 |     |     |     |     | 215 |     |     |     |     | 220 |     |     |     |     |     |

| gtg | agt | gct | gac | gat | ggc | agt | ttc | gag | gtg | cgg | att | cac | agc | acc | gga | 720 |
| Val | Ser | Ala | Asp | Asp | Gly | Ser | Phe | Glu | Val | Arg | Ile | His | Ser | Thr | Gly |     |
| 225 |     |     |     |     | 230 |     |     |     |     | 235 |     |     |     |     | 240 |     |

| caa | gtg | ctt | cag | gtc | ccc | gcg | gat | caa | acg | gtc | tcc | cag | gtg | ctc | gat | 768 |
| Gln | Val | Leu | Gln | Val | Pro | Ala | Asp | Gln | Thr | Val | Ser | Gln | Val | Leu | Asp |     |
|     |     |     |     | 245 |     |     |     |     | 250 |     |     |     |     | 255 |     |     |

| gcg | gcc | gga | att | atc | gtt | ccc | gtt | tct | tgt | gag | cag | ggc | atc | tgc | ggt | 816 |
| Ala | Ala | Gly | Ile | Ile | Val | Pro | Val | Ser | Cys | Glu | Gln | Gly | Ile | Cys | Gly |     |
|     |     |     | 260 |     |     |     |     | 265 |     |     |     |     | 270 |     |     |     |

| act | tgc | atc | act | cgg | gtg | gta | gac | gga | gag | cct | gat | cat | cgt | gac | ttc | 864 |
| Thr | Cys | Ile | Thr | Arg | Val | Val | Asp | Gly | Glu | Pro | Asp | His | Arg | Asp | Phe |     |
|     |     | 275 |     |     |     |     | 280 |     |     |     |     | 285 |     |     |     |     |

| ttc | ctc | acg | gat | gcg | gag | aag | gca | aag | aac | gac | cag | ttc | acc | ccc | tgt | 912 |
| Phe | Leu | Thr | Asp | Ala | Glu | Lys | Ala | Lys | Asn | Asp | Gln | Phe | Thr | Pro | Cys |     |
|     | 290 |     |     |     |     | 295 |     |     |     |     | 300 |     |     |     |     |     |

| tgc | tcg | cga | gcc | aag | agc | gcc | tgt | ttg | gtc | ttg | gat | ctc | taa |     |     | 954 |
| Cys | Ser | Arg | Ala | Lys | Ser | Ala | Cys | Leu | Val | Leu | Asp | Leu |     |     |     |     |
| 305 |     |     |     |     | 310 |     |     |     |     | 315 |     |     |     |     |     |     |

<210> SEQ ID NO 6
<211> LENGTH: 317
<212> TYPE: PRT
<213> ORGANISM: not required under old rule

<400> SEQUENCE: 6

Met Ile Glu Val Ile Ile Ser Ala Met Arg Leu Val Ala Gln Asp Ile
1               5                   10                  15

Ile Ser Leu Glu Phe Val Arg Ala Asp Gly Gly Leu Leu Pro Pro Val
                20                  25                  30

Glu Ala Gly Ala His Val Asp Val His Leu Pro Gly Gly Leu Ile Arg
            35                  40                  45

Gln Tyr Ser Leu Trp Asn Gln Pro Gly Ala Gln Ser His Tyr Cys Ile
        50                  55                  60

Gly Val Leu Lys Asp Pro Ala Ser Arg Gly Gly Ser Lys Ala Val His
65                  70                  75                  80

Glu Asn Leu Arg Val Gly Met Arg Val Gln Ile Ser Glu Pro Arg Asn
                85                  90                  95

```
Leu Phe Pro Leu Glu Glu Gly Val Glu Arg Ser Leu Leu Phe Ala Gly
            100                 105                 110
Gly Ile Gly Ile Thr Pro Ile Leu Cys Met Ala Gln Glu Leu Ala Ala
        115                 120                 125
Arg Glu Gln Asp Phe Glu Leu His Tyr Cys Ala Arg Ser Thr Asp Arg
    130                 135                 140
Ala Ala Phe Val Glu Trp Leu Lys Val Cys Asp Phe Ala Asp His Val
145                 150                 155                 160
Arg Phe His Phe Asp Asn Gly Pro Asp Gln Gln Lys Leu Asn Ala Ala
                165                 170                 175
Ala Leu Leu Ala Ala Glu Ala Glu Gly Thr His Leu Tyr Val Cys Gly
            180                 185                 190
Pro Gly Gly Phe Met Gly His Val Leu Asp Thr Ala Lys Glu Gln Gly
        195                 200                 205
Trp Ala Asp Asn Arg Leu His Arg Glu Tyr Phe Ala Ala Pro Asn
    210                 215                 220
Val Ser Ala Asp Asp Gly Ser Phe Glu Val Arg Ile His Ser Thr Gly
225                 230                 235                 240
Gln Val Leu Gln Val Pro Ala Asp Gln Thr Val Ser Gln Val Leu Asp
                245                 250                 255
Ala Ala Gly Ile Ile Val Pro Val Ser Cys Glu Gln Gly Ile Cys Gly
            260                 265                 270
Thr Cys Ile Thr Arg Val Val Asp Gly Glu Pro Asp His Arg Asp Phe
        275                 280                 285
Phe Leu Thr Asp Ala Glu Lys Ala Lys Asn Asp Gln Phe Thr Pro Cys
    290                 295                 300
Cys Ser Arg Ala Lys Ser Ala Cys Leu Val Leu Asp Leu
305                 310                 315
```

<210> SEQ ID NO 7
<211> LENGTH: 1119
<212> TYPE: DNA
<213> ORGANISM: not required under old rule
<220> FEATURE:
<221> NAME/KEY: CDS
<222> LOCATION: (1)..(1116)
<223> OTHER INFORMATION: product = "Formaldehyd-Dehydrogenase"/ gene = "fdh"

<400> SEQUENCE: 7

```
atg atc aaa tcc cgc gcc gct gtg gcg ttc gca ccc aat cag cca ttg      48
Met Ile Lys Ser Arg Ala Ala Val Ala Phe Ala Pro Asn Gln Pro Leu
  1               5                  10                  15 cag atc gtc gaa gtg gac gtg gct ccg ccc aag gcc ggt gaa gtc ctg      96
Gln Ile Val Glu Val Asp Val Ala Pro Pro Lys Ala Gly Glu Val Leu
                 20                  25                  30 gtg cgg gtc gtg gcc acc ggc gtt tgc cac acc gat gcc tac acc ctg     144
Val Arg Val Val Ala Thr Gly Val Cys His Thr Asp Ala Tyr Thr Leu
             35                  40                  45 tcc ggc gct gat tcc gag ggc gtt ttc ccc tgc atc ctt ggt cac gaa     192
Ser Gly Ala Asp Ser Glu Gly Val Phe Pro Cys Ile Leu Gly His Glu
         50                  55                  60 ggc ggc ggc att gtc gaa gcg gtg ggc gag ggc gtc acc tcg ctg gcg     240
Gly Gly Gly Ile Val Glu Ala Val Gly Glu Gly Val Thr Ser Leu Ala
 65                  70                  75                  80 gtc ggc gac cac gtg atc ccg ctc tac acg gcc gaa tgc cgt gag tgc     288
Val Gly Asp His Val Ile Pro Leu Tyr Thr Ala Glu Cys Arg Glu Cys
                 85                  90                  95
```

```
aag ttc ttc aag tcc ggc aag acc aac ctg tgc cag aaa gtg cgt gct      336
Lys Phe Phe Lys Ser Gly Lys Thr Asn Leu Cys Gln Lys Val Arg Ala
            100                 105                 110 act cag ggc aag ggt ctg atg ccg gac ggc acc tcc cgc ttc agc tac      384
Thr Gln Gly Lys Gly Leu Met Pro Asp Gly Thr Ser Arg Phe Ser Tyr
        115                 120                 125 aac ggt cag ccg atc tac cac tac atg ggc tgc tcg acc ttc tcc gag      432
Asn Gly Gln Pro Ile Tyr His Tyr Met Gly Cys Ser Thr Phe Ser Glu
    130                 135                 140 tac acc gtg ctg ccg gaa atc tcc ctg gcg aag att ccc aag aat gcg      480
Tyr Thr Val Leu Pro Glu Ile Ser Leu Ala Lys Ile Pro Lys Asn Ala
145                 150                 155                 160 ccg ctg gag aaa gtc tgc ctg ctg ggc tgc ggc gtg acc acc ggc att      528
Pro Leu Glu Lys Val Cys Leu Leu Gly Cys Gly Val Thr Thr Gly Ile
                165                 170                 175 ggc gcg gtg ctg aac act gcc aag gtg gag gag ggt gct acc gtg gcc      576
Gly Ala Val Leu Asn Thr Ala Lys Val Glu Glu Gly Ala Thr Val Ala
            180                 185                 190 atc ttc ggc ctg ggc ggc atc ggc ttg gcg gcg atc atc ggc gcg aag      624
Ile Phe Gly Leu Gly Gly Ile Gly Leu Ala Ala Ile Ile Gly Ala Lys
        195                 200                 205 atg gcc aag gcc tcg cgc atc atc gcc atc gac atc aat ccg tcc aag      672
Met Ala Lys Ala Ser Arg Ile Ile Ala Ile Asp Ile Asn Pro Ser Lys
    210                 215                 220 ttc gat gtg gct cgc gag ctg ggc gcc act gac ttc gtc aat ccg aac      720
Phe Asp Val Ala Arg Glu Leu Gly Ala Thr Asp Phe Val Asn Pro Asn
225                 230                 235                 240 gat cac gcg aag ccg atc cag gat gtc atc gtc gag atg act gat ggc      768
Asp His Ala Lys Pro Ile Gln Asp Val Ile Val Glu Met Thr Asp Gly
                245                 250                 255 ggt gtg gac tac agc ttc gag tgc atc ggc aac gtt cga ctc atg cgc      816
Gly Val Asp Tyr Ser Phe Glu Cys Ile Gly Asn Val Arg Leu Met Arg
            260                 265                 270 gca gca ctc gag tgc tgc cac aag ggc tgg ggc gaa tcc gtg atc atc      864
Ala Ala Leu Glu Cys Cys His Lys Gly Trp Gly Glu Ser Val Ile Ile
        275                 280                 285 ggc gtg gcg ccg gcg ggg gcc gaa atc aac acc cgt ccg ttc cac ctg      912
Gly Val Ala Pro Ala Gly Ala Glu Ile Asn Thr Arg Pro Phe His Leu
    290                 295                 300 gtg acc ggt cgc gtc tgg cgg ggt tcg gcg ttc ggt ggc gta aag ggc      960
Val Thr Gly Arg Val Trp Arg Gly Ser Ala Phe Gly Gly Val Lys Gly
305                 310                 315                 320 cgc acc gaa ctg ccg agc tac gtg gag aag gca cag cag ggc gag atc     1008
Arg Thr Glu Leu Pro Ser Tyr Val Glu Lys Ala Gln Gln Gly Glu Ile
                325                 330                 335 ccg ctg gac acc ttc atc act cac acc atg ggc ctg gac gac atc aac     1056
Pro Leu Asp Thr Phe Ile Thr His Thr Met Gly Leu Asp Asp Ile Asn
            340                 345                 350 acg gcc ttc gac ctg atg gac gaa ggg aag agc atc cgc tct gtt gtt     1104
Thr Ala Phe Asp Leu Met Asp Glu Gly Lys Ser Ile Arg Ser Val Val
        355                 360                 365 caa ttg agt cgc tag                                                  1119
Gln Leu Ser Arg
    370

<210> SEQ ID NO 8
<211> LENGTH: 372
<212> TYPE: PRT
<213> ORGANISM: not required under old rule
```

```
<400> SEQUENCE: 8

Met Ile Lys Ser Arg Ala Ala Val Ala Phe Ala Pro Asn Gln Pro Leu
  1               5                  10                  15

Gln Ile Val Glu Val Asp Val Ala Pro Pro Lys Ala Gly Glu Val Leu
             20                  25                  30

Val Arg Val Val Ala Thr Gly Val Cys His Thr Asp Ala Tyr Thr Leu
         35                  40                  45

Ser Gly Ala Asp Ser Glu Gly Val Phe Pro Cys Ile Leu Gly His Glu
     50                  55                  60

Gly Gly Gly Ile Val Glu Ala Val Gly Glu Gly Val Thr Ser Leu Ala
 65                  70                  75                  80

Val Gly Asp His Val Ile Pro Leu Tyr Thr Ala Glu Cys Arg Glu Cys
                 85                  90                  95

Lys Phe Phe Lys Ser Gly Lys Thr Asn Leu Cys Gln Lys Val Arg Ala
            100                 105                 110

Thr Gln Gly Lys Gly Leu Met Pro Asp Gly Thr Ser Arg Phe Ser Tyr
        115                 120                 125

Asn Gly Gln Pro Ile Tyr His Tyr Met Gly Cys Ser Thr Phe Ser Glu
130                 135                 140

Tyr Thr Val Leu Pro Glu Ile Ser Leu Ala Lys Ile Pro Lys Asn Ala
145                 150                 155                 160

Pro Leu Glu Lys Val Cys Leu Leu Gly Cys Gly Val Thr Thr Gly Ile
                165                 170                 175

Gly Ala Val Leu Asn Thr Ala Lys Val Glu Glu Gly Ala Thr Val Ala
            180                 185                 190

Ile Phe Gly Leu Gly Gly Ile Gly Leu Ala Ala Ile Gly Ala Lys
        195                 200                 205

Met Ala Lys Ala Ser Arg Ile Ile Ala Ile Asp Ile Asn Pro Ser Lys
    210                 215                 220

Phe Asp Val Ala Arg Glu Leu Gly Ala Thr Asp Phe Val Asn Pro Asn
225                 230                 235                 240

Asp His Ala Lys Pro Ile Gln Asp Val Ile Val Glu Met Thr Asp Gly
                245                 250                 255

Gly Val Asp Tyr Ser Phe Glu Cys Ile Gly Asn Val Arg Leu Met Arg
            260                 265                 270

Ala Ala Leu Glu Cys Cys His Lys Gly Trp Gly Glu Ser Val Ile Ile
        275                 280                 285

Gly Val Ala Pro Ala Gly Ala Glu Ile Asn Thr Arg Pro Phe His Leu
290                 295                 300

Val Thr Gly Arg Val Trp Arg Gly Ser Ala Phe Gly Gly Val Lys Gly
305                 310                 315                 320

Arg Thr Glu Leu Pro Ser Tyr Val Glu Lys Ala Gln Gln Gly Glu Ile
                325                 330                 335

Pro Leu Asp Thr Phe Ile Thr His Thr Met Gly Leu Asp Asp Ile Asn
            340                 345                 350

Thr Ala Phe Asp Leu Met Asp Glu Gly Lys Ser Ile Arg Ser Val Val
        355                 360                 365

Gln Leu Ser Arg
    370

<210> SEQ ID NO 9
<211> LENGTH: 1638
<212> TYPE: DNA
<213> ORGANISM: not required under old rule
```

<220> FEATURE:
<221> NAME/KEY: CDS
<222> LOCATION: (1)..(1635)
<223> OTHER INFORMATION: product = "gamma-Glutamylcystein-Synthetase" /
      gene = "gcs"

<400> SEQUENCE: 9

```
atg ccg caa act ctt gct gga cgg ttg agt ctg tta tcc ggc acc gac      48
Met Pro Gln Thr Leu Ala Gly Arg Leu Ser Leu Leu Ser Gly Thr Asp
 1               5                  10                  15 gaa tta acc ctg ctt ctt cgg ggt ggt cgg ggc att gag cgt gaa gcc      96
Glu Leu Thr Leu Leu Leu Arg Gly Gly Arg Gly Ile Glu Arg Glu Ala
             20                  25                  30 ttg cgg gtc gat gtt caa ggt gaa ctg gcg ctg acg cct cac ccg gcg     144
Leu Arg Val Asp Val Gln Gly Glu Leu Ala Leu Thr Pro His Pro Ala
         35                  40                  45 gcg ctt ggc tct gcg ttg acc cat ccg aca att act acg gat tac gcc     192
Ala Leu Gly Ser Ala Leu Thr His Pro Thr Ile Thr Thr Asp Tyr Ala
     50                  55                  60 gag gcc ctg ctt gag ttg atc act cgg ccg gca acc gat tgt gcg caa     240
Glu Ala Leu Leu Glu Leu Ile Thr Arg Pro Ala Thr Asp Cys Ala Gln
 65                  70                  75                  80 gcc ttg gct gag ctg gag gag ctt cac cgt ttc gtt cat tcg aga ctt     288
Ala Leu Ala Glu Leu Glu Glu Leu His Arg Phe Val His Ser Arg Leu
                 85                  90                  95 gag ggg gag tat ctc tgg aat ctg tcc atg cct ggc aga ttg ccg gtt     336
Glu Gly Glu Tyr Leu Trp Asn Leu Ser Met Pro Gly Arg Leu Pro Val
            100                 105                 110 gat gag caa atc ccg att gct tgg tat gga cca tca aat cca ggc atg     384
Asp Glu Gln Ile Pro Ile Ala Trp Tyr Gly Pro Ser Asn Pro Gly Met
        115                 120                 125 ttg cgc cac gtt tat cgc cgt ggc cta gct ctg cgt tat ggc aag cga     432
Leu Arg His Val Tyr Arg Arg Gly Leu Ala Leu Arg Tyr Gly Lys Arg
    130                 135                 140 atg caa tgc atc gca ggg att cac tac aac tac tca ctg ccg cca gag     480
Met Gln Cys Ile Ala Gly Ile His Tyr Asn Tyr Ser Leu Pro Pro Glu
145                 150                 155                 160 ctt ttc gct gtc ctg acc aag gca gag gtc ggg tct ccc aag tta ctg     528
Leu Phe Ala Val Leu Thr Lys Ala Glu Val Gly Ser Pro Lys Leu Leu
                165                 170                 175 gag cgc cag tca gca gct tac atg cgc caa att cgc aac ctt cgg caa     576
Glu Arg Gln Ser Ala Ala Tyr Met Arg Gln Ile Arg Asn Leu Arg Gln
            180                 185                 190 tac ggt tgg ttg ctg gcc tac ttg ttc ggc gct tcc ccc gcc atc tgc     624
Tyr Gly Trp Leu Leu Ala Tyr Leu Phe Gly Ala Ser Pro Ala Ile Cys
        195                 200                 205 aag agc ttc ttg ggg ggc gag aga gat gag cta gct cgc atg ggg ggc     672
Lys Ser Phe Leu Gly Gly Glu Arg Asp Glu Leu Ala Arg Met Gly Gly
    210                 215                 220 gat acg ctt tac atg ccc tat gca acc agc ttg cgc atg agt gac atc     720
Asp Thr Leu Tyr Met Pro Tyr Ala Thr Ser Leu Arg Met Ser Asp Ile
225                 230                 235                 240 ggg tac cgc aac cgt gcc atg gat gat cta tct ccc agc ctg aat gat     768
Gly Tyr Arg Asn Arg Ala Met Asp Asp Leu Ser Pro Ser Leu Asn Asp
                245                 250                 255 ctg ggt gcc tat att cgc gat att tgc cgt gct ctt cac act ccc gat     816
Leu Gly Ala Tyr Ile Arg Asp Ile Cys Arg Ala Leu His Thr Pro Asp
            260                 265                 270 gcc cag tac cag gcg ctg ggt gtg ttt gca cag ggc gag tgg cgg cag     864
Ala Gln Tyr Gln Ala Leu Gly Val Phe Ala Gln Gly Glu Trp Arg Gln
        275                 280                 285
```

```
tta aac gcc aat cta ttg cag ttg gat agt gag tac tac gca ctg gcg      912
Leu Asn Ala Asn Leu Leu Gln Leu Asp Ser Glu Tyr Tyr Ala Leu Ala
        290                 295                 300 cga ccg aag tca gcg ccc gag cgg ggg gag cga aac ctg gat gct ctc      960
Arg Pro Lys Ser Ala Pro Glu Arg Gly Glu Arg Asn Leu Asp Ala Leu
305                 310                 315                 320 gct agg cgt gga gtc cag tat gtg gag ctg cgc gca ctg gat ctc gat     1008
Ala Arg Arg Gly Val Gln Tyr Val Glu Leu Arg Ala Leu Asp Leu Asp
                325                 330                 335 cca ttc tcc ccg tta ggc att ggc ctg acc tgc gcc aag ttc ctc gat     1056
Pro Phe Ser Pro Leu Gly Ile Gly Leu Thr Cys Ala Lys Phe Leu Asp
            340                 345                 350 ggc ttt ttg ctt ttc tgc ttg ttg tct gag gcg ccg gtt gat gat cga     1104
Gly Phe Leu Leu Phe Cys Leu Leu Ser Glu Ala Pro Val Asp Asp Arg
        355                 360                 365 aat gcc cag cgt tca aga ccg gga aaa tct gag cct ggc cgg caa gta     1152
Asn Ala Gln Arg Ser Arg Pro Gly Lys Ser Glu Pro Gly Arg Gln Val
    370                 375                 380 cgg gcg tca cct ggc tta aag ctg cat cgg aat ggt cag tcc att ctc     1200
Arg Ala Ser Pro Gly Leu Lys Leu His Arg Asn Gly Gln Ser Ile Leu
385                 390                 395                 400 ctc aag gat tgg gcg cag gaa gtg ttg acg gag gtt cag gcc tgt gtg     1248
Leu Lys Asp Trp Ala Gln Glu Val Leu Thr Glu Val Gln Ala Cys Val
                405                 410                 415 gaa ttg ctc gac agt gca aat ggg ggc tca tct cac gca ttg gct tgg     1296
Glu Leu Leu Asp Ser Ala Asn Gly Gly Ser Ser His Ala Leu Ala Trp
            420                 425                 430 tca gca cag gag gaa aag gtg ctt aat ccg gat tgt gcg cca tca gct     1344
Ser Ala Gln Glu Glu Lys Val Leu Asn Pro Asp Cys Ala Pro Ser Ala
        435                 440                 445 cag gtg ctc gca gag ata cac aga cac ggt ggg agc ttc acg gca ttt     1392
Gln Val Leu Ala Glu Ile His Arg His Gly Gly Ser Phe Thr Ala Phe
    450                 455                 460 ggt cgc caa tta gct atc gac cat gca aaa cac ttc agt gcc tcc tcg     1440
Gly Arg Gln Leu Ala Ile Asp His Ala Lys His Phe Ser Ala Ser Ser
465                 470                 475                 480 ctt gag gct ggc gta gcc aaa gcg ctt gac ctc cag gcg acg tcg tct     1488
Leu Glu Ala Gly Val Ala Lys Ala Leu Asp Leu Gln Ala Thr Ser Ser
                485                 490                 495 ctg cgc gag cag cat caa ttg gag gcc aac gac cgt gcg cca ttt tct     1536
Leu Arg Glu Gln His Gln Leu Glu Ala Asn Asp Arg Ala Pro Phe Ser
            500                 505                 510 gac tac ctt cag caa ttc tcc ctg gct ttc ggt caa tcc gtc ggc gcc     1584
Asp Tyr Leu Gln Gln Phe Ser Leu Ala Phe Gly Gln Ser Val Gly Ala
        515                 520                 525 tct cgt gcg ccc aac cct acc gcg cac ctc atc gat ctg acc cct cct     1632
Ser Arg Ala Pro Asn Pro Thr Ala His Leu Ile Asp Leu Thr Pro Pro
    530                 535                 540 gtc taa                                                             1638
Val
545

<210> SEQ ID NO 10
<211> LENGTH: 545
<212> TYPE: PRT
<213> ORGANISM: not required under old rule

<400> SEQUENCE: 10

Met Pro Gln Thr Leu Ala Gly Arg Leu Ser Leu Leu Ser Gly Thr Asp
  1               5                  10                  15
```

-continued

```
Glu Leu Thr Leu Leu Arg Gly Gly Arg Gly Ile Glu Arg Glu Ala
         20                  25                  30
Leu Arg Val Asp Val Gln Gly Glu Leu Ala Leu Thr Pro His Pro Ala
         35                  40                  45
Ala Leu Gly Ser Ala Leu Thr His Pro Thr Ile Thr Thr Asp Tyr Ala
 50                  55                  60
Glu Ala Leu Leu Glu Leu Ile Thr Arg Pro Ala Thr Asp Cys Ala Gln
 65                  70                  75                  80
Ala Leu Ala Glu Leu Glu Glu Leu His Arg Phe Val His Ser Arg Leu
                 85                  90                  95
Glu Gly Glu Tyr Leu Trp Asn Leu Ser Met Pro Gly Arg Leu Pro Val
                100                 105                 110
Asp Glu Gln Ile Pro Ile Ala Trp Tyr Gly Pro Ser Asn Pro Gly Met
                115                 120                 125
Leu Arg His Val Tyr Arg Arg Gly Leu Ala Leu Arg Tyr Gly Lys Arg
                130                 135                 140
Met Gln Cys Ile Ala Gly Ile His Tyr Asn Tyr Ser Leu Pro Pro Glu
145                 150                 155                 160
Leu Phe Ala Val Leu Thr Lys Ala Glu Val Gly Ser Pro Lys Leu Leu
                165                 170                 175
Glu Arg Gln Ser Ala Ala Tyr Met Arg Gln Ile Arg Asn Leu Arg Gln
                180                 185                 190
Tyr Gly Trp Leu Leu Ala Tyr Leu Phe Gly Ala Ser Pro Ala Ile Cys
                195                 200                 205
Lys Ser Phe Leu Gly Gly Glu Arg Asp Glu Leu Ala Arg Met Gly Gly
        210                 215                 220
Asp Thr Leu Tyr Met Pro Tyr Ala Thr Ser Leu Arg Met Ser Asp Ile
225                 230                 235                 240
Gly Tyr Arg Asn Arg Ala Met Asp Asp Leu Ser Pro Ser Leu Asn Asp
                245                 250                 255
Leu Gly Ala Tyr Ile Arg Asp Ile Cys Arg Ala Leu His Thr Pro Asp
                260                 265                 270
Ala Gln Tyr Gln Ala Leu Gly Val Phe Ala Gln Gly Glu Trp Arg Gln
                275                 280                 285
Leu Asn Ala Asn Leu Leu Gln Leu Asp Ser Glu Tyr Tyr Ala Leu Ala
        290                 295                 300
Arg Pro Lys Ser Ala Pro Glu Arg Gly Glu Arg Asn Leu Asp Ala Leu
305                 310                 315                 320
Ala Arg Arg Gly Val Gln Tyr Val Glu Leu Arg Ala Leu Asp Leu Asp
                325                 330                 335
Pro Phe Ser Pro Leu Gly Ile Gly Leu Thr Cys Ala Lys Phe Leu Asp
                340                 345                 350
Gly Phe Leu Leu Phe Cys Leu Leu Ser Glu Ala Pro Val Asp Asp Arg
        355                 360                 365
Asn Ala Gln Arg Ser Arg Pro Gly Lys Ser Glu Pro Gly Arg Gln Val
        370                 375                 380
Arg Ala Ser Pro Gly Leu Lys Leu His Arg Asn Gly Gln Ser Ile Leu
385                 390                 395                 400
Leu Lys Asp Trp Ala Gln Glu Val Leu Thr Glu Val Gln Ala Cys Val
                405                 410                 415
Glu Leu Leu Asp Ser Ala Asn Gly Gly Ser Ser His Ala Leu Ala Trp
                420                 425                 430
```

```
Ser Ala Gln Glu Glu Lys Val Leu Asn Pro Asp Cys Ala Pro Ser Ala
        435                 440                 445

Gln Val Leu Ala Glu Ile His Arg His Gly Ser Phe Thr Ala Phe
        450                 455                 460

Gly Arg Gln Leu Ala Ile Asp His Ala Lys His Phe Ser Ala Ser Ser
465                 470                 475                 480

Leu Glu Ala Gly Val Ala Lys Ala Leu Asp Leu Gln Ala Thr Ser Ser
                485                 490                 495

Leu Arg Glu Gln His Gln Leu Glu Ala Asn Asp Arg Ala Pro Phe Ser
                500                 505                 510

Asp Tyr Leu Gln Gln Phe Ser Leu Ala Phe Gly Gln Ser Val Gly Ala
        515                 520                 525

Ser Arg Ala Pro Asn Pro Thr Ala His Leu Ile Asp Leu Thr Pro Pro
    530                 535                 540
Val
545

<210> SEQ ID NO 11
<211> LENGTH: 354
<212> TYPE: DNA
<213> ORGANISM: not required under old rule
<220> FEATURE:
<221> NAME/KEY: CDS
<222> LOCATION: (1)..(351)
<223> OTHER INFORMATION: product = "Cytochrom C UE-Eugenol-Hydroxylase"
      / gene = "chyA"

<400> SEQUENCE: 11 atg atg aat gtt aat tat aag gct gtc ggg gcg agc cta ctc ctc gcc      48
Met Met Asn Val Asn Tyr Lys Ala Val Gly Ala Ser Leu Leu Leu Ala
1               5                   10                  15 ttc atc tct cag gga gct tgg gca gag agc ccc gca gcc tct ggc aat      96
Phe Ile Ser Gln Gly Ala Trp Ala Glu Ser Pro Ala Ala Ser Gly Asn
            20                  25                  30 acc cct gac att tat cga aag acc tgc acc tac tgc cat gag cct act     144
Thr Pro Asp Ile Tyr Arg Lys Thr Cys Thr Tyr Cys His Glu Pro Thr
        35                  40                  45 gtc aac aat ggc cgg gtc att gcc cga agc ctc ggg ccg act ctg cga     192
Val Asn Asn Gly Arg Val Ile Ala Arg Ser Leu Gly Pro Thr Leu Arg
    50                  55                  60 ggg cgc cag atc cct cca cag tac acg gag tac atg gtg cgt cat gga     240
Gly Arg Gln Ile Pro Pro Gln Tyr Thr Glu Tyr Met Val Arg His Gly
65                  70                  75                  80 cgc ggg gca atg cct gca ttc tct gaa gca gaa gtg cct ccg gcg gag     288
Arg Gly Ala Met Pro Ala Phe Ser Glu Ala Glu Val Pro Pro Ala Glu
                85                  90                  95 ctg aaa gtt ctg ggc gat tgg att cag caa agc agt gct ccc aaa gac     336
Leu Lys Val Leu Gly Asp Trp Ile Gln Gln Ser Ser Ala Pro Lys Asp
            100                 105                 110 gct gga gtc gcg cca tga                                              354
Ala Gly Val Ala Pro
        115

<210> SEQ ID NO 12
<211> LENGTH: 117
<212> TYPE: PRT
<213> ORGANISM: not required under old rule

<400> SEQUENCE: 12

Met Met Asn Val Asn Tyr Lys Ala Val Gly Ala Ser Leu Leu Leu Ala
1               5                   10                  15
```

```
Phe Ile Ser Gln Gly Ala Trp Ala Glu Ser Pro Ala Ala Ser Gly Asn
            20                  25                  30

Thr Pro Asp Ile Tyr Arg Lys Thr Cys Thr Tyr Cys His Glu Pro Thr
        35                  40                  45

Val Asn Asn Gly Arg Val Ile Ala Arg Ser Leu Gly Pro Thr Leu Arg
    50                  55                  60

Gly Arg Gln Ile Pro Pro Gln Tyr Thr Glu Tyr Met Val Arg His Gly
65                  70                  75                  80

Arg Gly Ala Met Pro Ala Phe Ser Glu Ala Glu Val Pro Pro Ala Glu
                85                  90                  95

Leu Lys Val Leu Gly Asp Trp Ile Gln Gln Ser Ser Ala Pro Lys Asp
            100                 105                 110

Ala Gly Val Ala Pro
            115

<210> SEQ ID NO 13
<211> LENGTH: 687
<212> TYPE: DNA
<213> ORGANISM: not required under old rule
<220> FEATURE:
<221> NAME/KEY: CDS
<222> LOCATION: (1)..(684)
<223> OTHER INFORMATION: gene = "ORF5"

<400> SEQUENCE: 13 atg act acc cgt cgc aac ttt cta ata ggc gcg tcg cag gtg ggg gca     48
Met Thr Thr Arg Arg Asn Phe Leu Ile Gly Ala Ser Gln Val Gly Ala
  1               5                  10                  15 ttg gtg atg atg tcg ccg aaa ttg gtc ttc cgt acg ccg ctc aag cag     96
Leu Val Met Met Ser Pro Lys Leu Val Phe Arg Thr Pro Leu Lys Gln
                20                  25                  30 aag ccc gtg cgc atc ctg tcg acc ggg ctg gcc ggt gag caa gag ttt    144
Lys Pro Val Arg Ile Leu Ser Thr Gly Leu Ala Gly Glu Gln Glu Phe
            35                  40                  45 cac tcg atg ctt cgc gcg cga ttg acc cat acg ggt cag gtc gac atc    192
His Ser Met Leu Arg Ala Arg Leu Thr His Thr Gly Gln Val Asp Ile
        50                  55                  60 gcg tcg gta ccg ctg gac gca gct att tgg gct tct ccc gct cga ctt    240
Ala Ser Val Pro Leu Asp Ala Ala Ile Trp Ala Ser Pro Ala Arg Leu
 65                 70                  75                  80 gcc cag gca atg gat gcg ttg aat ggt acg cgt ctg atc gct ttt gtt    288
Ala Gln Ala Met Asp Ala Leu Asn Gly Thr Arg Leu Ile Ala Phe Val
                85                  90                  95 gag ccc agg aac gaa ttg ata ctg atg caa ttc ttg atg gat cgc ggg    336
Glu Pro Arg Asn Glu Leu Ile Leu Met Gln Phe Leu Met Asp Arg Gly
            100                 105                 110 gct gcg gtg ctt att caa ggt gag cat gcg gtg gac agc aag ggg gtc    384
Ala Ala Val Leu Ile Gln Gly Glu His Ala Val Asp Ser Lys Gly Val
        115                 120                 125 tct cgg cac gac ttt ctg agt acc cca tcc agt gcg gga att gga ggg    432
Ser Arg His Asp Phe Leu Ser Thr Pro Ser Ser Ala Gly Ile Gly Gly
    130                 135                 140 gcg cta gcc gac agc ctg gca aaa ggg ggc tcg ccg ttc tct att tcc    480
Ala Leu Ala Asp Ser Leu Ala Lys Gly Gly Ser Pro Phe Ser Ile Ser
145                 150                 155                 160 gtc cga gcg ctt ggc tcg gta act gct cag cca aga agt aat cag agt    528
Val Arg Ala Leu Gly Ser Val Thr Ala Gln Pro Arg Ser Asn Gln Ser
                165                 170                 175 gag gtg gcc acc cac tgg acg acc gct ctg ggg acc tat tat gcc gat    576
Glu Val Ala Thr His Trp Thr Thr Ala Leu Gly Thr Tyr Tyr Ala Asp
```

```
atc gca gtg ggg cgc tgg gag ccg cag cgc gaa gtg gcc agc tat gga     624
Ile Ala Val Gly Arg Trp Glu Pro Gln Arg Glu Val Ala Ser Tyr Gly
        195                 200                 205 agt gga cta atc atg gcg gaa cgg ctt gat cgt gtt gcc tca acc ttc     672
Ser Gly Leu Ile Met Ala Glu Arg Leu Asp Arg Val Ala Ser Thr Phe
    210                 215                 220 att gca gat ctc tga                                                  687
Ile Ala Asp Leu
225
```

<210> SEQ ID NO 14
<211> LENGTH: 228
<212> TYPE: PRT
<213> ORGANISM: not required under old rule

<400> SEQUENCE: 14

```
Met Thr Thr Arg Arg Asn Phe Leu Ile Gly Ala Ser Gln Val Gly Ala
  1               5                  10                  15

Leu Val Met Met Ser Pro Lys Leu Val Phe Arg Thr Pro Leu Lys Gln
             20                  25                  30

Lys Pro Val Arg Ile Leu Ser Thr Gly Leu Ala Gly Glu Gln Glu Phe
         35                  40                  45

His Ser Met Leu Arg Ala Arg Leu Thr His Thr Gly Gln Val Asp Ile
     50                  55                  60

Ala Ser Val Pro Leu Asp Ala Ala Ile Trp Ala Ser Pro Ala Arg Leu
 65                  70                  75                  80

Ala Gln Ala Met Asp Ala Leu Asn Gly Thr Arg Leu Ile Ala Phe Val
                 85                  90                  95

Glu Pro Arg Asn Glu Leu Ile Leu Met Gln Phe Leu Met Asp Arg Gly
            100                 105                 110

Ala Ala Val Leu Ile Gln Gly Glu His Ala Val Asp Ser Lys Gly Val
        115                 120                 125

Ser Arg His Asp Phe Leu Ser Thr Pro Ser Ser Ala Gly Ile Gly Gly
    130                 135                 140

Ala Leu Ala Asp Ser Leu Ala Lys Gly Gly Ser Pro Phe Ser Ile Ser
145                 150                 155                 160

Val Arg Ala Leu Gly Ser Val Thr Ala Gln Pro Arg Ser Asn Gln Ser
                165                 170                 175

Glu Val Ala Thr His Trp Thr Thr Ala Leu Gly Thr Tyr Tyr Ala Asp
            180                 185                 190

Ile Ala Val Gly Arg Trp Glu Pro Gln Arg Glu Val Ala Ser Tyr Gly
        195                 200                 205

Ser Gly Leu Ile Met Ala Glu Arg Leu Asp Arg Val Ala Ser Thr Phe
    210                 215                 220

Ile Ala Asp Leu
225
```

<210> SEQ ID NO 15
<211> LENGTH: 1554
<212> TYPE: DNA
<213> ORGANISM: not required under old rule
<220> FEATURE:
<221> NAME/KEY: CDS
<222> LOCATION: (1)..(1551)
<223> OTHER INFORMATION: product = " Flavoprotein UE-Eugenol-
      Hydroxylase" / gene = "ehyB"

<400> SEQUENCE: 15

```
atg gaa agc acc gta gtt ctt ccc gag ggt gtc acc ccg gag cag ttc        48
Met Glu Ser Thr Val Val Leu Pro Glu Gly Val Thr Pro Glu Gln Phe
 1               5                  10                  15 acc aaa gcc atc agc gag ttc cgt cag gta ttg ggt gag gac agt gtt        96
Thr Lys Ala Ile Ser Glu Phe Arg Gln Val Leu Gly Glu Asp Ser Val
             20                  25                  30 ctt gtc act gct gaa cga gtt gtt ccc tat acg aaa ctc ctc att cct       144
Leu Val Thr Ala Glu Arg Val Val Pro Tyr Thr Lys Leu Leu Ile Pro
         35                  40                  45 aca cag gat gat gcc cag tac acc ccg gcc ggt gcc ttg act cct tct       192
Thr Gln Asp Asp Ala Gln Tyr Thr Pro Ala Gly Ala Leu Thr Pro Ser
     50                  55                  60 tcg gtg gag cag gtc cag aaa gtc atg ggg atc tgc aat aag tac aag       240
Ser Val Glu Gln Val Gln Lys Val Met Gly Ile Cys Asn Lys Tyr Lys
 65                  70                  75                  80 atc ccg gta tgg cca atc tct acc ggt cgg aac tgg ggg tat ggg tcc       288
Ile Pro Val Trp Pro Ile Ser Thr Gly Arg Asn Trp Gly Tyr Gly Ser
                 85                  90                  95 gct tcg cct gca act cct ggg cag atg att ctt gac ctt cgc aag atg       336
Ala Ser Pro Ala Thr Pro Gly Gln Met Ile Leu Asp Leu Arg Lys Met
            100                 105                 110 aac aag atc att gag atc gat gtt gag ggg tgt act gcc ctc ctc gag       384
Asn Lys Ile Ile Glu Ile Asp Val Glu Gly Cys Thr Ala Leu Leu Glu
        115                 120                 125 ccg ggc gtt acc tac cag cag ctt cac gat tac atc aag gag cac aat       432
Pro Gly Val Thr Tyr Gln Gln Leu His Asp Tyr Ile Lys Glu His Asn
    130                 135                 140 ctg ccc ttg atg ctg gat gtg ccg act att ggg cct atg gtt ggc ccg       480
Leu Pro Leu Met Leu Asp Val Pro Thr Ile Gly Pro Met Val Gly Pro
145                 150                 155                 160 gtg ggt aac acg ctg gat cga ggc gtt ggt tat acg ccg tac ggc gag       528
Val Gly Asn Thr Leu Asp Arg Gly Val Gly Tyr Thr Pro Tyr Gly Glu
                165                 170                 175 cac ttc atg atg cag tgt ggt atg gaa gtc gtc atg gcc gat ggc gaa       576
His Phe Met Met Gln Cys Gly Met Glu Val Val Met Ala Asp Gly Glu
            180                 185                 190 atc ctc cgt act ggt atg ggc tcg gtg ccc aaa gcc aag act tgg cag       624
Ile Leu Arg Thr Gly Met Gly Ser Val Pro Lys Ala Lys Thr Trp Gln
        195                 200                 205 gca ttc aaa tgg ggc tat ggt cca tat ctg gac ggt atc ttt acc cag       672
Ala Phe Lys Trp Gly Tyr Gly Pro Tyr Leu Asp Gly Ile Phe Thr Gln
    210                 215                 220 tcc aac ttt ggt gtt gtg aca aag ctc ggg att tgg ttg atg ccc aag       720
Ser Asn Phe Gly Val Val Thr Lys Leu Gly Ile Trp Leu Met Pro Lys
225                 230                 235                 240 ccg cca gtg atc aag tcg ttt atg atc cgt tat ccc aat gaa gct gat       768
Pro Pro Val Ile Lys Ser Phe Met Ile Arg Tyr Pro Asn Glu Ala Asp
                245                 250                 255 gtg gtt aag gca att gat gct ttt cgc ccg ctg cgt att act cag ctg       816
Val Val Lys Ala Ile Asp Ala Phe Arg Pro Leu Arg Ile Thr Gln Leu
            260                 265                 270 att cct aac gtc gtt ttg ttc atg cac ggc atg tac gaa acg gca atc       864
Ile Pro Asn Val Val Leu Phe Met His Gly Met Tyr Glu Thr Ala Ile
        275                 280                 285 tgc cgg acg cgt gct gag gtt act tcg gac cca ggt cct att tct gaa       912
Cys Arg Thr Arg Ala Glu Val Thr Ser Asp Pro Gly Pro Ile Ser Glu
    290                 295                 300 gcg gac gcc cgc aaa gca ttc aaa gag cta ggc gtt ggc tac tgg aac       960
Ala Asp Ala Arg Lys Ala Phe Lys Glu Leu Gly Val Gly Tyr Trp Asn
```

```
                305                 310                 315                 320
gtt tac ttc gcg ctt tac ggc aca gaa gag cag ata gcc gtc aat gaa      1008
Val Tyr Phe Ala Leu Tyr Gly Thr Glu Glu Gln Ile Ala Val Asn Glu
                325                 330                 335 aag atc gtc cgc ggc atc ctc gaa ccg acg ggg ggt gag atc ctc acc      1056
Lys Ile Val Arg Gly Ile Leu Glu Pro Thr Gly Gly Glu Ile Leu Thr
                340                 345                 350 gaa gag gag gct gga gat aac att ctt ttc cat cac cat aag cag ctc      1104
Glu Glu Glu Ala Gly Asp Asn Ile Leu Phe His His His Lys Gln Leu
                355                 360                 365 atg aac ggc gag atg aca ttg gag gaa atg aat atc tac cag tgg cgc      1152
Met Asn Gly Glu Met Thr Leu Glu Glu Met Asn Ile Tyr Gln Trp Arg
        370                 375                 380 gga gca ggt ggc ggt gct tgc tgg ttt gca ccg gtt gct cag gtc aag      1200
Gly Ala Gly Gly Gly Ala Cys Trp Phe Ala Pro Val Ala Gln Val Lys
385                 390                 395                 400 ggg cat gag gca gag cag cag gtc aag ctt gct cag aag gtg ctt gca      1248
Gly His Glu Ala Glu Gln Gln Val Lys Leu Ala Gln Lys Val Leu Ala
                405                 410                 415 aag cat ggg ttc gat tac acg gcg ggc ttt gcg att ggt tgg cgc gat      1296
Lys His Gly Phe Asp Tyr Thr Ala Gly Phe Ala Ile Gly Trp Arg Asp
                420                 425                 430 ctt cac cat gtg atc gat gtg ctg tac gac cgt agc aat gcc gac gag      1344
Leu His His Val Ile Asp Val Leu Tyr Asp Arg Ser Asn Ala Asp Glu
                435                 440                 445 aaa aag cgc gct tac gct tgc ttt gat gaa ttg atc gac gtc ttt gcg      1392
Lys Lys Arg Ala Tyr Ala Cys Phe Asp Glu Leu Ile Asp Val Phe Ala
        450                 455                 460 gcc gaa ggc ttt gca agt tac agg acc aat att gcc ttt atg gac aaa      1440
Ala Glu Gly Phe Ala Ser Tyr Arg Thr Asn Ile Ala Phe Met Asp Lys
465                 470                 475                 480 gtc gcc tct aag ttc ggc gct gag aat aag agg gtc aat cag aag atc      1488
Val Ala Ser Lys Phe Gly Ala Glu Asn Lys Arg Val Asn Gln Lys Ile
                485                 490                 495 aag gct gcc ctt gat cca aac ggc atc atc gct ccc ggc aag tcg ggc      1536
Lys Ala Ala Leu Asp Pro Asn Gly Ile Ile Ala Pro Gly Lys Ser Gly
                500                 505                 510 att cat ctt ccc aaa taa                                               1554
Ile His Leu Pro Lys
        515

<210> SEQ ID NO 16
<211> LENGTH: 517
<212> TYPE: PRT
<213> ORGANISM: not required under old rule

<400> SEQUENCE: 16

Met Glu Ser Thr Val Val Leu Pro Glu Gly Val Thr Pro Glu Gln Phe
1               5                   10                  15

Thr Lys Ala Ile Ser Glu Phe Arg Gln Val Leu Gly Glu Asp Ser Val
                20                  25                  30

Leu Val Thr Ala Glu Arg Val Pro Tyr Thr Lys Leu Leu Ile Pro
            35                  40                  45

Thr Gln Asp Asp Ala Gln Tyr Thr Pro Ala Gly Ala Leu Thr Pro Ser
        50                  55                  60

Ser Val Glu Gln Val Gln Lys Val Met Gly Ile Cys Asn Lys Tyr Lys
65                  70                  75                  80

Ile Pro Val Trp Pro Ile Ser Thr Gly Arg Asn Trp Gly Tyr Gly Ser
                85                  90                  95
```

```
Ala Ser Pro Ala Thr Pro Gly Gln Met Ile Leu Asp Leu Arg Lys Met
            100                 105                 110
Asn Lys Ile Ile Glu Ile Asp Val Glu Gly Cys Thr Ala Leu Leu Glu
        115                 120                 125
Pro Gly Val Thr Tyr Gln Gln Leu His Asp Tyr Ile Lys Glu His Asn
    130                 135                 140
Leu Pro Leu Met Leu Asp Val Pro Thr Ile Gly Pro Met Val Gly Pro
145                 150                 155                 160
Val Gly Asn Thr Leu Asp Arg Gly Val Gly Tyr Thr Pro Tyr Gly Glu
                165                 170                 175
His Phe Met Met Gln Cys Gly Met Glu Val Val Met Ala Asp Gly Glu
            180                 185                 190
Ile Leu Arg Thr Gly Met Gly Ser Val Pro Lys Ala Lys Thr Trp Gln
        195                 200                 205
Ala Phe Lys Trp Gly Tyr Gly Pro Tyr Leu Asp Gly Ile Phe Thr Gln
    210                 215                 220
Ser Asn Phe Gly Val Val Thr Lys Leu Gly Ile Trp Leu Met Pro Lys
225                 230                 235                 240
Pro Pro Val Ile Lys Ser Phe Met Ile Arg Tyr Pro Asn Glu Ala Asp
                245                 250                 255
Val Val Lys Ala Ile Asp Ala Phe Arg Pro Leu Arg Ile Thr Gln Leu
            260                 265                 270
Ile Pro Asn Val Val Leu Phe Met His Gly Met Tyr Glu Thr Ala Ile
        275                 280                 285
Cys Arg Thr Arg Ala Glu Val Thr Ser Asp Pro Gly Pro Ile Ser Glu
    290                 295                 300
Ala Asp Ala Arg Lys Ala Phe Lys Glu Leu Gly Val Gly Tyr Trp Asn
305                 310                 315                 320
Val Tyr Phe Ala Leu Tyr Gly Thr Glu Glu Gln Ile Ala Val Asn Glu
                325                 330                 335
Lys Ile Val Arg Gly Ile Leu Glu Pro Thr Gly Gly Glu Ile Leu Thr
            340                 345                 350
Glu Glu Glu Ala Gly Asp Asn Ile Leu Phe His His Lys Gln Leu
        355                 360                 365
Met Asn Gly Glu Met Thr Leu Glu Glu Met Asn Ile Tyr Gln Trp Arg
    370                 375                 380
Gly Ala Gly Gly Gly Ala Cys Trp Phe Ala Pro Val Ala Gln Val Lys
385                 390                 395                 400
Gly His Glu Ala Glu Gln Gln Val Lys Leu Ala Gln Lys Val Leu Ala
                405                 410                 415
Lys His Gly Phe Asp Tyr Thr Ala Gly Phe Ala Ile Gly Trp Arg Asp
            420                 425                 430
Leu His His Val Ile Asp Val Leu Tyr Asp Arg Ser Asn Ala Asp Glu
        435                 440                 445
Lys Lys Arg Ala Tyr Ala Cys Phe Asp Glu Leu Ile Asp Val Phe Ala
    450                 455                 460
Ala Glu Gly Phe Ala Ser Tyr Arg Thr Asn Ile Ala Phe Met Asp Lys
465                 470                 475                 480
Val Ala Ser Lys Phe Gly Ala Glu Asn Lys Arg Val Asn Gln Lys Ile
                485                 490                 495
Lys Ala Ala Leu Asp Pro Asn Gly Ile Ile Ala Pro Gly Lys Ser Gly
            500                 505                 510
```

Ile His Leu Pro Lys
      515

<210> SEQ ID NO 17
<211> LENGTH: 861
<212> TYPE: DNA
<213> ORGANISM: not required under old rule
<220> FEATURE:
<221> NAME/KEY: CDS
<222> LOCATION: (1)..(858)
<223> OTHER INFORMATION: gene = "ORF2"

<400> SEQUENCE: 17

```
atg att gca atc act gcg ggc acc gga agt ctt ggt cgg gct atc gtt      48
Met Ile Ala Ile Thr Ala Gly Thr Gly Ser Leu Gly Arg Ala Ile Val
 1               5                  10                  15 gag cga cta ggg gac tgc ggt ctt atc ggt caa gtt cga ttg acg gct      96
Glu Arg Leu Gly Asp Cys Gly Leu Ile Gly Gln Val Arg Leu Thr Ala
             20                  25                  30 cgc gat cct aaa agg ctt cgt gcc gct gcc gag gaa ggg ttt cag gtc     144
Arg Asp Pro Lys Arg Leu Arg Ala Ala Ala Glu Glu Gly Phe Gln Val
         35                  40                  45 gct aag gcg gat tac gcc gat att ggg agt ctt gac cag gca tta cag     192
Ala Lys Ala Asp Tyr Ala Asp Ile Gly Ser Leu Asp Gln Ala Leu Gln
     50                  55                  60 ggg gta gac gta tta ctc ctg att tct ggt act gca ccc aat gaa ata     240
Gly Val Asp Val Leu Leu Leu Ile Ser Gly Thr Ala Pro Asn Glu Ile
 65                  70                  75                  80 agg atc caa cag cat aag tcg gtc atc gac gcg gca aaa cga aac ggc     288
Arg Ile Gln Gln His Lys Ser Val Ile Asp Ala Ala Lys Arg Asn Gly
                 85                  90                  95 gtg tcg cgt att gtg tat acc agc ttc ata aat cca agt act cgc agc     336
Val Ser Arg Ile Val Tyr Thr Ser Phe Ile Asn Pro Ser Thr Arg Ser
            100                 105                 110 agg tct att tgg gcc tcc att cat cgt gaa act gag act tac ctc agg     384
Arg Ser Ile Trp Ala Ser Ile His Arg Glu Thr Glu Thr Tyr Leu Arg
        115                 120                 125 cag tct ggg gtg aag ttt acg att gtc cga aat aat cag tat gcg tct     432
Gln Ser Gly Val Lys Phe Thr Ile Val Arg Asn Asn Gln Tyr Ala Ser
    130                 135                 140 aac ctg gat ctg ttg ctg ctg agg gct caa gac agc gga ata ttt gcc     480
Asn Leu Asp Leu Leu Leu Leu Arg Ala Gln Asp Ser Gly Ile Phe Ala
145                 150                 155                 160 att ccc ggg gcg aag ggg cgg gtg gcg tac gtc tct cat cgc gac gtt     528
Ile Pro Gly Ala Lys Gly Arg Val Ala Tyr Val Ser His Arg Asp Val
                165                 170                 175 gcc gct gcc atc tgt agt gtc ctg acg acc gcc gga cac gat aac agg     576
Ala Ala Ala Ile Cys Ser Val Leu Thr Thr Ala Gly His Asp Asn Arg
            180                 185                 190 atc tac cag ctc aca ggc tct gag gct ctc aat ggg ctc gag atc gcg     624
Ile Tyr Gln Leu Thr Gly Ser Glu Ala Leu Asn Gly Leu Glu Ile Ala
        195                 200                 205 gag att ctt ggt ggg gtg ctc ggg cgt cca gtg cgc gcg atg gat gcc     672
Glu Ile Leu Gly Gly Val Leu Gly Arg Pro Val Arg Ala Met Asp Ala
    210                 215                 220 tcg cct gac gag ttt gct gcc agc ttt cgc gag gct gga ttc cct gag     720
Ser Pro Asp Glu Phe Ala Ala Ser Phe Arg Glu Ala Gly Phe Pro Glu
225                 230                 235                 240 ttt atg gtt gaa ggc cta cta agc att tat gcc gct tca ggt gct ggg     768
Phe Met Val Glu Gly Leu Leu Ser Ile Tyr Ala Ala Ser Gly Ala Gly
                245                 250                 255
```

```
gag tac caa tcc gtc agt cct gat gtt ggg ttg ttg acg gga cga cgt    816
Glu Tyr Gln Ser Val Ser Pro Asp Val Gly Leu Leu Thr Gly Arg Arg
            260                 265                 270 gcc gaa tcg atg cga act tac ata cag cgt cta gtt tgg cct tga        861
Ala Glu Ser Met Arg Thr Tyr Ile Gln Arg Leu Val Trp Pro
        275                 280                 285

<210> SEQ ID NO 18
<211> LENGTH: 286
<212> TYPE: PRT
<213> ORGANISM: not required under old rule

<400> SEQUENCE: 18

Met Ile Ala Ile Thr Ala Gly Thr Gly Ser Leu Gly Arg Ala Ile Val
 1               5                  10                  15

Glu Arg Leu Gly Asp Cys Gly Leu Ile Gly Gln Val Arg Leu Thr Ala
            20                  25                  30

Arg Asp Pro Lys Arg Leu Arg Ala Ala Glu Glu Gly Phe Gln Val
        35                  40                  45

Ala Lys Ala Asp Tyr Ala Asp Ile Gly Ser Leu Asp Gln Ala Leu Gln
 50                  55                  60

Gly Val Asp Val Leu Leu Ile Ser Gly Thr Ala Pro Asn Glu Ile
 65                  70                  75                  80

Arg Ile Gln Gln His Lys Ser Val Ile Asp Ala Ala Lys Arg Asn Gly
                85                  90                  95

Val Ser Arg Ile Val Tyr Thr Ser Phe Ile Asn Pro Ser Thr Arg Ser
            100                 105                 110

Arg Ser Ile Trp Ala Ser Ile His Arg Glu Thr Glu Thr Tyr Leu Arg
        115                 120                 125

Gln Ser Gly Val Lys Phe Thr Ile Val Arg Asn Asn Gln Tyr Ala Ser
    130                 135                 140

Asn Leu Asp Leu Leu Leu Arg Ala Gln Asp Ser Gly Ile Phe Ala
145                 150                 155                 160

Ile Pro Gly Ala Lys Gly Arg Val Ala Tyr Val Ser His Arg Asp Val
                165                 170                 175

Ala Ala Ala Ile Cys Ser Val Leu Thr Thr Ala Gly His Asp Asn Arg
            180                 185                 190

Ile Tyr Gln Leu Thr Gly Ser Glu Ala Leu Asn Gly Leu Glu Ile Ala
        195                 200                 205

Glu Ile Leu Gly Gly Val Leu Gly Arg Pro Val Arg Ala Met Asp Ala
    210                 215                 220

Ser Pro Asp Glu Phe Ala Ala Ser Phe Arg Glu Ala Gly Phe Pro Glu
225                 230                 235                 240

Phe Met Val Glu Gly Leu Leu Ser Ile Tyr Ala Ala Ser Gly Ala Gly
                245                 250                 255

Glu Tyr Gln Ser Val Ser Pro Asp Val Gly Leu Leu Thr Gly Arg Arg
            260                 265                 270

Ala Glu Ser Met Arg Thr Tyr Ile Gln Arg Leu Val Trp Pro
        275                 280                 285

<210> SEQ ID NO 19
<211> LENGTH: 1011
<212> TYPE: DNA
<213> ORGANISM: not required under old rule
<220> FEATURE:
<221> NAME/KEY: CDS
<222> LOCATION: (1)..(1008)
<223> OTHER INFORMATION: product = "Alkohol-Dehydrogenase" / gene =
```

"adh"

<400> SEQUENCE: 19

| | | | | | | | | | | | | | | | | |
|---|---|---|---|---|---|---|---|---|---|---|---|---|---|---|---|---|
| atg | aag | gct | tat | gag | ctt | cac | aag | att | tcg | gaa | cag | gta | gag | gtc | agg | 48 |
| Met | Lys | Ala | Tyr | Glu | Leu | His | Lys | Ile | Ser | Glu | Gln | Val | Glu | Val | Arg | |
| 1 | | | | 5 | | | | | 10 | | | | | 15 | | |
| ctc | cag | cca | act | cgg | ccc | cgc | ccg | cag | ttg | aat | cat | ggc | gag | gtc | ctc | 96 |
| Leu | Gln | Pro | Thr | Arg | Pro | Arg | Pro | Gln | Leu | Asn | His | Gly | Glu | Val | Leu | |
| | | | 20 | | | | | 25 | | | | | 30 | | | |
| atc | agg | gtc | cat | gca | gcc | tcg | ctc | aac | ttt | cgc | gat | ttg | atg | atc | ttg | 144 |
| Ile | Arg | Val | His | Ala | Ala | Ser | Leu | Asn | Phe | Arg | Asp | Leu | Met | Ile | Leu | |
| | | 35 | | | | | 40 | | | | | 45 | | | | |
| gcc | ggt | cgc | tat | ccg | ggt | caa | atg | aaa | ccc | gat | gtg | atc | ccg | ctg | tcc | 192 |
| Ala | Gly | Arg | Tyr | Pro | Gly | Gln | Met | Lys | Pro | Asp | Val | Ile | Pro | Leu | Ser | |
| | 50 | | | | | 55 | | | | | 60 | | | | | |
| gat | ggt | gct | ggc | gag | att | gtg | gag | gtc | ggg | cct | ggc | gta | tct | tcg | gag | 240 |
| Asp | Gly | Ala | Gly | Glu | Ile | Val | Glu | Val | Gly | Pro | Gly | Val | Ser | Ser | Glu | |
| 65 | | | | | 70 | | | | | 75 | | | | | 80 | |
| gtg | cag | ggt | cag | cgc | gta | gcc | agc | acc | ttt | ttc | cct | aac | tgg | cgg | gcc | 288 |
| Val | Gln | Gly | Gln | Arg | Val | Ala | Ser | Thr | Phe | Phe | Pro | Asn | Trp | Arg | Ala | |
| | | | | 85 | | | | | 90 | | | | | 95 | | |
| gga | aag | att | acc | gag | ccg | gct | att | gag | gtg | tcg | ttg | ggc | ttc | ggt | atg | 336 |
| Gly | Lys | Ile | Thr | Glu | Pro | Ala | Ile | Glu | Val | Ser | Leu | Gly | Phe | Gly | Met | |
| | | | | 100 | | | | | 105 | | | | | 110 | | |
| gac | ggg | atg | ctc | gcg | gaa | tac | gtt | gct | ctg | ccc | tat | gag | gca | acg | ata | 384 |
| Asp | Gly | Met | Leu | Ala | Glu | Tyr | Val | Ala | Leu | Pro | Tyr | Glu | Ala | Thr | Ile | |
| | | | 115 | | | | | 120 | | | | | 125 | | | |
| ccg | ata | ccg | gag | cac | ctg | tcg | tac | gag | gag | gct | gca | aca | ttg | cct | tgc | 432 |
| Pro | Ile | Pro | Glu | His | Leu | Ser | Tyr | Glu | Glu | Ala | Ala | Thr | Leu | Pro | Cys | |
| | 130 | | | | | 135 | | | | | 140 | | | | | |
| gcg | gcg | cta | acc | gct | tgg | aat | gcg | ttg | acc | gaa | gtg | ggg | cgt | gtc | aag | 480 |
| Ala | Ala | Leu | Thr | Ala | Trp | Asn | Ala | Leu | Thr | Glu | Val | Gly | Arg | Val | Lys | |
| 145 | | | | | 150 | | | | | 155 | | | | | 160 | |
| gcc | ggt | gat | acg | gtc | ttg | ttg | ctt | ggc | act | ggc | ggt | gtc | tcg | atg | ttc | 528 |
| Ala | Gly | Asp | Thr | Val | Leu | Leu | Leu | Gly | Thr | Gly | Gly | Val | Ser | Met | Phe | |
| | | | 165 | | | | | 170 | | | | | 175 | | | |
| gcg | ttg | cag | ttc | gcc | aag | ctc | ttg | ggg | gcg | acg | gtc | att | cac | acc | tcg | 576 |
| Ala | Leu | Gln | Phe | Ala | Lys | Leu | Leu | Gly | Ala | Thr | Val | Ile | His | Thr | Ser | |
| | | 180 | | | | | 185 | | | | | 190 | | | | |
| agc | agt | gaa | caa | aag | ctg | gag | agg | gtg | aaa | gcg | atg | ggg | gct | gat | cat | 624 |
| Ser | Ser | Glu | Gln | Lys | Leu | Glu | Arg | Val | Lys | Ala | Met | Gly | Ala | Asp | His | |
| | 195 | | | | | 200 | | | | | 205 | | | | | |
| ctg | atc | aac | tac | cgc | aat | tcg | cca | ggg | tgg | gac | cgt | act | gtc | ctg | gat | 672 |
| Leu | Ile | Asn | Tyr | Arg | Asn | Ser | Pro | Gly | Trp | Asp | Arg | Thr | Val | Leu | Asp | |
| 210 | | | | | 215 | | | | | 220 | | | | | | |
| ctc | acc | gcg | ggg | cga | ggg | gtt | gac | ctg | gta | gtc | gag | gta | ggg | ggg | gcg | 720 |
| Leu | Thr | Ala | Gly | Arg | Gly | Val | Asp | Leu | Val | Val | Glu | Val | Gly | Gly | Ala | |
| 225 | | | | 230 | | | | | 235 | | | | | 240 | | |
| ggg | acc | ttg | gag | cgc | tca | ctt | cgt | gcg | gtc | aag | gta | ggc | ggt | att | gtc | 768 |
| Gly | Thr | Leu | Glu | Arg | Ser | Leu | Arg | Ala | Val | Lys | Val | Gly | Gly | Ile | Val | |
| | | | | 245 | | | | | 250 | | | | | 255 | | |
| gcc | acg | att | ggg | cta | gtg | gct | ggc | gtt | ggc | ccg | att | gac | cca | ttg | ccg | 816 |
| Ala | Thr | Ile | Gly | Leu | Val | Ala | Gly | Val | Gly | Pro | Ile | Asp | Pro | Leu | Pro | |
| | | | 260 | | | | | 265 | | | | | 270 | | | |
| ctt | atc | tcc | agg | gct | att | cag | ctc | tcg | ggc | gtc | tat | gtc | ggt | tcc | cgg | 864 |
| Leu | Ile | Ser | Arg | Ala | Ile | Gln | Leu | Ser | Gly | Val | Tyr | Val | Gly | Ser | Arg | |
| | | 275 | | | | | 280 | | | | | 285 | | | | |
| gaa | atg | ttt | ctc | tca | atg | aac | aaa | gcc | att | gca | tca | gcc | gaa | atc | aag | 912 |
| Glu | Met | Phe | Leu | Ser | Met | Asn | Lys | Ala | Ile | Ala | Ser | Ala | Glu | Ile | Lys | |
| | 290 | | | | | 295 | | | | | 300 | | | | | |

```
cca gtg atc gat tgc tgc ttc ccc atc gac gag gtt gga gat gct tat      960
Pro Val Ile Asp Cys Cys Phe Pro Ile Asp Glu Val Gly Asp Ala Tyr
305                 310                 315                 320 gag tac atg cgt agc ggc aat cac ctt ggc aaa gta gtt atc acg atc     1008
Glu Tyr Met Arg Ser Gly Asn His Leu Gly Lys Val Val Ile Thr Ile
                325                 330                 335 taa                                                                 1011
```

<210> SEQ ID NO 20
<211> LENGTH: 336
<212> TYPE: PRT
<213> ORGANISM: not required under old rule

<400> SEQUENCE: 20

```
Met Lys Ala Tyr Glu Leu His Lys Ile Ser Glu Gln Val Glu Val Arg
  1               5                  10                  15

Leu Gln Pro Thr Arg Pro Arg Pro Gln Leu Asn His Gly Glu Val Leu
                 20                  25                  30

Ile Arg Val His Ala Ala Ser Leu Asn Phe Arg Asp Leu Met Ile Leu
             35                  40                  45

Ala Gly Arg Tyr Pro Gly Gln Met Lys Pro Asp Val Ile Pro Leu Ser
         50                  55                  60

Asp Gly Ala Gly Glu Ile Val Glu Val Gly Pro Gly Val Ser Ser Glu
 65                  70                  75                  80

Val Gln Gly Gln Arg Val Ala Ser Thr Phe Phe Pro Asn Trp Arg Ala
                 85                  90                  95

Gly Lys Ile Thr Glu Pro Ala Ile Glu Val Ser Leu Gly Phe Gly Met
            100                 105                 110

Asp Gly Met Leu Ala Glu Tyr Val Ala Leu Pro Tyr Glu Ala Thr Ile
        115                 120                 125

Pro Ile Pro Glu His Leu Ser Tyr Glu Glu Ala Ala Thr Leu Pro Cys
    130                 135                 140

Ala Ala Leu Thr Ala Trp Asn Ala Leu Thr Glu Val Gly Arg Val Lys
145                 150                 155                 160

Ala Gly Asp Thr Val Leu Leu Gly Thr Gly Gly Val Ser Met Phe
                165                 170                 175

Ala Leu Gln Phe Ala Lys Leu Leu Gly Ala Thr Val Ile His Thr Ser
            180                 185                 190

Ser Ser Glu Gln Lys Leu Glu Arg Val Lys Ala Met Gly Ala Asp His
        195                 200                 205

Leu Ile Asn Tyr Arg Asn Ser Pro Gly Trp Asp Arg Thr Val Leu Asp
    210                 215                 220

Leu Thr Ala Gly Arg Gly Val Asp Leu Val Val Glu Val Gly Gly Ala
225                 230                 235                 240

Gly Thr Leu Glu Arg Ser Leu Arg Ala Val Lys Val Gly Gly Ile Val
                245                 250                 255

Ala Thr Ile Gly Leu Val Ala Gly Val Gly Pro Ile Asp Pro Leu Pro
            260                 265                 270

Leu Ile Ser Arg Ala Ile Gln Leu Ser Gly Val Tyr Val Gly Ser Arg
        275                 280                 285

Glu Met Phe Leu Ser Met Asn Lys Ala Ile Ala Ser Ala Glu Ile Lys
    290                 295                 300

Pro Val Ile Asp Cys Cys Phe Pro Ile Asp Glu Val Gly Asp Ala Tyr
305                 310                 315                 320
```

Glu Tyr Met Arg Ser Gly Asn His Leu Gly Lys Val Val Ile Thr Ile
            325                 330                 335

<210> SEQ ID NO 21
<211> LENGTH: 1518
<212> TYPE: DNA
<213> ORGANISM: not required under old rule

<400> SEQUENCE: 21

| | | | | |
|---|---|---|---|---|
| tcaccgtcgt | gatcgggatt | ggaaattcgt | gcgaggacag | cggccacgta | ccggcgccct |   60 |
| gaagggctgg | aaggttggag | tttcgttaag | gtctggtacc | cagcagccat | ggagagcggc |  120 |
| ccttagccgg | aatggcagct | tgatggttgc | cacgggacca | gactggatgt | cttgagtgtc |  180 |
| gagaattacc | agatcgctgc | gattttcatc | gaggcgacca | accacggtca | gcaagtaccc |  240 |
| gtcaccttcg | gcggcggtcg | gacttctagg | gacgaaggcc | ggctcctggg | ccgccgaggc |  300 |
| ttcgccggag | taccagaggt | cgtagtcacc | tcggtggttg | tcccagatgc | cgagtgagtt |  360 |
| gtacgcgaat | atcttctcgg | cctgctgatg | cgcaagtggt | ttgcgtggat | cgtccacccc |  420 |
| cataaagcca | tagcggttgc | attgcagggc | gaacgaagaa | tccatgattg | gcatttccgc |  480 |
| aaagaaatcg | tgtagccggg | ttcgcttgat | ctcgtcgctg | ctgctatcga | ggtcaatttc |  540 |
| ccaacgagtc | aggcgtggta | cggctttctc | aggggcgaag | ggttggtttt | gtgagttggg |  600 |
| gaagggaac | ggcaggattt | cactttccat | aaggtcgata | taaatcttgg | ttccgacttc |  660 |
| ccaagcattc | acaacatgaa | atacccagag | cgccggtgcc | ttgagccagc | gaatcagact |  720 |
| gccctggcgc | ggcgcgagta | cgccaatgta | gctgcccagt | tccggctccc | acatataaat |  780 |
| tggctgtttc | gccttgaggc | gggacaggct | gttggtggcc | ggcataattg | ggaaaatgga |  840 |
| ccaatttcgg | gtaatggcaa | agtcgtgcat | gaatgcgcca | tagggctgct | caaaccaagt |  900 |
| ttcatgtgtc | accttgccgt | gcttgtcgac | aatgtaatag | gccatgtctg | gagttgcttc |  960 |
| gcccttagct | gccgaaccga | gaacaacaa | gtcacccgtt | tccgggtcat | attttggatg | 1020 |
| ggcggtgtgg | gtttggctgg | taacttggcc | gtcgtagtcg | aagtgtccgc | gagtttcaag | 1080 |
| tgtacgagga | tccagttcgt | acggtaggcc | gtcttccttc | accgccagca | ccttgccgtg | 1140 |
| atggctaatg | atgcttgtat | tggcaacggt | gcggtctagt | cctttttacac | tggtgtcgtc | 1200 |
| ggtatagggg | tttctgtaca | tgccaaatag | cgattttcgc | gctagtcgtt | cggccgtgaa | 1260 |
| tcgagcggtt | ttaacccagc | gactgatgaa | gtcgacatga | ccatcttcga | agtggaaggc | 1320 |
| agaggccatt | ccatctccat | ctatgaaggt | gtggaatttt | tgtggggtaa | cttgaggctc | 1380 |
| tggcgtatta | cggtagaacg | ttccatttat | tgattttggg | atttcgccgt | caacctctag | 1440 |
| atcgaacaag | tctgcctcta | tacgggtggg | gagaagtgtt | cctactaatt | gcgggtcgtt | 1500 |
| gcggttgaat | ctcgccat | | | | 1518 |

<210> SEQ ID NO 22
<211> LENGTH: 505
<212> TYPE: PRT
<213> ORGANISM: not required under old rule

<400> SEQUENCE: 22

Met Ala Arg Phe Asn Arg Asn Asp Pro Gln Leu Val Gly Thr Leu Leu
  1               5                  10                  15

Pro Thr Arg Ile Glu Ala Asp Leu Phe Asp Leu Glu Val Asp Gly Glu
             20                  25                  30

Ile Pro Lys Ser Ile Asn Gly Thr Phe Tyr Arg Asn Thr Pro Glu Pro
         35                  40                  45

-continued

```
Gln Val Thr Pro Gln Lys Phe His Thr Phe Ile Asp Gly Asp Gly Met
     50                  55                  60

Ala Ser Ala Phe His Phe Glu Asp Gly His Val Asp Phe Ile Ser Arg
 65                  70                  75                  80

Trp Val Lys Thr Ala Arg Phe Thr Ala Glu Arg Leu Ala Arg Lys Ser
                 85                  90                  95

Leu Phe Gly Met Tyr Arg Asn Pro Tyr Thr Asp Asp Thr Ser Val Lys
                100                 105                 110

Gly Leu Asp Arg Thr Val Ala Asn Thr Ser Ile Ile Ser His His Gly
             115                 120                 125

Lys Val Leu Ala Val Lys Glu Asp Gly Leu Pro Tyr Glu Leu Asp Pro
         130                 135                 140

Arg Thr Leu Glu Thr Arg Gly His Phe Asp Tyr Asp Gly Gln Val Thr
145                 150                 155                 160

Ser Gln Thr His Thr Ala His Pro Lys Tyr Asp Pro Glu Thr Gly Asp
                165                 170                 175

Leu Leu Phe Phe Gly Ser Ala Ala Lys Gly Glu Ala Thr Pro Asp Met
            180                 185                 190

Ala Tyr Tyr Ile Val Asp Lys His Gly Lys Val Thr His Glu Thr Trp
        195                 200                 205

Phe Glu Gln Pro Tyr Gly Ala Phe Met His Asp Phe Ala Ile Thr Arg
    210                 215                 220

Asn Trp Ser Ile Phe Pro Ile Met Pro Ala Thr Asn Ser Leu Ser Arg
225                 230                 235                 240

Leu Lys Ala Lys Gln Pro Ile Tyr Met Trp Glu Pro Glu Leu Gly Ser
                245                 250                 255

Tyr Ile Gly Val Leu Ala Pro Arg Gln Gly Ser Leu Ile Arg Trp Leu
            260                 265                 270

Lys Ala Pro Ala Leu Trp Val Phe His Val Val Asn Ala Trp Glu Val
        275                 280                 285

Gly Thr Lys Ile Tyr Ile Asp Leu Met Glu Ser Glu Ile Leu Pro Phe
    290                 295                 300

Pro Phe Pro Asn Ser Gln Asn Gln Pro Phe Ala Pro Glu Lys Ala Val
305                 310                 315                 320

Pro Arg Leu Thr Arg Trp Glu Ile Asp Leu Asp Ser Ser Ser Asp Glu
                325                 330                 335

Ile Lys Arg Thr Arg Leu His Asp Phe Phe Ala Glu Met Pro Ile Met
            340                 345                 350

Asp Ser Ser Phe Ala Leu Gln Cys Asn Arg Tyr Gly Phe Met Gly Val
        355                 360                 365

Asp Asp Pro Arg Lys Pro Leu Ala His Gln Gln Ala Glu Lys Ile Phe
    370                 375                 380

Ala Tyr Asn Ser Leu Gly Ile Trp Asp Asn His Arg Gly Asp Tyr Asp
385                 390                 395                 400

Leu Trp Tyr Ser Gly Glu Ala Ser Ala Gln Glu Pro Ala Phe Val
                405                 410                 415

Pro Arg Ser Pro Thr Ala Ala Glu Gly Asp Gly Tyr Leu Leu Thr Val
            420                 425                 430

Val Gly Arg Leu Asp Glu Asn Arg Ser Asp Leu Val Ile Leu Asp Thr
        435                 440                 445

Gln Asp Ile Gln Ser Gly Pro Val Ala Thr Ile Lys Leu Pro Phe Arg
    450                 455                 460
```

| | | | | | | | | | | | | | | | |
|---|---|---|---|---|---|---|---|---|---|---|---|---|---|---|---|
|Leu|Arg|Ala|Ala|Leu|His|Gly|Cys|Trp|Val|Pro|Asp|Leu|Asn|Glu|Thr|
|465| | | |470| | | |475| | | |480| | | |

Pro Thr Phe Gln Pro Phe Arg Ala Pro Val Arg Gly Arg Cys Pro Arg
               485               490               495

Thr Asn Phe Gln Ser Arg Ser Arg Arg
               500               505

<210> SEQ ID NO 23
<211> LENGTH: 951
<212> TYPE: DNA
<213> ORGANISM: not required under old rule
<220> FEATURE:
<221> NAME/KEY: CDS
<222> LOCATION: (1)..(948)
<223> OTHER INFORMATION: gene = "ORF3"

<400> SEQUENCE: 23

```
atg aca act att cgg tgg cgg cgt atg tcc att cac tct gag ggg atc      48
Met Thr Thr Ile Arg Trp Arg Arg Met Ser Ile His Ser Glu Gly Ile
  1               5                  10                  15 act ctc gcg gat tcg ccg ctg cat tgg gcg cat acc ctg aat gga tca      96
Thr Leu Ala Asp Ser Pro Leu His Trp Ala His Thr Leu Asn Gly Ser
             20                  25                  30 atg cgt act cat ttc gaa gtc cag cgt ctt gag cgg ggt aga ggt gcc     144
Met Arg Thr His Phe Glu Val Gln Arg Leu Glu Arg Gly Arg Gly Ala
         35                  40                  45 tcc ctt gcc cga tct aga ttt ggc gcg ggt gag ctg tac agt gcc att     192
Ser Leu Ala Arg Ser Arg Phe Gly Ala Gly Glu Leu Tyr Ser Ala Ile
     50                  55                  60 gca cca agc cag gta ctt cgc cac ttc aac gac cag cga aat gct gat     240
Ala Pro Ser Gln Val Leu Arg His Phe Asn Asp Gln Arg Asn Ala Asp
 65                  70                  75                  80 gag gct gag cac agc tat ttg att cag ata cga agt ggc gct ttg ggc     288
Glu Ala Glu His Ser Tyr Leu Ile Gln Ile Arg Ser Gly Ala Leu Gly
                 85                  90                  95 gtt gca tcc ggc gga aga aag gtg atc ttg gca aat ggt gat tgc tcc     336
Val Ala Ser Gly Gly Arg Lys Val Ile Leu Ala Asn Gly Asp Cys Ser
            100                 105                 110 ata gtt gat agt cgc caa gac ttc aca ctt tcc tcg aac tct tcg acc     384
Ile Val Asp Ser Arg Gln Asp Phe Thr Leu Ser Ser Asn Ser Ser Thr
        115                 120                 125 caa ggt gtc gta ata cgc ttt ccg gtg agt tgg ctg gga gcg tgg gtg     432
Gln Gly Val Val Ile Arg Phe Pro Val Ser Trp Leu Gly Ala Trp Val
    130                 135                 140 tcc aat ccg gag gat ctt atc gcc cga cga gtt gat gct gag gta ggg     480
Ser Asn Pro Glu Asp Leu Ile Ala Arg Arg Val Asp Ala Glu Val Gly
145                 150                 155                 160 tgg ggt agg gcg cta agc gca tcg gtt tct aat cta gat cca ttg cgc     528
Trp Gly Arg Ala Leu Ser Ala Ser Val Ser Asn Leu Asp Pro Leu Arg
                165                 170                 175 atc gac gat tta ggt agc aat gta aat ggc att gca gag cat gtt gct     576
Ile Asp Asp Leu Gly Ser Asn Val Asn Gly Ile Ala Glu His Val Ala
            180                 185                 190 atg tta att tca cta gca agt tct gcg gtt agt tct gaa gat ggg ggt     624
Met Leu Ile Ser Leu Ala Ser Ser Ala Val Ser Ser Glu Asp Gly Gly
        195                 200                 205 gtg gct ctt cgg aaa atg agg gaa gtg aag aga gta ctc gag cag agt     672
Val Ala Leu Arg Lys Met Arg Glu Val Lys Arg Val Leu Glu Gln Ser
    210                 215                 220 ttc gca gac gct aat ctc ggg ccg gaa agt gtt tca agt caa tta gga     720
Phe Ala Asp Ala Asn Leu Gly Pro Glu Ser Val Ser Ser Gln Leu Gly
```

```
                  225                 230                 235                 240
att tcg aaa cgc tat ttg cat tat gtc ttt gct gcg tgc ggt acg acc    768
Ile Ser Lys Arg Tyr Leu His Tyr Val Phe Ala Ala Cys Gly Thr Thr
                245                 250                 255 ttt ggt cgc gag ctg ttg gaa ata cgc ctg ggc aaa gct tat cga atg    816
Phe Gly Arg Glu Leu Leu Glu Ile Arg Leu Gly Lys Ala Tyr Arg Met
            260                 265                 270 ctc tgt gcg gcg agt gac tcg ggt gct gtg ctg aag gtg gcc atg tcc    864
Leu Cys Ala Ala Ser Asp Ser Gly Ala Val Leu Lys Val Ala Met Ser
        275                 280                 285 tca ggt ttt tcg gat tca agc cat ttc agc aag aaa ttt aag gaa aga    912
Ser Gly Phe Ser Asp Ser Ser His Phe Ser Lys Lys Phe Lys Glu Arg
    290                 295                 300 tac ggt gtt tcg cct gtc tcc ttg gtg agg cag gct tga                951
Tyr Gly Val Ser Pro Val Ser Leu Val Arg Gln Ala
305                 310                 315
```

<210> SEQ ID NO 24
<211> LENGTH: 316
<212> TYPE: PRT
<213> ORGANISM: not required under old rule

<400> SEQUENCE: 24

```
Met Thr Thr Ile Arg Trp Arg Arg Met Ser Ile His Ser Glu Gly Ile
  1               5                  10                  15

Thr Leu Ala Asp Ser Pro Leu His Trp Ala His Thr Leu Asn Gly Ser
             20                  25                  30

Met Arg Thr His Phe Glu Val Gln Arg Leu Glu Arg Gly Arg Gly Ala
         35                  40                  45

Ser Leu Ala Arg Ser Arg Phe Gly Ala Gly Glu Leu Tyr Ser Ala Ile
     50                  55                  60

Ala Pro Ser Gln Val Leu Arg His Phe Asn Asp Gln Arg Asn Ala Asp
 65                  70                  75                  80

Glu Ala Glu His Ser Tyr Leu Ile Gln Ile Arg Ser Gly Ala Leu Gly
                 85                  90                  95

Val Ala Ser Gly Gly Arg Lys Val Ile Leu Ala Asn Gly Asp Cys Ser
            100                 105                 110

Ile Val Asp Ser Arg Gln Asp Phe Thr Leu Ser Ser Asn Ser Ser Thr
        115                 120                 125

Gln Gly Val Val Ile Arg Phe Pro Val Ser Trp Leu Gly Ala Trp Val
    130                 135                 140

Ser Asn Pro Glu Asp Leu Ile Ala Arg Arg Val Asp Ala Glu Val Gly
145                 150                 155                 160

Trp Gly Arg Ala Leu Ser Ala Ser Val Ser Asn Leu Asp Pro Leu Arg
                165                 170                 175

Ile Asp Asp Leu Gly Ser Asn Val Asn Gly Ile Ala Glu His Val Ala
            180                 185                 190

Met Leu Ile Ser Leu Ala Ser Ser Ala Val Ser Ser Glu Asp Gly Gly
        195                 200                 205

Val Ala Leu Arg Lys Met Arg Glu Val Lys Arg Val Leu Glu Gln Ser
    210                 215                 220

Phe Ala Asp Ala Asn Leu Gly Pro Glu Ser Val Ser Ser Gln Leu Gly
225                 230                 235                 240

Ile Ser Lys Arg Tyr Leu His Tyr Val Phe Ala Ala Cys Gly Thr Thr
                245                 250                 255

Phe Gly Arg Glu Leu Leu Glu Ile Arg Leu Gly Lys Ala Tyr Arg Met
```

-continued

```
                260                   265                   270
Leu Cys Ala Ala Ser Asp Ser Gly Ala Val Leu Lys Val Ala Met Ser
            275                   280                   285

Ser Gly Phe Ser Asp Ser His Phe Ser Lys Lys Phe Lys Glu Arg
        290                   295                   300

Tyr Gly Val Ser Pro Val Ser Leu Val Arg Gln Ala
305                   310                   315

<210> SEQ ID NO 25
<211> LENGTH: 735
<212> TYPE: DNA
<213> ORGANISM: not required under old rule
<220> FEATURE:
<221> NAME/KEY: CDS
<222> LOCATION: (1)..(732)
<223> OTHER INFORMATION: product = "Enoyl-CoA-Hydratase" / gene = "ech"

<400> SEQUENCE: 25 atg agc cca act ctc aat cga gag atg gtc gag gtt ctg gag gtg ctg      48
Met Ser Pro Thr Leu Asn Arg Glu Met Val Glu Val Leu Glu Val Leu
  1               5                  10                  15 gag cag gac gca gat gct cgc gtg ctt gtt ctg act ggt gca ggc gaa      96
Glu Gln Asp Ala Asp Ala Arg Val Leu Val Leu Thr Gly Ala Gly Glu
                 20                  25                  30 tcc tgg acc gcg ggc atg gac ctg aag gag tat ttc cgc gag acc gat     144
Ser Trp Thr Ala Gly Met Asp Leu Lys Glu Tyr Phe Arg Glu Thr Asp
             35                  40                  45 gct ggc ccc gaa att ctg caa gag aag att cgt cgc gaa gcg tcg acc     192
Ala Gly Pro Glu Ile Leu Gln Glu Lys Ile Arg Arg Glu Ala Ser Thr
         50                  55                  60 tgg cag tgg aag ctc ctg cgg atg tac acc aag ccg acc atc gcg atg     240
Trp Gln Trp Lys Leu Leu Arg Met Tyr Thr Lys Pro Thr Ile Ala Met
 65                  70                  75                  80 gtc aat ggc tgg tgc ttc ggc ggc ggc ttc agc ccg ctg gtg gcc tgt     288
Val Asn Gly Trp Cys Phe Gly Gly Gly Phe Ser Pro Leu Val Ala Cys
                 85                  90                  95 gat ctg gcc atc tgt gcc gac gag gcc acc ttt ggc ctg tcc gag atc     336
Asp Leu Ala Ile Cys Ala Asp Glu Ala Thr Phe Gly Leu Ser Glu Ile
            100                 105                 110 aac tgg ggc atc ccg ccg ggc aac ctg gtg agt aag gct atg gcc gac     384
Asn Trp Gly Ile Pro Pro Gly Asn Leu Val Ser Lys Ala Met Ala Asp
        115                 120                 125 acc gtg ggt cac cgc gag tcc ctt tac tac atc atg act ggc aag aca     432
Thr Val Gly His Arg Glu Ser Leu Tyr Tyr Ile Met Thr Gly Lys Thr
    130                 135                 140 ttt ggc ggt cag cag gcc gcc aag atg ggg ctt gtg aac cag agt gtt     480
Phe Gly Gly Gln Gln Ala Ala Lys Met Gly Leu Val Asn Gln Ser Val
145                 150                 155                 160 ccg ctg gcc gag ctg cgc agt gtc act gta gag ctg gct cag aac ctg     528
Pro Leu Ala Glu Leu Arg Ser Val Thr Val Glu Leu Ala Gln Asn Leu
                165                 170                 175 ctg gac aag aac ccc gta gtg ctc cgt gcc gcc aaa ata ggc ttc aag     576
Leu Asp Lys Asn Pro Val Val Leu Arg Ala Ala Lys Ile Gly Phe Lys
            180                 185                 190 cgt tgc cgc gag ctg act tgg gag cag aac gag gac tac ctg tac gcc     624
Arg Cys Arg Glu Leu Thr Trp Glu Gln Asn Glu Asp Tyr Leu Tyr Ala
        195                 200                 205 aag ctc gac caa tcc cgt ttg ctc gat ccg gaa ggc ggt cgc gag cag     672
Lys Leu Asp Gln Ser Arg Leu Leu Asp Pro Glu Gly Gly Arg Glu Gln
    210                 215                 220
```

```
ggc atg aag cag ttc ctt gac gag aaa agc atc aag ccg ggc ttg cag      720
Gly Met Lys Gln Phe Leu Asp Glu Lys Ser Ile Lys Pro Gly Leu Gln
225                 230                 235                 240 acc tac aag cgc tga                                                   735
Thr Tyr Lys Arg
```

<210> SEQ ID NO 26
<211> LENGTH: 244
<212> TYPE: PRT
<213> ORGANISM: not required under old rule

<400> SEQUENCE: 26

```
Met Ser Pro Thr Leu Asn Arg Glu Met Val Glu Val Leu Glu Val Leu
  1               5                  10                  15

Glu Gln Asp Ala Asp Ala Arg Val Val Leu Thr Gly Ala Gly Glu
             20                  25                  30

Ser Trp Thr Ala Gly Met Asp Leu Lys Glu Tyr Phe Arg Glu Thr Asp
         35                  40                  45

Ala Gly Pro Glu Ile Leu Gln Glu Lys Ile Arg Arg Glu Ala Ser Thr
     50                  55                  60

Trp Gln Trp Lys Leu Leu Arg Met Tyr Thr Lys Pro Thr Ile Ala Met
 65                  70                  75                  80

Val Asn Gly Trp Cys Phe Gly Gly Phe Ser Pro Leu Val Ala Cys
                 85                  90                  95

Asp Leu Ala Ile Cys Ala Asp Glu Ala Thr Phe Gly Leu Ser Glu Ile
                100                 105                 110

Asn Trp Gly Ile Pro Pro Gly Asn Leu Val Ser Lys Ala Met Ala Asp
            115                 120                 125

Thr Val Gly His Arg Glu Ser Leu Tyr Tyr Ile Met Thr Gly Lys Thr
    130                 135                 140

Phe Gly Gly Gln Gln Ala Ala Lys Met Gly Leu Val Asn Gln Ser Val
145                 150                 155                 160

Pro Leu Ala Glu Leu Arg Ser Val Thr Val Glu Leu Ala Gln Asn Leu
                165                 170                 175

Leu Asp Lys Asn Pro Val Val Leu Arg Ala Ala Lys Ile Gly Phe Lys
            180                 185                 190

Arg Cys Arg Glu Leu Thr Trp Glu Gln Asn Glu Asp Tyr Leu Tyr Ala
        195                 200                 205

Lys Leu Asp Gln Ser Arg Leu Leu Asp Pro Glu Gly Gly Arg Glu Gln
    210                 215                 220

Gly Met Lys Gln Phe Leu Asp Glu Lys Ser Ile Lys Pro Gly Leu Gln
225                 230                 235                 240

Thr Tyr Lys Arg
```

<210> SEQ ID NO 27
<211> LENGTH: 1446
<212> TYPE: DNA
<213> ORGANISM: not required under old rule
<220> FEATURE:
<221> NAME/KEY: CDS
<222> LOCATION: (1)..(1443)
<223> OTHER INFORMATION: product = Vanillin-Dehydrogenase" / gene = "vdh"

<400> SEQUENCE: 27

```
atg ttt cac gtg ccc ctg ctt att ggt ggt aag cct tgt tca gca tct      48
Met Phe His Val Pro Leu Leu Ile Gly Gly Lys Pro Cys Ser Ala Ser
  1               5                  10                  15
```

-continued

| | |
|---|---|
| gat gag cgc acc ttc gag cgt cgt agc ccg ctg acc gga gaa gtg gta<br>Asp Glu Arg Thr Phe Glu Arg Arg Ser Pro Leu Thr Gly Glu Val Val<br>20                         25                    30 | 96 |
| tcg cgc gtc gct gct gcc agt ttg gaa gat gcg gac gcc gca gtg gcc<br>Ser Arg Val Ala Ala Ala Ser Leu Glu Asp Ala Asp Ala Ala Val Ala<br>35                         40                    45 | 144 |
| gct gca cag gct gcg ttt cct gaa tgg gcg gcg ctt gct ccg agc gaa<br>Ala Ala Gln Ala Ala Phe Pro Glu Trp Ala Ala Leu Ala Pro Ser Glu<br>50                         55                    60 | 192 |
| cgc cgt gcc cga ctg ctg cga gcg gcg gat ctt cta gag gac cgt tct<br>Arg Arg Ala Arg Leu Leu Arg Ala Ala Asp Leu Leu Glu Asp Arg Ser<br>65                         70                    75                    80 | 240 |
| tcc gag ttc acc gcc gca gcg agt gaa act ggc gca gcg gga aac tgg<br>Ser Glu Phe Thr Ala Ala Ala Ser Glu Thr Gly Ala Ala Gly Asn Trp<br>85                       90                    95 | 288 |
| tat ggg ttt aac gtt tac ctg gcg gcg ggc atg ttg cgg gaa gcc gcg<br>Tyr Gly Phe Asn Val Tyr Leu Ala Ala Gly Met Leu Arg Glu Ala Ala<br>                    100                    105                    110 | 336 |
| gcc atg acc aca cag att cag ggc gat gtc att ccg tcc aat gtg ccc<br>Ala Met Thr Thr Gln Ile Gln Gly Asp Val Ile Pro Ser Asn Val Pro<br>         115                    120                    125 | 384 |
| ggt agc ttt gcc atg gcg gtt cga cag cca tgt ggc gtg gtg ctc ggt<br>Gly Ser Phe Ala Met Ala Val Arg Gln Pro Cys Gly Val Val Leu Gly<br>130                        135                    140 | 432 |
| att gcg cct tgg aat gct ccg gta atc ctt ggc gta cgg gct gtt gcg<br>Ile Ala Pro Trp Asn Ala Pro Val Ile Leu Gly Val Arg Ala Val Ala<br>145                      150                    155                    160 | 480 |
| atg ccg ttg gca tgc ggc aat acc gtg gtg ttg aaa agc tct gag ctg<br>Met Pro Leu Ala Cys Gly Asn Thr Val Val Leu Lys Ser Ser Glu Leu<br>         165                    170                    175 | 528 |
| agt ccc ttt acc cat cgc ctg att ggt cag gtg ttg cat gat gct ggt<br>Ser Pro Phe Thr His Arg Leu Ile Gly Gln Val Leu His Asp Ala Gly<br>180                        185                    190 | 576 |
| ctg ggg gat ggc gtg gtg aat gtc atc agc aat gcc ccg caa gac gct<br>Leu Gly Asp Gly Val Val Asn Val Ile Ser Asn Ala Pro Gln Asp Ala<br>195                        200                    205 | 624 |
| cct gcg gtg gtg gag cga ctg att gca aat cct gcg gta cgt cga gtg<br>Pro Ala Val Val Glu Arg Leu Ile Ala Asn Pro Ala Val Arg Arg Val<br>210                        215                    220 | 672 |
| aac ttc acc ggt tcg acc cac gtt gga cgg atc att ggt gag ctg tct<br>Asn Phe Thr Gly Ser Thr His Val Gly Arg Ile Ile Gly Glu Leu Ser<br>225                      230                    235                    240 | 720 |
| gcg cgt cat ctg aag cct gct gtg ctg gaa tta ggt ggt aag gct ccg<br>Ala Arg His Leu Lys Pro Ala Val Leu Glu Leu Gly Gly Lys Ala Pro<br>         245                    250                    255 | 768 |
| ttc ttg gtc ttg gac gat gcc gac ctc gat gcg gcg gtc gaa gcg gcg<br>Phe Leu Val Leu Asp Asp Ala Asp Leu Asp Ala Ala Val Glu Ala Ala<br>260                        265                    270 | 816 |
| gcc ttt ggt gcc tac ttc aat cag ggt caa atc tgc atg tcc act gag<br>Ala Phe Gly Ala Tyr Phe Asn Gln Gly Gln Ile Cys Met Ser Thr Glu<br>275                        280                    285 | 864 |
| cgt ctg att gtg aca gca gtc gca gac gcc ttt gtt gaa aag ctg gcg<br>Arg Leu Ile Val Thr Ala Val Ala Asp Ala Phe Val Glu Lys Leu Ala<br>290                        295                    300 | 912 |
| agg aag gtc gcc aca ctg cgt gct ggc gat cct aat gat ccg caa tcg<br>Arg Lys Val Ala Thr Leu Arg Ala Gly Asp Pro Asn Asp Pro Gln Ser<br>305                      310                    315                    320 | 960 |
| gtc ttg ggt tcg ttg att gat gcc aat gca ggt caa cgc atc cag gtt<br>Val Leu Gly Ser Leu Ile Asp Ala Asn Ala Gly Gln Arg Ile Gln Val<br>         325                    330                    335 | 1008 |

```
ctg gtc gat gat gcg ctc gca aaa ggc gcg cgg cag gtc gtc ggt ggt      1056
Leu Val Asp Asp Ala Leu Ala Lys Gly Ala Arg Gln Val Val Gly Gly
            340                 345                 350 ggc tta gat ggc agc atc atg cag ccg atg ctg ctt gat cag gtc act      1104
Gly Leu Asp Gly Ser Ile Met Gln Pro Met Leu Leu Asp Gln Val Thr
        355                 360                 365 gaa gag atg cgc ctc tac cgt gag gag tcc ttt ggc cct gtt gcc gtt      1152
Glu Glu Met Arg Leu Tyr Arg Glu Glu Ser Phe Gly Pro Val Ala Val
    370                 375                 380 gtc ttg cgc ggc gat ggt gat gaa gaa ctg ctg cgt ctt gcc aac gat      1200
Val Leu Arg Gly Asp Gly Asp Glu Glu Leu Leu Arg Leu Ala Asn Asp
385                 390                 395                 400 tcg gag ttt ggt ctt tcg gcc gcc att ttc agc cgt gac gtc tcg cgc      1248
Ser Glu Phe Gly Leu Ser Ala Ala Ile Phe Ser Arg Asp Val Ser Arg
                405                 410                 415 gca atg gaa ttg gcc cag cgc gtc gat tcg ggc att tgc cat atc aat      1296
Ala Met Glu Leu Ala Gln Arg Val Asp Ser Gly Ile Cys His Ile Asn
            420                 425                 430 gga ccg act gtg cat gac gag gct cag atg cca ttc ggt ggg gtg aag      1344
Gly Pro Thr Val His Asp Glu Ala Gln Met Pro Phe Gly Gly Val Lys
        435                 440                 445 tcc agc ggc tac ggc agc ttc ggc agt cga gca tcg att gag cac ttt      1392
Ser Ser Gly Tyr Gly Ser Phe Gly Ser Arg Ala Ser Ile Glu His Phe
    450                 455                 460 acc cag ctg cgc tgg ctg acc att cag aat ggc ccg cgg cac tat cca      1440
Thr Gln Leu Arg Trp Leu Thr Ile Gln Asn Gly Pro Arg His Tyr Pro
465                 470                 475                 480 atc taa                                                              1446
Ile
```

<210> SEQ ID NO 28
<211> LENGTH: 481
<212> TYPE: PRT
<213> ORGANISM: not required under old rule

<400> SEQUENCE: 28

```
Met Phe His Val Pro Leu Leu Ile Gly Gly Lys Pro Cys Ser Ala Ser
  1               5                  10                  15

Asp Glu Arg Thr Phe Glu Arg Arg Ser Pro Leu Thr Gly Glu Val Val
             20                  25                  30

Ser Arg Val Ala Ala Ala Ser Leu Glu Asp Ala Asp Ala Ala Val Ala
         35                  40                  45

Ala Ala Gln Ala Ala Phe Pro Glu Trp Ala Ala Leu Ala Pro Ser Glu
     50                  55                  60

Arg Arg Ala Arg Leu Leu Arg Ala Ala Asp Leu Leu Glu Asp Arg Ser
 65                  70                  75                  80

Ser Glu Phe Thr Ala Ala Ala Ser Glu Thr Gly Ala Ala Gly Asn Trp
                 85                  90                  95

Tyr Gly Phe Asn Val Tyr Leu Ala Ala Gly Met Leu Arg Glu Ala Ala
            100                 105                 110

Ala Met Thr Thr Gln Ile Gln Gly Asp Val Ile Pro Ser Asn Val Pro
        115                 120                 125

Gly Ser Phe Ala Met Ala Val Arg Gln Pro Cys Gly Val Val Leu Gly
    130                 135                 140

Ile Ala Pro Trp Asn Ala Pro Val Ile Leu Gly Val Arg Ala Val Ala
145                 150                 155                 160

Met Pro Leu Ala Cys Gly Asn Thr Val Val Leu Lys Ser Ser Glu Leu
```

```
                    165                 170                 175
Ser Pro Phe Thr His Arg Leu Ile Gly Gln Val Leu His Asp Ala Gly
                180                 185                 190

Leu Gly Asp Gly Val Val Asn Val Ile Ser Asn Ala Pro Gln Asp Ala
            195                 200                 205

Pro Ala Val Val Glu Arg Leu Ile Ala Asn Pro Ala Val Arg Arg Val
        210                 215                 220

Asn Phe Thr Gly Ser Thr His Val Gly Arg Ile Ile Gly Glu Leu Ser
225                 230                 235                 240

Ala Arg His Leu Lys Pro Ala Val Leu Glu Leu Gly Lys Ala Pro
                245                 250                 255

Phe Leu Val Leu Asp Asp Ala Asp Leu Asp Ala Ala Val Glu Ala Ala
                260                 265                 270

Ala Phe Gly Ala Tyr Phe Asn Gln Gly Gln Ile Cys Met Ser Thr Glu
            275                 280                 285

Arg Leu Ile Val Thr Ala Val Ala Asp Ala Phe Val Glu Lys Leu Ala
        290                 295                 300

Arg Lys Val Ala Thr Leu Arg Ala Gly Asp Pro Asn Asp Pro Gln Ser
305                 310                 315                 320

Val Leu Gly Ser Leu Ile Asp Ala Asn Ala Gly Gln Arg Ile Gln Val
                325                 330                 335

Leu Val Asp Asp Ala Leu Ala Lys Gly Ala Arg Gln Val Val Gly Gly
                340                 345                 350

Gly Leu Asp Gly Ser Ile Met Gln Pro Met Leu Leu Asp Gln Val Thr
            355                 360                 365

Glu Glu Met Arg Leu Tyr Arg Glu Glu Ser Phe Gly Pro Val Ala Val
        370                 375                 380

Val Leu Arg Gly Asp Gly Asp Glu Glu Leu Leu Arg Leu Ala Asn Asp
385                 390                 395                 400

Ser Glu Phe Gly Leu Ser Ala Ala Ile Phe Ser Arg Asp Val Ser Arg
                405                 410                 415

Ala Met Glu Leu Ala Gln Arg Val Asp Ser Gly Ile Cys His Ile Asn
            420                 425                 430

Gly Pro Thr Val His Asp Glu Ala Gln Met Pro Phe Gly Gly Val Lys
        435                 440                 445

Ser Ser Gly Tyr Gly Ser Phe Gly Ser Arg Ala Ser Ile Glu His Phe
    450                 455                 460

Thr Gln Leu Arg Trp Leu Thr Ile Gln Asn Gly Pro Arg His Tyr Pro
465                 470                 475                 480

Ile
```

<210> SEQ ID NO 29
<211> LENGTH: 1770
<212> TYPE: DNA
<213> ORGANISM: not required under old rule
<220> FEATURE:
<221> NAME/KEY: CDS
<222> LOCATION: (1)..(1767)
<223> OTHER INFORMATION: product = "Ferulasaeure-CoA-Synthetase" / gene
      = "fcs"

<400> SEQUENCE: 29

```
atg cgt tct ctc gag gcg ctt ctt ccc ttc ccg ggt cga att ctt gag      48
Met Arg Ser Leu Glu Ala Leu Leu Pro Phe Pro Gly Arg Ile Leu Glu
  1               5                  10                  15 cgt ctc gag cat tgg gct aag acc cgt cca gaa caa acc tgc gtt gct      96
```

-continued

| | |
|---|---|
| Arg Leu Glu His Trp Ala Lys Thr Arg Pro Glu Gln Thr Cys Val Ala<br>20 25 30 | |
| gcc agg gcg gca aat ggg gaa tgg cgt cgt atc agc tac gcg gaa atg<br>Ala Arg Ala Ala Asn Gly Glu Trp Arg Arg Ile Ser Tyr Ala Glu Met<br>35 40 45 | 144 |
| ttc cac aac gtc cgc gcc atc gca cag agc ttg ctt cct tac gga cta<br>Phe His Asn Val Arg Ala Ile Ala Gln Ser Leu Leu Pro Tyr Gly Leu<br>50 55 60 | 192 |
| tcg gca gag cgt ccg ctg ctt atc gtc tct gga aat gac ctg gaa cat<br>Ser Ala Glu Arg Pro Leu Leu Ile Val Ser Gly Asn Asp Leu Glu His<br>65 70 75 80 | 240 |
| ctt cag ctg gca ttt ggg gct atg tat gcg ggc att ccc tat tgc ccg<br>Leu Gln Leu Ala Phe Gly Ala Met Tyr Ala Gly Ile Pro Tyr Cys Pro<br>85 90 95 | 288 |
| gtg tct cct gct tat tca ctg ctg tcg caa gat ttg gcg aag ctg cgt<br>Val Ser Pro Ala Tyr Ser Leu Leu Ser Gln Asp Leu Ala Lys Leu Arg<br>100 105 110 | 336 |
| cac atc gta ggt ctt ctg caa ccg gga ctg gtc ttt gct gcc gat gca<br>His Ile Val Gly Leu Leu Gln Pro Gly Leu Val Phe Ala Ala Asp Ala<br>115 120 125 | 384 |
| gca cct ttc cag cgc gca att gag acc att ctg ccg gac gac gtg ccc<br>Ala Pro Phe Gln Arg Ala Ile Glu Thr Ile Leu Pro Asp Asp Val Pro<br>130 135 140 | 432 |
| gca atc ttc act cga ggc gaa ttg gcc ggg cgg cgc acg gtg agt ttt<br>Ala Ile Phe Thr Arg Gly Glu Leu Ala Gly Arg Arg Thr Val Ser Phe<br>145 150 155 160 | 480 |
| gac agc ctg ctg gag cag cct ggt ggg att gag gca gat aat gcc ttt<br>Asp Ser Leu Leu Glu Gln Pro Gly Gly Ile Glu Ala Asp Asn Ala Phe<br>165 170 175 | 528 |
| gcg gca act ggc ccc gat acg att gcc aag ttc ttg ttc act tct ggc<br>Ala Ala Thr Gly Pro Asp Thr Ile Ala Lys Phe Leu Phe Thr Ser Gly<br>180 185 190 | 576 |
| tct acc aaa ctg cct aag gcg gtg ccg act act cag cga atg ctc tgc<br>Ser Thr Lys Leu Pro Lys Ala Val Pro Thr Thr Gln Arg Met Leu Cys<br>195 200 205 | 624 |
| gcc aat cag cag atg ctt ctg caa act ttc ccg gtt ttt ggt gaa gag<br>Ala Asn Gln Gln Met Leu Leu Gln Thr Phe Pro Val Phe Gly Glu Glu<br>210 215 220 | 672 |
| ccg ccg gtg ctg gtg gac tgg ttg ccg tgg aac cac acc ttc ggc ggc<br>Pro Pro Val Leu Val Asp Trp Leu Pro Trp Asn His Thr Phe Gly Gly<br>225 230 235 240 | 720 |
| agc cac aac atc ggc atc gtg ttg tac aac ggc ggc acg tac tac ctt<br>Ser His Asn Ile Gly Ile Val Leu Tyr Asn Gly Gly Thr Tyr Tyr Leu<br>245 250 255 | 768 |
| gac gac ggt aaa cca acc gcc caa ggg ttc gcc gag acg ctt cgc aac<br>Asp Asp Gly Lys Pro Thr Ala Gln Gly Phe Ala Glu Thr Leu Arg Asn<br>260 265 270 | 816 |
| ttg agc gaa atc tct ccc act gcg tac ctc act gtg ccg aaa ggc tgg<br>Leu Ser Glu Ile Ser Pro Thr Ala Tyr Leu Thr Val Pro Lys Gly Trp<br>275 280 285 | 864 |
| gag gaa tta gtg ggt gcc ctt gag cga gac agt acc ctg cgc gaa cgc<br>Glu Glu Leu Val Gly Ala Leu Glu Arg Asp Ser Thr Leu Arg Glu Arg<br>290 295 300 | 912 |
| ttc ttc gct cgc atg aag ctg ttc ttc ttc gcg gcg gct ggg ttg tcg<br>Phe Phe Ala Arg Met Lys Leu Phe Phe Phe Ala Ala Ala Gly Leu Ser<br>305 310 315 320 | 960 |
| caa ggg atc tgg gat cgt ttg gac cgg gtc gct gaa cag cac tgt ggt<br>Gln Gly Ile Trp Asp Arg Leu Asp Arg Val Ala Glu Gln His Cys Gly<br>325 330 335 | 1008 |

```
gag cgc att cgc atg atg gcg ggt ctg ggc atg acg gag act gct cct    1056
Glu Arg Ile Arg Met Met Ala Gly Leu Gly Met Thr Glu Thr Ala Pro
        340                 345                 350 tcc tgc act ttt acc acc gga ccg ctg tcg atg gct ggt tac att ggg    1104
Ser Cys Thr Phe Thr Thr Gly Pro Leu Ser Met Ala Gly Tyr Ile Gly
355                 360                 365 ctg cca gcg cct ggc tgc gag gtc aag ctc gtt ccg gtc gat ggg aaa    1152
Leu Pro Ala Pro Gly Cys Glu Val Lys Leu Val Pro Val Asp Gly Lys
        370                 375                 380 ttg gaa ggg cgt ttc cat ggt ccg cac gtc atg agc ggc tac tgg cgt    1200
Leu Glu Gly Arg Phe His Gly Pro His Val Met Ser Gly Tyr Trp Arg
385                 390                 395                 400 gct cct gaa caa aat gcc caa gcg ttc gac gag gaa ggc tat tac tgc    1248
Ala Pro Glu Gln Asn Ala Gln Ala Phe Asp Glu Glu Gly Tyr Tyr Cys
        405                 410                 415 tcc ggt gat gcc atc aaa ttg gca gat cct gcc gat cct cag aaa ggt    1296
Ser Gly Asp Ala Ile Lys Leu Ala Asp Pro Ala Asp Pro Gln Lys Gly
        420                 425                 430 ctg atg ttt gac ggt cga att gct gaa gac ttc aag ctg tcc tca ggg    1344
Leu Met Phe Asp Gly Arg Ile Ala Glu Asp Phe Lys Leu Ser Ser Gly
        435                 440                 445 gta ttt gtc agc gtt ggg cca ttg cgc acg cgg gcg gtt ctg gaa ggc    1392
Val Phe Val Ser Val Gly Pro Leu Arg Thr Arg Ala Val Leu Glu Gly
450                 455                 460 ggc tct tac gtc ctg gac gta gtg gtt gct gct cct gat cgt gaa tgc    1440
Gly Ser Tyr Val Leu Asp Val Val Val Ala Ala Pro Asp Arg Glu Cys
465                 470                 475                 480 ctt gga ttg ctc gtg ttt ccg cgt ctt ctc gac tgc cgt gcc ttg tcg    1488
Leu Gly Leu Leu Val Phe Pro Arg Leu Leu Asp Cys Arg Ala Leu Ser
                485                 490                 495 ggg cta gga aaa gag gcg tcg gac gcc gag gtg ctt gcc agt gag ccg    1536
Gly Leu Gly Lys Glu Ala Ser Asp Ala Glu Val Leu Ala Ser Glu Pro
            500                 505                 510 gtt cgg gcc tgg ttt gct gac tgg ctc aaa cga ctc aat cga gaa gca    1584
Val Arg Ala Trp Phe Ala Asp Trp Leu Lys Arg Leu Asn Arg Glu Ala
        515                 520                 525 act ggc aat gcc agt cgc atc atg tgg gta ggg ctc ctc gat acg ccg    1632
Thr Gly Asn Ala Ser Arg Ile Met Trp Val Gly Leu Leu Asp Thr Pro
530                 535                 540 ccg tcg att gat aag ggc gag gtc act gac aag ggc tcg atc aac cag    1680
Pro Ser Ile Asp Lys Gly Glu Val Thr Asp Lys Gly Ser Ile Asn Gln
545                 550                 555                 560 cgc gct gtt ttg caa tgg cgg tcg gcg aaa gtt gat gcg ctg tat cgt    1728
Arg Ala Val Leu Gln Trp Arg Ser Ala Lys Val Asp Ala Leu Tyr Arg
                565                 570                 575 ggt gaa gat caa tcc atg ctg cgt gac gag gcc aca ctg tga            1770
Gly Glu Asp Gln Ser Met Leu Arg Asp Glu Ala Thr Leu
            580                 585

<210> SEQ ID NO 30
<211> LENGTH: 589
<212> TYPE: PRT
<213> ORGANISM: not required under old rule

<400> SEQUENCE: 30

Met Arg Ser Leu Glu Ala Leu Leu Pro Phe Pro Gly Arg Ile Leu Glu
  1               5                  10                  15

Arg Leu Glu His Trp Ala Lys Thr Arg Pro Glu Gln Thr Cys Val Ala
             20                  25                  30

Ala Arg Ala Ala Asn Gly Glu Trp Arg Arg Ile Ser Tyr Ala Glu Met
```

-continued

```
                35                  40                  45
        Phe His Asn Val Arg Ala Ile Ala Gln Ser Leu Leu Pro Tyr Gly Leu
                        50                  55                  60
        Ser Ala Glu Arg Pro Leu Leu Ile Val Ser Gly Asn Asp Leu Glu His
         65                  70                  75                  80
        Leu Gln Leu Ala Phe Gly Ala Met Tyr Ala Gly Ile Pro Tyr Cys Pro
                            85                  90                  95
        Val Ser Pro Ala Tyr Ser Leu Leu Ser Gln Asp Leu Ala Lys Leu Arg
                        100                 105                 110
        His Ile Val Gly Leu Leu Gln Pro Gly Leu Val Phe Ala Ala Asp Ala
                        115                 120                 125
        Ala Pro Phe Gln Arg Ala Ile Glu Thr Ile Leu Pro Asp Asp Val Pro
                130                 135                 140
        Ala Ile Phe Thr Arg Gly Glu Leu Ala Gly Arg Arg Thr Val Ser Phe
        145                 150                 155                 160
        Asp Ser Leu Leu Glu Gln Pro Gly Gly Ile Glu Ala Asp Asn Ala Phe
                        165                 170                 175
        Ala Ala Thr Gly Pro Asp Thr Ile Ala Lys Phe Leu Phe Thr Ser Gly
                        180                 185                 190
        Ser Thr Lys Leu Pro Lys Ala Val Pro Thr Thr Gln Arg Met Leu Cys
                    195                 200                 205
        Ala Asn Gln Gln Met Leu Leu Gln Thr Phe Pro Val Phe Gly Glu Glu
                    210                 215                 220
        Pro Pro Val Leu Val Asp Trp Leu Pro Trp Asn His Thr Phe Gly Gly
        225                 230                 235                 240
        Ser His Asn Ile Gly Ile Val Leu Tyr Asn Gly Gly Thr Tyr Tyr Leu
                        245                 250                 255
        Asp Asp Gly Lys Pro Thr Ala Gln Gly Phe Ala Glu Thr Leu Arg Asn
                    260                 265                 270
        Leu Ser Glu Ile Ser Pro Thr Ala Tyr Leu Thr Val Pro Lys Gly Trp
                    275                 280                 285
        Glu Glu Leu Val Gly Ala Leu Glu Arg Asp Ser Thr Leu Arg Glu Arg
                    290                 295                 300
        Phe Phe Ala Arg Met Lys Leu Phe Phe Ala Ala Ala Gly Leu Ser
        305                 310                 315                 320
        Gln Gly Ile Trp Asp Arg Leu Asp Arg Val Ala Glu Gln His Cys Gly
                        325                 330                 335
        Glu Arg Ile Arg Met Met Ala Gly Leu Gly Met Thr Glu Thr Ala Pro
                        340                 345                 350
        Ser Cys Thr Phe Thr Thr Gly Pro Leu Ser Met Ala Gly Tyr Ile Gly
                    355                 360                 365
        Leu Pro Ala Pro Gly Cys Glu Val Lys Leu Val Pro Val Asp Gly Lys
            370                 375                 380
        Leu Glu Gly Arg Phe His Gly Pro His Val Met Ser Gly Tyr Trp Arg
        385                 390                 395                 400
        Ala Pro Glu Gln Asn Ala Gln Ala Phe Asp Glu Glu Gly Tyr Tyr Cys
                            405                 410                 415
        Ser Gly Asp Ala Ile Lys Leu Ala Asp Pro Ala Asp Pro Gln Lys Gly
                        420                 425                 430
        Leu Met Phe Asp Gly Arg Ile Ala Glu Asp Phe Lys Leu Ser Ser Gly
                    435                 440                 445
        Val Phe Val Ser Val Gly Pro Leu Arg Thr Arg Ala Val Leu Glu Gly
        450                 455                 460
```

```
Gly Ser Tyr Val Leu Asp Val Val Ala Ala Pro Asp Arg Glu Cys
465                 470                 475                 480

Leu Gly Leu Leu Val Phe Pro Arg Leu Leu Asp Cys Arg Ala Leu Ser
            485                 490                 495

Gly Leu Gly Lys Glu Ala Ser Asp Ala Glu Val Leu Ala Ser Glu Pro
                500                 505                 510

Val Arg Ala Trp Phe Ala Asp Trp Leu Lys Arg Leu Asn Arg Glu Ala
            515                 520                 525

Thr Gly Asn Ala Ser Arg Ile Met Trp Val Gly Leu Leu Asp Thr Pro
        530                 535                 540

Pro Ser Ile Asp Lys Gly Glu Val Thr Asp Lys Gly Ser Ile Asn Gln
545                 550                 555                 560

Arg Ala Val Leu Gln Trp Arg Ser Ala Lys Val Asp Ala Leu Tyr Arg
                565                 570                 575

Gly Glu Asp Gln Ser Met Leu Arg Asp Glu Ala Thr Leu
                580                 585

<210> SEQ ID NO 31
<211> LENGTH: 1296
<212> TYPE: DNA
<213> ORGANISM: not required under old rule
<220> FEATURE:
<221> NAME/KEY: CDS
<222> LOCATION: (1)..(1293)
<223> OTHER INFORMATION: product = "beta-Ketothiolase" / gene = "aat"

<400> SEQUENCE: 31 atg agt tgg tca ggg ggg gct tac tcg gcg ttt tcc gac act gcg ttg      48
Met Ser Trp Ser Gly Gly Ala Tyr Ser Ala Phe Ser Asp Thr Ala Leu
  1               5                  10                  15 gtt gcg gca gtg cgc acc ccc tgg att gat tgc ggg ggt gcc ctg tcg      96
Val Ala Ala Val Arg Thr Pro Trp Ile Asp Cys Gly Gly Ala Leu Ser
             20                  25                  30 ctg gtg tcg cct atc gac tta ggg gta aag gtc gct cgc gaa gtt ctg     144
Leu Val Ser Pro Ile Asp Leu Gly Val Lys Val Ala Arg Glu Val Leu
         35                  40                  45 atg cgt gcg tcg ctt gaa cca caa atg gtc gat agc gta ctc gca ggc     192
Met Arg Ala Ser Leu Glu Pro Gln Met Val Asp Ser Val Leu Ala Gly
     50                  55                  60 tct atg gct caa gca agc ttt gat gct tac ctg ctc ccg cgg cac att     240
Ser Met Ala Gln Ala Ser Phe Asp Ala Tyr Leu Leu Pro Arg His Ile
 65                  70                  75                  80 ggc ttg tac agc ggt gtt ccc aag tcg gtt ccg gcc ttg ggg gtg cag     288
Gly Leu Tyr Ser Gly Val Pro Lys Ser Val Pro Ala Leu Gly Val Gln
                 85                  90                  95 cgc att tgc ggc aca ggc ttc gaa ctg ctt cgg cag gcc ggc gag cag     336
Arg Ile Cys Gly Thr Gly Phe Glu Leu Leu Arg Gln Ala Gly Glu Gln
            100                 105                 110 att tcc caa ggc gct gat cac gtg ctg tgt gtc gcg gca gag tcc atg     384
Ile Ser Gln Gly Ala Asp His Val Leu Cys Val Ala Ala Glu Ser Met
        115                 120                 125 tcg cgt aac ccc atc gcg tcg tat aca cac cgg ggc ggg ttc cgc ctc     432
Ser Arg Asn Pro Ile Ala Ser Tyr Thr His Arg Gly Gly Phe Arg Leu
    130                 135                 140 ggt gcg ccc gtt gag ttc aag gat ttt ttg tgg gag gca ttg ttt gat     480
Gly Ala Pro Val Glu Phe Lys Asp Phe Leu Trp Glu Ala Leu Phe Asp
145                 150                 155                 160 cct gct cca gga ctc gac atg atc gct acc gca gaa aac ctg gcg cgc     528
Pro Ala Pro Gly Leu Asp Met Ile Ala Thr Ala Glu Asn Leu Ala Arg
```

```
                165                 170                 175
ctg tac gga atc acc agg gga gaa gct aat tcc tac gcg gta agc agc    576
Leu Tyr Gly Ile Thr Arg Gly Glu Ala Asn Ser Tyr Ala Val Ser Ser
            180                 185                 190 ttc gag cgc gca ttg agg gcg caa gag gag aaa tgg att gac caa gag    624
Phe Glu Arg Ala Leu Arg Ala Gln Glu Glu Lys Trp Ile Asp Gln Glu
        195                 200                 205 atc gtg gct gtt acg gat gaa cag ttc gat tta gag ggc tac aac agt    672
Ile Val Ala Val Thr Asp Glu Gln Phe Asp Leu Glu Gly Tyr Asn Ser
    210                 215                 220 cga gca att gaa ctg cct cgg aag gca aaa ttg ttg atc gtg aca gtc    720
Arg Ala Ile Glu Leu Pro Arg Lys Ala Lys Leu Leu Ile Val Thr Val
225                 230                 235                 240 atc cgc ggc cta gca gtc ttt gaa gcc ctt tcc cga ttg aag cct gtt    768
Ile Arg Gly Leu Ala Val Phe Glu Ala Leu Ser Arg Leu Lys Pro Val
                245                 250                 255 cat tct ggc ggg gtg cag act gcg ggc aac agc tgt gcc gta gtg gac    816
His Ser Gly Gly Val Gln Thr Ala Gly Asn Ser Cys Ala Val Val Asp
            260                 265                 270 ggc gcc gcg gcg gct ttg gtg gct cga gag tcg tct gcg aca cag ccg    864
Gly Ala Ala Ala Ala Leu Val Ala Arg Glu Ser Ser Ala Thr Gln Pro
        275                 280                 285 gtc ttg gct agg ata ctg gct acc tcc gta gtc ggg atc gag ccc gag    912
Val Leu Ala Arg Ile Leu Ala Thr Ser Val Val Gly Ile Glu Pro Glu
    290                 295                 300 cat atg ggg ctc ggc cct gcg ccc gcg att cgc ctg ctg ctt gcg cgt    960
His Met Gly Leu Gly Pro Ala Pro Ala Ile Arg Leu Leu Leu Ala Arg
305                 310                 315                 320 agt gat ctt agt ttg agg gat atc gac ctc ttt gag ata aac gag gcg   1008
Ser Asp Leu Ser Leu Arg Asp Ile Asp Leu Phe Glu Ile Asn Glu Ala
                325                 330                 335 cag gcc gcc caa gtt cta gcg gta cag cat gaa ttg ggt att gag cac   1056
Gln Ala Ala Gln Val Leu Ala Val Gln His Glu Leu Gly Ile Glu His
            340                 345                 350 tca aaa ctt aat att tgg ggc ggg gcc att gca ctt gga cac ccg ctt   1104
Ser Lys Leu Asn Ile Trp Gly Gly Ala Ile Ala Leu Gly His Pro Leu
        355                 360                 365 gcc gcg acc gga ttg cgt ctc tgc atg acc ctc gct cac caa ttg caa   1152
Ala Ala Thr Gly Leu Arg Leu Cys Met Thr Leu Ala His Gln Leu Gln
    370                 375                 380 gct aat aac ttt cga tat gga att gcc tcg gca tgc att ggt ggg gga   1200
Ala Asn Asn Phe Arg Tyr Gly Ile Ala Ser Ala Cys Ile Gly Gly Gly
385                 390                 395                 400 cag ggg atg gcg gtt ctt tta gag aat ccc cac ttc ggt tcg tcc tct   1248
Gln Gly Met Ala Val Leu Leu Glu Asn Pro His Phe Gly Ser Ser Ser
                405                 410                 415 gca cga agt tcg atg att aac aga gtt gac cac tat cca ctg agc taa   1296
Ala Arg Ser Ser Met Ile Asn Arg Val Asp His Tyr Pro Leu Ser
            420                 425                 430

<210> SEQ ID NO 32
<211> LENGTH: 431
<212> TYPE: PRT
<213> ORGANISM: not required under old rule

<400> SEQUENCE: 32

Met Ser Trp Ser Gly Gly Ala Tyr Ser Ala Phe Ser Asp Thr Ala Leu
 1               5                  10                  15

Val Ala Ala Val Arg Thr Pro Trp Ile Asp Cys Gly Gly Ala Leu Ser
            20                  25                  30
```

-continued

```
Leu Val Ser Pro Ile Asp Leu Gly Val Lys Val Ala Arg Glu Val Leu
         35                  40                  45
Met Arg Ala Ser Leu Glu Pro Gln Met Val Asp Ser Val Leu Ala Gly
 50                  55                  60
Ser Met Ala Gln Ala Ser Phe Asp Ala Tyr Leu Leu Pro Arg His Ile
 65                  70                  75                  80
Gly Leu Tyr Ser Gly Val Pro Lys Ser Val Pro Ala Leu Gly Val Gln
                 85                  90                  95
Arg Ile Cys Gly Thr Gly Phe Glu Leu Leu Arg Gln Ala Gly Glu Gln
                100                 105                 110
Ile Ser Gln Gly Ala Asp His Val Leu Cys Val Ala Ala Glu Ser Met
             115                 120                 125
Ser Arg Asn Pro Ile Ala Ser Tyr Thr His Arg Gly Gly Phe Arg Leu
 130                 135                 140
Gly Ala Pro Val Glu Phe Lys Asp Phe Leu Trp Glu Ala Leu Phe Asp
 145                 150                 155                 160
Pro Ala Pro Gly Leu Asp Met Ile Ala Thr Ala Glu Asn Leu Ala Arg
                165                 170                 175
Leu Tyr Gly Ile Thr Arg Gly Glu Ala Asn Ser Tyr Ala Val Ser Ser
                180                 185                 190
Phe Glu Arg Ala Leu Arg Ala Gln Glu Glu Lys Trp Ile Asp Gln Glu
            195                 200                 205
Ile Val Ala Val Thr Asp Glu Gln Phe Asp Leu Glu Gly Tyr Asn Ser
            210                 215                 220
Arg Ala Ile Glu Leu Pro Arg Lys Ala Lys Leu Leu Ile Val Thr Val
225                 230                 235                 240
Ile Arg Gly Leu Ala Val Phe Glu Ala Leu Ser Arg Leu Lys Pro Val
                245                 250                 255
His Ser Gly Gly Val Gln Thr Ala Gly Asn Ser Cys Ala Val Val Asp
                260                 265                 270
Gly Ala Ala Ala Leu Val Ala Arg Glu Ser Ser Ala Thr Gln Pro
            275                 280                 285
Val Leu Ala Arg Ile Leu Ala Thr Ser Val Val Gly Ile Glu Pro Glu
 290                 295                 300
His Met Gly Leu Gly Pro Ala Pro Ala Ile Arg Leu Leu Ala Arg
305                 310                 315                 320
Ser Asp Leu Ser Leu Arg Asp Ile Asp Leu Phe Glu Ile Asn Glu Ala
                325                 330                 335
Gln Ala Ala Gln Val Leu Ala Val Gln His Glu Leu Gly Ile Glu His
            340                 345                 350
Ser Lys Leu Asn Ile Trp Gly Gly Ala Ile Ala Leu Gly His Pro Leu
            355                 360                 365
Ala Ala Thr Gly Leu Arg Leu Cys Met Thr Leu Ala His Gln Leu Gln
 370                 375                 380
Ala Asn Asn Phe Arg Tyr Gly Ile Ala Ser Ala Cys Ile Gly Gly Gly
385                 390                 395                 400
Gln Gly Met Ala Val Leu Leu Glu Asn Pro His Phe Gly Ser Ser Ser
                405                 410                 415
Ala Arg Ser Ser Met Ile Asn Arg Val Asp His Tyr Pro Leu Ser
            420                 425                 430

<210> SEQ ID NO 33
<211> LENGTH: 1596
```

```
<212> TYPE: DNA
<213> ORGANISM: not required under old rule
<220> FEATURE:
<221> NAME/KEY: CDS
<222> LOCATION: (1)..(1593)
<223> OTHER INFORMATION: product = "Chemotaxis-Protein" / gene = "mac"

<400> SEQUENCE: 33 atg att agt ttc gct cgt atg gca gaa agt tta gga gtc cag gct aaa        48
Met Ile Ser Phe Ala Arg Met Ala Glu Ser Leu Gly Val Gln Ala Lys
 1               5                  10                  15 ctt gcc ctt gcc ttc gca ctc gta tta tgt gtc ggg ctg att gtt acc        96
Leu Ala Leu Ala Phe Ala Leu Val Leu Cys Val Gly Leu Ile Val Thr
             20                  25                  30 ggc acg ggt ttc tac agt gta cat acc ttg tca ggg ttg gtg gaa aag       144
Gly Thr Gly Phe Tyr Ser Val His Thr Leu Ser Gly Leu Val Glu Lys
         35                  40                  45 agc gcg ata gct ggt gag ttg cgg gcg aaa att cag gaa ctg aag gtt       192
Ser Ala Ile Ala Gly Glu Leu Arg Ala Lys Ile Gln Glu Leu Lys Val
     50                  55                  60 ctg gag cag cgc gcc tta ttc atc gcc gat gaa ggg tcg ctg aag cag       240
Leu Glu Gln Arg Ala Leu Phe Ile Ala Asp Glu Gly Ser Leu Lys Gln
 65                  70                  75                  80 cgc tcg atc ctc cta agt cag gtg ata gct gaa gtt aat gat gct ata       288
Arg Ser Ile Leu Leu Ser Gln Val Ile Ala Glu Val Asn Asp Ala Ile
                 85                  90                  95 gat att ttt gac ttt cag cgc gga cga tct gag tta ctt aaa ttc gct       336
Asp Ile Phe Asp Phe Gln Arg Gly Arg Ser Glu Leu Leu Lys Phe Ala
            100                 105                 110 gct tct tcg cgc gaa gca agt tac tcc att gag gtc ggt agt aac gct       384
Ala Ser Ser Arg Glu Ala Ser Tyr Ser Ile Glu Val Gly Ser Asn Ala
        115                 120                 125 gcg gcc gat aag ttg cag tcg ggc gaa cca agt gac gca ttg atg gtt       432
Ala Ala Asp Lys Leu Gln Ser Gly Glu Pro Ser Asp Ala Leu Met Val
    130                 135                 140 gcc gat aaa aag ctg aat gtt gag tat gag caa ttg agt tct gct gtg       480
Ala Asp Lys Lys Leu Asn Val Glu Tyr Glu Gln Leu Ser Ser Ala Val
145                 150                 155                 160 aat gca ctg atg ggg cat tta att gag gat cag aat gaa aaa gtt cca       528
Asn Ala Leu Met Gly His Leu Ile Glu Asp Gln Asn Glu Lys Val Pro
                165                 170                 175 cta atc tac tat atg ctt ggc ggc gta act ttg ttt acg atg ctc atg       576
Leu Ile Tyr Tyr Met Leu Gly Gly Val Thr Leu Phe Thr Met Leu Met
            180                 185                 190 agt gct tat tcg gtc tgg ttc att tcg cgt cag tta gtt ccg cca tta       624
Ser Ala Tyr Ser Val Trp Phe Ile Ser Arg Gln Leu Val Pro Pro Leu
        195                 200                 205 aag tcg acg gtg cag ctt gcc gag cgg att gca tca ggc gac ttg gct       672
Lys Ser Thr Val Gln Leu Ala Glu Arg Ile Ala Ser Gly Asp Leu Ala
    210                 215                 220 gat gtc ggg gac agc agg cgc aag gat gaa atc ggt cag ttg caa agt       720
Asp Val Gly Asp Ser Arg Arg Lys Asp Glu Ile Gly Gln Leu Gln Ser
225                 230                 235                 240 gca act agg cgg atg gcg att gga ctg cgt aat ctg gtc ggt gat att       768
Ala Thr Arg Arg Met Ala Ile Gly Leu Arg Asn Leu Val Gly Asp Ile
                245                 250                 255 ggt caa agt cgt gcg caa ctg gtt tca tcg tcc agc gac ctt tcg gcc       816
Gly Gln Ser Arg Ala Gln Leu Val Ser Ser Ser Ser Asp Leu Ser Ala
            260                 265                 270 atc tgt gct cag gct cag att gat gtc gag tgc cag aag ctt tcg gtc       864
Ile Cys Ala Gln Ala Gln Ile Asp Val Glu Cys Gln Lys Leu Ser Val
```

-continued

```
              275                 280                 285
gcc cag gtc tct acc gcc gtg aac gag ttg gtt gaa acc gtc cag gca      912
Ala Gln Val Ser Thr Ala Val Asn Glu Leu Val Glu Thr Val Gln Ala
    290                 295                 300 ata gca aaa agc acc gaa gag gca gca aca gtc gcc gtc ttg gcc gat      960
Ile Ala Lys Ser Thr Glu Glu Ala Ala Thr Val Ala Val Leu Ala Asp
305                 310                 315                 320 gaa aag gca cgc ggt ggt gaa agt gtc gtt aac aag gcc gtt gat ttc     1008
Glu Lys Ala Arg Gly Gly Glu Ser Val Val Asn Lys Ala Val Asp Phe
                325                 330                 335 att gag cac ctc tcc gga gat atg gcg gaa ctg gga gac gca atg gag     1056
Ile Glu His Leu Ser Gly Asp Met Ala Glu Leu Gly Asp Ala Met Glu
            340                 345                 350 cgg ctt cag aac gac agt gcg cag atc aat aag gta gta gac gtc att     1104
Arg Leu Gln Asn Asp Ser Ala Gln Ile Asn Lys Val Val Asp Val Ile
        355                 360                 365 aag gct gtg gcg gag cag acc aat ctg cta gcc ctg aat gcg gcg ata     1152
Lys Ala Val Ala Glu Gln Thr Asn Leu Leu Ala Leu Asn Ala Ala Ile
    370                 375                 380 gag gcg gcc cgt gca gga gag cag ggc agg ggc ttt gcg gtc gtg gcg     1200
Glu Ala Ala Arg Ala Gly Glu Gln Gly Arg Gly Phe Ala Val Val Ala
385                 390                 395                 400 gat gag gtt cgt gct ttg gcg atg cgc acc caa caa tcg acc aaa gaa     1248
Asp Glu Val Arg Ala Leu Ala Met Arg Thr Gln Gln Ser Thr Lys Glu
                405                 410                 415 att gag agg cta gtg gtt tca ttg cag cag gga agt gaa gct gcg ggc     1296
Ile Glu Arg Leu Val Val Ser Leu Gln Gln Gly Ser Glu Ala Ala Gly
            420                 425                 430 gag ttg atg cgg cgt ggc aag gtc cgg acg cat gac gtc gtt gga ttg     1344
Glu Leu Met Arg Arg Gly Lys Val Arg Thr His Asp Val Val Gly Leu
        435                 440                 445 gcc cag caa gcc gcg cgc cgc gct act cga aat tac cca gct gtc gcc     1392
Ala Gln Gln Ala Ala Arg Arg Ala Thr Arg Asn Tyr Pro Ala Val Ala
    450                 455                 460 ggc atc caa gcg atg aac tat cag atc gcc gct gga gca gag cag caa     1440
Gly Ile Gln Ala Met Asn Tyr Gln Ile Ala Ala Gly Ala Glu Gln Gln
465                 470                 475                 480 ggg gct gct gtg gtt caa atc aac cag aat atg ctt gaa gtg cat aag     1488
Gly Ala Ala Val Val Gln Ile Asn Gln Asn Met Leu Glu Val His Lys
                485                 490                 495 atg gct gac gag tcc gcc att aaa gcg gga cag acc atg aag tca tcg     1536
Met Ala Asp Glu Ser Ala Ile Lys Ala Gly Gln Thr Met Lys Ser Ser
            500                 505                 510 aag gag ctt gct cac ctc ggc agt gcg cta caa aaa tcc gtt gat cga     1584
Lys Glu Leu Ala His Leu Gly Ser Ala Leu Gln Lys Ser Val Asp Arg
        515                 520                 525 ttc cag ctg tag                                                     1596
Phe Gln Leu
    530
```

<210> SEQ ID NO 34
<211> LENGTH: 531
<212> TYPE: PRT
<213> ORGANISM: not required under old rule

<400> SEQUENCE: 34

```
Met Ile Ser Phe Ala Arg Met Ala Glu Ser Leu Gly Val Gln Ala Lys
 1               5                  10                  15

Leu Ala Leu Ala Phe Ala Leu Val Leu Cys Val Gly Leu Ile Val Thr
                20                  25                  30
```

-continued

```
Gly Thr Gly Phe Tyr Ser Val His Thr Leu Ser Gly Leu Val Glu Lys
         35                  40                  45

Ser Ala Ile Ala Gly Glu Leu Arg Ala Lys Ile Gln Glu Leu Lys Val
 50                  55                  60

Leu Glu Gln Arg Ala Leu Phe Ile Ala Asp Glu Gly Ser Leu Lys Gln
 65                  70                  75                  80

Arg Ser Ile Leu Leu Ser Gln Val Ile Ala Glu Val Asn Asp Ala Ile
                 85                  90                  95

Asp Ile Phe Asp Phe Gln Arg Gly Arg Ser Glu Leu Leu Lys Phe Ala
                100                 105                 110

Ala Ser Ser Arg Glu Ala Ser Tyr Ser Ile Glu Val Gly Ser Asn Ala
                115                 120                 125

Ala Ala Asp Lys Leu Gln Ser Gly Glu Pro Ser Asp Ala Leu Met Val
130                 135                 140

Ala Asp Lys Lys Leu Asn Val Glu Tyr Glu Gln Leu Ser Ser Ala Val
145                 150                 155                 160

Asn Ala Leu Met Gly His Leu Ile Glu Asp Gln Asn Glu Lys Val Pro
                165                 170                 175

Leu Ile Tyr Tyr Met Leu Gly Gly Val Thr Leu Phe Thr Met Leu Met
                180                 185                 190

Ser Ala Tyr Ser Val Trp Phe Ile Ser Arg Gln Leu Val Pro Pro Leu
                195                 200                 205

Lys Ser Thr Val Gln Leu Ala Glu Arg Ile Ala Ser Gly Asp Leu Ala
                210                 215                 220

Asp Val Gly Asp Ser Arg Arg Lys Asp Glu Ile Gly Gln Leu Gln Ser
225                 230                 235                 240

Ala Thr Arg Arg Met Ala Ile Gly Leu Arg Asn Leu Val Gly Asp Ile
                245                 250                 255

Gly Gln Ser Arg Ala Gln Leu Val Ser Ser Ser Asp Leu Ser Ala
                260                 265                 270

Ile Cys Ala Gln Ala Gln Ile Asp Val Glu Cys Gln Lys Leu Ser Val
                275                 280                 285

Ala Gln Val Ser Thr Ala Val Asn Glu Leu Val Glu Thr Val Gln Ala
                290                 295                 300

Ile Ala Lys Ser Thr Glu Glu Ala Ala Thr Val Ala Val Leu Ala Asp
305                 310                 315                 320

Glu Lys Ala Arg Gly Gly Glu Ser Val Val Asn Lys Ala Val Asp Phe
                325                 330                 335

Ile Glu His Leu Ser Gly Asp Met Ala Glu Leu Gly Asp Ala Met Glu
                340                 345                 350

Arg Leu Gln Asn Asp Ser Ala Gln Ile Asn Lys Val Val Asp Val Ile
                355                 360                 365

Lys Ala Val Ala Glu Gln Thr Asn Leu Leu Ala Leu Asn Ala Ala Ile
                370                 375                 380

Glu Ala Ala Arg Ala Gly Glu Gln Gly Arg Gly Phe Ala Val Val Ala
385                 390                 395                 400

Asp Glu Val Arg Ala Leu Ala Met Arg Thr Gln Gln Ser Thr Lys Glu
                405                 410                 415

Ile Glu Arg Leu Val Val Ser Leu Gln Gln Gly Ser Glu Ala Ala Gly
                420                 425                 430

Glu Leu Met Arg Arg Gly Lys Val Arg Thr His Asp Val Val Gly Leu
                435                 440                 445
```

Ala Gln Gln Ala Ala Arg Arg Ala Thr Arg Asn Tyr Pro Ala Val Ala
    450                 455                 460

Gly Ile Gln Ala Met Asn Tyr Gln Ile Ala Ala Gly Ala Glu Gln Gln
465                 470                 475                 480

Gly Ala Ala Val Val Gln Ile Asn Gln Asn Met Leu Glu Val His Lys
                485                 490                 495

Met Ala Asp Glu Ser Ala Ile Lys Ala Gly Gln Thr Met Lys Ser Ser
            500                 505                 510

Lys Glu Leu Ala His Leu Gly Ser Ala Leu Gln Lys Ser Val Asp Arg
        515                 520                 525

Phe Gln Leu
    530

<210> SEQ ID NO 35
<211> LENGTH: 411
<212> TYPE: DNA
<213> ORGANISM: not required under old rule

<400> SEQUENCE: 35
ctagcctaac tgttgcgctt caggctccgc atggatcttg tgcagcagca atagcaattg      60
ttcacgttcg tcatcactca gcatcgacgt cgcgtcttgg tcgctctgta ccacgatctt     120
cttcagctct ttgagctgcg tctccccagc tttgctgaga aatatcccat aggaacgctt     180
gtccggcttg cagcgcacgc gcacagcaag gccgagcttc tcgagcttgt tcagcaaggg     240
aaccagttgt ggtggttcga ttgcgagcat ccgcgctagg tcagcctgca taagcccagg     300
gctcgcttcg atgattagaa gtgccgacag ctgcgccggg cgtaggtcat atggcgtcag     360
ggcttcaatc aggccctgag cgagcttcag ctgtgagccg gcgtaaggca t              411

<210> SEQ ID NO 36
<211> LENGTH: 136
<212> TYPE: PRT
<213> ORGANISM: not required under old rule

<400> SEQUENCE: 36

Met Pro Tyr Ala Gly Ser Gln Leu Lys Leu Ala Gln Gly Leu Ile Glu
  1               5                  10                  15

Ala Leu Thr Pro Tyr Asp Leu Arg Pro Ala Gln Leu Ser Ala Leu Leu
             20                  25                  30

Ile Ile Glu Ala Ser Pro Gly Leu Met Gln Ala Asp Leu Ala Arg Met
         35                  40                  45

Leu Ala Ile Glu Pro Pro Gln Leu Val Pro Leu Leu Asn Lys Leu Glu
     50                  55                  60

Lys Leu Gly Leu Ala Val Arg Val Arg Cys Lys Pro Asp Lys Arg Ser
 65                  70                  75                  80

Tyr Gly Ile Phe Leu Ser Lys Ala Gly Glu Thr Gln Leu Lys Glu Leu
                 85                  90                  95

Lys Lys Ile Val Val Gln Ser Asp Gln Asp Ala Thr Ser Met Leu Ser
            100                 105                 110

Asp Asp Glu Arg Glu Gln Leu Leu Leu Leu His Lys Ile His Ala
        115                 120                 125

Glu Pro Glu Ala Gln Gln Leu Gly
    130                 135

<210> SEQ ID NO 37
<211> LENGTH: 1446
<212> TYPE: DNA

-continued

```
<213> ORGANISM: not required under old rule
<220> FEATURE:
<221> NAME/KEY: CDS
<222> LOCATION: (1)..(1443)
<223> OTHER INFORMATION: prodict = "Coniferylaldehyd-Dehydrogenase" /
      gene = "caldh"

<400> SEQUENCE: 37 atg agc att ctt ggt ttg aat ggt gcc ccg gtc gga gct gag cag ctg      48
Met Ser Ile Leu Gly Leu Asn Gly Ala Pro Val Gly Ala Glu Gln Leu
 1               5                  10                  15 ggc tcg gct ctt gat cgc atg aag aag gcg cac ctg gag cag ggg cct      96
Gly Ser Ala Leu Asp Arg Met Lys Lys Ala His Leu Glu Gln Gly Pro
             20                  25                  30 gca aac ttg gag ctg cgt ctg agt agg ctg gat cgt gcg att gca atg     144
Ala Asn Leu Glu Leu Arg Leu Ser Arg Leu Asp Arg Ala Ile Ala Met
         35                  40                  45 ctt ctg gaa aat cgt gaa gca att gcc gac gcg gtt tct gct gac ttt     192
Leu Leu Glu Asn Arg Glu Ala Ile Ala Asp Ala Val Ser Ala Asp Phe
     50                  55                  60 ggc aat cgc agc cgt gag caa aca ctg ctt tgc gac att gct ggc tcg     240
Gly Asn Arg Ser Arg Glu Gln Thr Leu Leu Cys Asp Ile Ala Gly Ser
 65                  70                  75                  80 gtg gca agc ctg aag gat agc cgc gag cac gtg gcc aaa tgg atg gag     288
Val Ala Ser Leu Lys Asp Ser Arg Glu His Val Ala Lys Trp Met Glu
                 85                  90                  95 ccc gaa cat cac aag gcg atg ttt cca ggg gcg gag gca cgc gtt gag     336
Pro Glu His His Lys Ala Met Phe Pro Gly Ala Glu Ala Arg Val Glu
            100                 105                 110 ttt cag ccg ctg ggt gtc gtt ggg gtc att agt ccc tgg aac ttc cct     384
Phe Gln Pro Leu Gly Val Val Gly Val Ile Ser Pro Trp Asn Phe Pro
        115                 120                 125 atc gta ctg gcc ttt ggg ccg ctg gcc ggc ata ttc gca gca ggt aat     432
Ile Val Leu Ala Phe Gly Pro Leu Ala Gly Ile Phe Ala Ala Gly Asn
    130                 135                 140 cgc gcc atg ctc aag ccg tcc gag ctt acc ccg cgg act tct gcc ctg     480
Arg Ala Met Leu Lys Pro Ser Glu Leu Thr Pro Arg Thr Ser Ala Leu
145                 150                 155                 160 ctt gcg gag cta att gct cgt tac ttc gat gaa act gag ctg act aca     528
Leu Ala Glu Leu Ile Ala Arg Tyr Phe Asp Glu Thr Glu Leu Thr Thr
                165                 170                 175 gtg ctg ggc gac gct gaa gtc ggt gcg ctg ttc agt gct cag cct ttc     576
Val Leu Gly Asp Ala Glu Val Gly Ala Leu Phe Ser Ala Gln Pro Phe
            180                 185                 190 gat cat ctg atc ttc acc ggc ggc act gcc gtg gcc aag cac atc atg     624
Asp His Leu Ile Phe Thr Gly Gly Thr Ala Val Ala Lys His Ile Met
        195                 200                 205 cgt gcc gcg gcg gat aac cta gtg ccc gtt acc ctg gaa ttg ggt ggc     672
Arg Ala Ala Ala Asp Asn Leu Val Pro Val Thr Leu Glu Leu Gly Gly
    210                 215                 220 aaa tcg ccg gtg atc gtt tcc cgc agt gca gat atg gcg gac gtt gca     720
Lys Ser Pro Val Ile Val Ser Arg Ser Ala Asp Met Ala Asp Val Ala
225                 230                 235                 240 caa cgg gtg ttg acg gtg aaa acc ttc aat gcc ggg caa atc tgt ctg     768
Gln Arg Val Leu Thr Val Lys Thr Phe Asn Ala Gly Gln Ile Cys Leu
                245                 250                 255 gca ccg gac tat gtg ctg ctg ccg gaa gaa tcg ctg gat agc ttt gtc     816
Ala Pro Asp Tyr Val Leu Leu Pro Glu Glu Ser Leu Asp Ser Phe Val
            260                 265                 270 gcc gag gcg acg cgc ttc gtg gcc gca atg tat ccc tcg ctt cta gat     864
Ala Glu Ala Thr Arg Phe Val Ala Ala Met Tyr Pro Ser Leu Leu Asp
        275                 280                 285
```

-continued

| | | |
|---|---|---|
| aat ccg gat tac acg tcg atc atc aat gcc cga aat ttc gac cgt ctg<br>Asn Pro Asp Tyr Thr Ser Ile Ile Asn Ala Arg Asn Phe Asp Arg Leu<br>    290                       295                     300 | | 912 |
| cat cgc tac ctg act gat gcg cag gca aag gga ggg cgc gtc att gaa<br>His Arg Tyr Leu Thr Asp Ala Gln Ala Lys Gly Gly Arg Val Ile Glu<br>305                     310                     315                   320 | | 960 |
| atc aat cct gcg gcc gaa gag ttg ggg gat agt ggt atc agg aag atc<br>Ile Asn Pro Ala Ala Glu Glu Leu Gly Asp Ser Gly Ile Arg Lys Ile<br>                     325                     330                   335 | | 1008 |
| gcg ccc act ttg atc gtg aat gtg tcg gat gaa atg ctg gtc ttg aac<br>Ala Pro Thr Leu Ile Val Asn Val Ser Asp Glu Met Leu Val Leu Asn<br>             340                     345                   350 | | 1056 |
| gag gag atc ttt ggt ccg ctg ctc ccg atc aag act tat cgt gat ttc<br>Glu Glu Ile Phe Gly Pro Leu Leu Pro Ile Lys Thr Tyr Arg Asp Phe<br>           355                     360                   365 | | 1104 |
| gac tcg gct atc gac tac gtc aac agc aag cag cga cca ctt gcc tcg<br>Asp Ser Ala Ile Asp Tyr Val Asn Ser Lys Gln Arg Pro Leu Ala Ser<br>    370                     375                     380 | | 1152 |
| tac ttc ttc ggc gaa gat gcg gtt gag cgt gag caa gtg ctt aag cgt<br>Tyr Phe Phe Gly Glu Asp Ala Val Glu Arg Glu Gln Val Leu Lys Arg<br>385                     390                     395                   400 | | 1200 |
| acg gtt tcg ggc gcc gtg gtc gtg aac gat gtc atg agc cat gtg atg<br>Thr Val Ser Gly Ala Val Val Val Asn Asp Val Met Ser His Val Met<br>                     405                     410                   415 | | 1248 |
| atg gat acg ctt cca ttt ggt ggt gtg ggg cac tcg ggg atg ggg gca<br>Met Asp Thr Leu Pro Phe Gly Gly Val Gly His Ser Gly Met Gly Ala<br>             420                     425                   430 | | 1296 |
| tat cac ggc att tat ggt ttc cga acc ttc agc cat gcc aag cct gtt<br>Tyr His Gly Ile Tyr Gly Phe Arg Thr Phe Ser His Ala Lys Pro Val<br>           435                     440                   445 | | 1344 |
| ctc gtg caa agt cct gtg ggt gag tcg aac ttg gcg atg cgc gca ccc<br>Leu Val Gln Ser Pro Val Gly Glu Ser Asn Leu Ala Met Arg Ala Pro<br>    450                     455                     460 | | 1392 |
| tac gga gaa gcg atc cac gga ctg ctc tct gtc ctc ctt tca acg gag<br>Tyr Gly Glu Ala Ile His Gly Leu Leu Ser Val Leu Leu Ser Thr Glu<br>465                     470                     475                   480 | | 1440 |
| tgt tag<br>Cys | | 1446 |

<210> SEQ ID NO 38
<211> LENGTH: 481
<212> TYPE: PRT
<213> ORGANISM: not required under old rule

<400> SEQUENCE: 38

Met Ser Ile Leu Gly Leu Asn Gly Ala Pro Val Gly Ala Glu Gln Leu
 1               5                  10                  15

Gly Ser Ala Leu Asp Arg Met Lys Lys Ala His Leu Glu Gln Gly Pro
                20                  25                  30

Ala Asn Leu Glu Leu Arg Leu Ser Arg Leu Asp Arg Ala Ile Ala Met
            35                  40                  45

Leu Leu Glu Asn Arg Glu Ala Ile Ala Asp Ala Val Ser Ala Asp Phe
        50                  55                  60

Gly Asn Arg Ser Arg Glu Gln Thr Leu Leu Cys Asp Ile Ala Gly Ser
 65                  70                  75                  80

Val Ala Ser Leu Lys Asp Ser Arg Glu His Val Ala Lys Trp Met Glu
                85                  90                  95

```
Pro Glu His His Lys Ala Met Phe Pro Gly Ala Glu Ala Arg Val Glu
             100                 105                 110
Phe Gln Pro Leu Gly Val Val Gly Val Ile Ser Pro Trp Asn Phe Pro
         115                 120                 125
Ile Val Leu Ala Phe Gly Pro Leu Ala Gly Ile Phe Ala Ala Gly Asn
    130                 135                 140
Arg Ala Met Leu Lys Pro Ser Glu Leu Thr Pro Arg Thr Ser Ala Leu
145                 150                 155                 160
Leu Ala Glu Leu Ile Ala Arg Tyr Phe Asp Glu Thr Glu Leu Thr Thr
                165                 170                 175
Val Leu Gly Asp Ala Glu Val Gly Ala Leu Phe Ser Ala Gln Pro Phe
            180                 185                 190
Asp His Leu Ile Phe Thr Gly Gly Thr Ala Val Ala Lys His Ile Met
        195                 200                 205
Arg Ala Ala Asp Asn Leu Val Pro Val Thr Leu Glu Leu Gly Gly
    210                 215                 220
Lys Ser Pro Val Ile Val Ser Arg Ser Ala Asp Met Ala Asp Val Ala
225                 230                 235                 240
Gln Arg Val Leu Thr Val Lys Thr Phe Asn Ala Gly Gln Ile Cys Leu
                245                 250                 255
Ala Pro Asp Tyr Val Leu Leu Pro Glu Glu Ser Leu Asp Ser Phe Val
            260                 265                 270
Ala Glu Ala Thr Arg Phe Val Ala Ala Met Tyr Pro Ser Leu Leu Asp
        275                 280                 285
Asn Pro Asp Tyr Thr Ser Ile Ile Asn Ala Arg Asn Phe Asp Arg Leu
    290                 295                 300
His Arg Tyr Leu Thr Asp Ala Gln Ala Lys Gly Gly Arg Val Ile Glu
305                 310                 315                 320
Ile Asn Pro Ala Ala Glu Glu Leu Gly Asp Ser Gly Ile Arg Lys Ile
                325                 330                 335
Ala Pro Thr Leu Ile Val Asn Val Ser Asp Glu Met Leu Val Leu Asn
            340                 345                 350
Glu Glu Ile Phe Gly Pro Leu Leu Pro Ile Lys Thr Tyr Arg Asp Phe
        355                 360                 365
Asp Ser Ala Ile Asp Tyr Val Asn Ser Lys Gln Arg Pro Leu Ala Ser
    370                 375                 380
Tyr Phe Phe Gly Glu Asp Ala Val Glu Arg Glu Gln Val Leu Lys Arg
385                 390                 395                 400
Thr Val Ser Gly Ala Val Val Asn Asp Val Met Ser His Val Met
                405                 410                 415
Met Asp Thr Leu Pro Phe Gly Val Gly His Ser Gly Met Gly Ala
            420                 425                 430
Tyr His Gly Ile Tyr Gly Phe Arg Thr Phe Ser His Ala Lys Pro Val
        435                 440                 445
Leu Val Gln Ser Pro Val Gly Glu Ser Asn Leu Ala Met Arg Ala Pro
    450                 455                 460
Tyr Gly Glu Ala Ile His Gly Leu Leu Ser Val Leu Leu Ser Thr Glu
465                 470                 475                 480
Cys

<210> SEQ ID NO 39
<211> LENGTH: 1827
<212> TYPE: DNA
<213> ORGANISM: not required under old rule
```

<400> SEQUENCE: 39

```
ctatttgtct agtggtcggc gcgaaattcg ataagaaagc tgggcgcgag tgaggccgag      60
ccggcgggca gcttccgaga cattgccttt cacctggccc agagcatggc taatcatcgc     120
gtcctccact tcttgcagcg tcatcgcgct caggtccttt gagtcaagcg gcgagtcgat     180
tgtgctggtc ggtttggaga aggaagtact tgggctgcca gtttcctgtg gctgattatc     240
ttgagcggtg gccaggatgc cgctggcccc aatggagaac atcggttgag tcagtcgttc     300
accgctagtg aagaggtggc tcacgtcaat ggctccatcc tccggagcgc tgatgactcc     360
gcgctccacc aaattttgaa gctcccggat gtttcctgga agtcgtagc caagcagggc      420
attggctgca cgtggagtga atccgctgac cacccggcta tgacgctgat tgaagcggtg     480
caggaaatag gtcatcagga ggggaatgtc ttccttcctc tctcgaagcg gcgggaggtg     540
gatcgggtaa acattgaggc ggaaaaaaag gtcctcgcgg aactcgccgc gctggacgcc     600
tgcgcgaaga tcgacattgg ttgcggctac cacacggacg tcaaccttga gtgtcctgct     660
tccgccaacc cgttcgacct ccgactcttg cagggcgcga agtaacttcc cttgggccac     720
gaggcttagc gtccctatct cgtcaaggaa tagtgtgccg cccgaagcgc gctcgaaccg     780
tcctgctcga gattgggtgg cgccggtaaa cgccccccgt tcgacgccga acaactcgga     840
ctccatcagg gtttcgggaa tacgtgcgca attgaccgca acaaacgggc cgtcgtgtct     900
ggggctgatg cggtgaagca tgcgggcgaa catctccttg cccacacctg attcacccgt     960
aaacagtacc gtcgcctccg tgggtgctac gcgcttcagc atgtggcagg cagcattgaa    1020
tgccgaggaa attcccacca tgtcgtgttc cgatgcagtg cttgagtctg cggcggagtg    1080
atggggagtg ttcctttgtc cctgctgcgt tcttcgtctc tgcggcgtgc ttggttgccg    1140
acaaatggtt gcgctaagcg ccgccaagtc ctcttcggcg tcttcccatt cttccgctgg    1200
cttgccgatc atgcggcaga tctgcgaacc cgtggagcgg cattccacct ctcggtaaag    1260
gatgaggcga ccaaccagcg cggacgtata gccaatggca taacccgtct gcgtccagca    1320
cgcgggctcg gtgccgatgc cgtagtgcgc aatatgttca tcatcttcgc tcgaatggtg    1380
ccagaggaat tcgccgtagt aggtccccaa atccatgtcg aagtcgaagt ggatcggctc    1440
cacgcgtact gcgccttcca gagagtgcaa gttcgggccg gcggcaaata gggagagcgg    1500
atcggcgttg ctgaagcgct ccttcagaag ggcggcatct ttggcgccgc agtggtaacc    1560
ggttcgcagc atgattccgc gggcgcgggc gaagcccacg ctttcaatta attcgcgtcg    1620
caatgcaccc agtccgctgc tgtggaggag cagcattcgc gcgccgttca accagatgcg    1680
tccatcgcca gggctgaaaa ggagggattc agtgaggtca tgaagggagg ggacggcgcc    1740
tggctccaat tgctcgatgg cgccgcgatt gagtgtcttg gcgcggtct tggagagttc      1800
ggctagggag ataaatttgc tggccat                                       1827
```

<210> SEQ ID NO 40
<211> LENGTH: 608
<212> TYPE: PRT
<213> ORGANISM: not required under old rule

<400> SEQUENCE: 40

```
Met Ala Ser Lys Phe Ile Ser Leu Ala Glu Leu Ser Lys Thr Ala Pro
 1               5                  10                  15

Lys Thr Leu Asn Arg Gly Ala Ile Glu Gln Leu Glu Pro Gly Ala Val
            20                  25                  30
```

```
Pro Ser Leu His Asp Leu Thr Glu Ser Leu Leu Phe Ser Pro Gly Asp
         35                  40                  45

Gly Arg Ile Trp Leu Asn Gly Ala Arg Met Leu Leu Leu His Ser Ser
 50                  55                  60

Gly Leu Gly Ala Leu Arg Arg Glu Leu Ile Glu Ser Val Gly Phe Ala
 65                  70                  75                  80

Arg Ala Arg Gly Ile Met Leu Arg Thr Gly Tyr His Cys Gly Ala Lys
             85                  90                  95

Asp Ala Ala Leu Leu Lys Glu Arg Phe Ser Asn Ala Asp Pro Leu Ser
                100                 105                 110

Leu Phe Ala Ala Gly Pro Asn Leu His Ser Leu Glu Gly Ala Val Arg
        115                 120                 125

Val Glu Pro Ile His Phe Asp Phe Asp Met Asp Leu Gly Thr Tyr Tyr
    130                 135                 140

Gly Glu Phe Leu Trp His His Ser Ser Glu Asp Asp Glu His Ile Ala
145                 150                 155                 160

His Tyr Gly Ile Gly Thr Glu Pro Ala Cys Trp Thr Gln Thr Gly Tyr
                165                 170                 175

Ala Ile Gly Tyr Thr Ser Ala Leu Val Gly Arg Leu Ile Leu Tyr Arg
            180                 185                 190

Glu Val Glu Cys Arg Ser Thr Gly Ser Gln Ile Cys Arg Met Ile Gly
    195                 200                 205

Lys Pro Ala Glu Glu Trp Glu Asp Ala Glu Glu Asp Leu Ala Ala Leu
    210                 215                 220

Ser Ala Thr Ile Cys Arg Gln Pro Ser Thr Pro Gln Arg Arg Arg Thr
225                 230                 235                 240

Gln Gln Gly Gln Arg Asn Thr Pro His His Ser Ala Ala Asp Ser Ser
                245                 250                 255

Thr Ala Ser Glu His Asp Met Val Gly Ile Ser Ser Ala Phe Asn Ala
                260                 265                 270

Ala Cys His Met Leu Lys Arg Val Ala Pro Thr Glu Ala Thr Val Leu
        275                 280                 285

Phe Thr Gly Glu Ser Gly Val Gly Lys Glu Met Phe Ala Arg Met Leu
290                 295                 300

His Arg Ile Ser Pro Arg His Asp Gly Pro Phe Val Ala Val Asn Cys
305                 310                 315                 320

Ala Arg Ile Pro Glu Thr Leu Met Glu Ser Glu Leu Phe Gly Val Glu
                325                 330                 335

Arg Gly Ala Phe Thr Gly Ala Thr Gln Ser Arg Ala Gly Arg Phe Glu
            340                 345                 350

Arg Ala Ser Gly Gly Thr Leu Phe Leu Asp Glu Ile Gly Thr Leu Ser
        355                 360                 365

Leu Val Ala Gln Gly Lys Leu Leu Arg Ala Leu Gln Glu Ser Glu Val
    370                 375                 380

Glu Arg Val Gly Gly Ser Arg Thr Leu Lys Val Asp Val Arg Val Val
385                 390                 395                 400

Ala Ala Thr Asn Val Asp Leu Arg Ala Gly Val Gln Arg Gly Glu Phe
                405                 410                 415

Arg Glu Asp Leu Phe Phe Arg Leu Asn Val Tyr Pro Ile His Leu Pro
            420                 425                 430

Pro Leu Arg Glu Arg Lys Glu Asp Ile Pro Leu Leu Met Thr Tyr Phe
        435                 440                 445

Leu His Arg Phe Asn Gln Arg His Ser Arg Val Val Ser Gly Phe Thr
```

```
                  450              455              460
Pro Arg Ala Ala Asn Ala Leu Leu Gly Tyr Asp Phe Pro Gly Asn Ile
465             470              475             480

Arg Glu Leu Gln Asn Leu Val Glu Arg Gly Val Ile Ser Ala Pro Glu
                485              490             495

Asp Gly Ala Ile Asp Val Ser His Leu Phe Thr Ser Gly Glu Arg Leu
            500              505             510

Thr Gln Pro Met Phe Ser Ile Gly Ala Ser Gly Ile Leu Ala Thr Ala
            515             520             525

Gln Asp Asn Gln Pro Gln Glu Thr Gly Ser Pro Ser Thr Ser Phe Ser
        530             535             540

Lys Pro Thr Ser Thr Ile Asp Ser Pro Leu Asp Ser Lys Asp Leu Ser
545             550             555             560

Ala Met Thr Leu Gln Glu Val Glu Asp Ala Met Ile Ser His Ala Leu
                565             570             575

Gly Gln Val Lys Gly Asn Val Ser Glu Ala Ala Arg Arg Leu Gly Leu
                580             585             590

Thr Arg Ala Gln Leu Ser Tyr Arg Ile Ser Arg Arg Pro Leu Asp Lys
            595             600             605

<210> SEQ ID NO 41
<211> LENGTH: 768
<212> TYPE: DNA
<213> ORGANISM: not required under old rule
<220> FEATURE:
<221> NAME/KEY: CDS
<222> LOCATION: (1)..(765)
<223> OTHER INFORMATION: product = "Coniferylalkohol-Dehydrogenase" /
      gene = "cadh"

<400> SEQUENCE: 41 atg caa ctg acc aac aag aaa atc gtc gtc acc gga gtg tcc tcc ggt     48
Met Gln Leu Thr Asn Lys Lys Ile Val Val Thr Gly Val Ser Ser Gly
 1               5                  10                  15 atc ggt gcc gaa act gcc cgc gtt ctg cgc tct cac ggc gcc aca gtg     96
Ile Gly Ala Glu Thr Ala Arg Val Leu Arg Ser His Gly Ala Thr Val
             20                  25                  30 att ggc gta gat cgc aac atg ccg agc ctg act ctg gat gct ttc gtt    144
Ile Gly Val Asp Arg Asn Met Pro Ser Leu Thr Leu Asp Ala Phe Val
         35                  40                  45 cag gct gac ctg agc cat cct gaa ggc atc gat aag gcc atc tct cag    192
Gln Ala Asp Leu Ser His Pro Glu Gly Ile Asp Lys Ala Ile Ser Gln
     50                  55                  60 ctg ccg gag aaa att gac gga ctc tgc aat atc gcc ggg gtg ccc ggc    240
Leu Pro Glu Lys Ile Asp Gly Leu Cys Asn Ile Ala Gly Val Pro Gly
 65                  70                  75                  80 act gcc gat cct cag ctc gtc gca aac gtg aac tac ctg ggt cta aag    288
Thr Ala Asp Pro Gln Leu Val Ala Asn Val Asn Tyr Leu Gly Leu Lys
                 85                  90                  95 tat ctg acc gag gca gtc ctg tcg cgc att caa ccc ggt ggt tcg att    336
Tyr Leu Thr Glu Ala Val Leu Ser Arg Ile Gln Pro Gly Gly Ser Ile
            100                 105                 110 gtc aac gtg tcc tct gtg ctt ggc gcc gag tgg ccg gcc cgc ctt cag    384
Val Asn Val Ser Ser Val Leu Gly Ala Glu Trp Pro Ala Arg Leu Gln
        115                 120                 125 ttg cat aag gag ctg ggg agt gtt gtt gga ttc tcc gaa ggc cag gca    432
Leu His Lys Glu Leu Gly Ser Val Val Gly Phe Ser Glu Gly Gln Ala
    130                 135                 140 tgg ctt aag cag aat cca gtg gcc ccc gaa ttc tgc tac cag tat ttc    480
```

-continued

```
Trp Leu Lys Gln Asn Pro Val Ala Pro Glu Phe Cys Tyr Gln Tyr Phe
145                 150                 155                 160 aaa gaa gca ctg atc gtt tgg tct caa gtt cag gcg cag gaa tgg ttc       528
Lys Glu Ala Leu Ile Val Trp Ser Gln Val Gln Ala Gln Glu Trp Phe
                165                 170                 175 atg agg acg tct gta cgc atg aac tgc atc gcc ccc ggc cct gta ttc       576
Met Arg Thr Ser Val Arg Met Asn Cys Ile Ala Pro Gly Pro Val Phe
            180                 185                 190 act ccc att ctc aat gag ttc gtc acc atg ctg ggt caa gag cgg act       624
Thr Pro Ile Leu Asn Glu Phe Val Thr Met Leu Gly Gln Glu Arg Thr
        195                 200                 205 cag gcg gac gct cat cgt att aag cgc cca gca tat gcc gat gaa gtg       672
Gln Ala Asp Ala His Arg Ile Lys Arg Pro Ala Tyr Ala Asp Glu Val
    210                 215                 220 gcc gcg gtg att gca ttc atg tgt gct gag gag tca cgt tgg atc aac       720
Ala Ala Val Ile Ala Phe Met Cys Ala Glu Glu Ser Arg Trp Ile Asn
225                 230                 235                 240 ggc ata aat att cca gtg gac gga ggt ttg gca tcg acc tac gtg taa       768
Gly Ile Asn Ile Pro Val Asp Gly Gly Leu Ala Ser Thr Tyr Val
                245                 250                 255
```

<210> SEQ ID NO 42
<211> LENGTH: 255
<212> TYPE: PRT
<213> ORGANISM: not required under old rule

<400> SEQUENCE: 42

```
Met Gln Leu Thr Asn Lys Lys Ile Val Val Thr Gly Val Ser Ser Gly
  1               5                  10                  15

Ile Gly Ala Glu Thr Ala Arg Val Leu Arg Ser His Gly Ala Thr Val
                 20                  25                  30

Ile Gly Val Asp Arg Asn Met Pro Ser Leu Thr Leu Asp Ala Phe Val
             35                  40                  45

Gln Ala Asp Leu Ser His Pro Glu Gly Ile Asp Lys Ala Ile Ser Gln
         50                  55                  60

Leu Pro Glu Lys Ile Asp Gly Leu Cys Asn Ile Ala Gly Val Pro Gly
 65                  70                  75                  80

Thr Ala Asp Pro Gln Leu Val Ala Asn Val Asn Tyr Leu Gly Leu Lys
                 85                  90                  95

Tyr Leu Thr Glu Ala Val Leu Ser Arg Ile Gln Pro Gly Gly Ser Ile
                100                 105                 110

Val Asn Val Ser Ser Val Leu Gly Ala Glu Trp Pro Ala Arg Leu Gln
            115                 120                 125

Leu His Lys Glu Leu Gly Ser Val Gly Phe Ser Glu Gly Gln Ala
        130                 135                 140

Trp Leu Lys Gln Asn Pro Val Ala Pro Glu Phe Cys Tyr Gln Tyr Phe
145                 150                 155                 160

Lys Glu Ala Leu Ile Val Trp Ser Gln Val Gln Ala Gln Glu Trp Phe
                165                 170                 175

Met Arg Thr Ser Val Arg Met Asn Cys Ile Ala Pro Gly Pro Val Phe
            180                 185                 190

Thr Pro Ile Leu Asn Glu Phe Val Thr Met Leu Gly Gln Glu Arg Thr
        195                 200                 205

Gln Ala Asp Ala His Arg Ile Lys Arg Pro Ala Tyr Ala Asp Glu Val
    210                 215                 220

Ala Ala Val Ile Ala Phe Met Cys Ala Glu Glu Ser Arg Trp Ile Asn
225                 230                 235                 240
```

```
Gly Ile Asn Ile Pro Val Asp Gly Gly Leu Ala Ser Thr Tyr Val
            245                 250                 255

<210> SEQ ID NO 43
<211> LENGTH: 26
<212> TYPE: DNA
<213> ORGANISM: not required under old rule

<400> SEQUENCE: 43
atgcarctba cbaayaaraa ratygt                                    26

<210> SEQ ID NO 44
<211> LENGTH: 20
<212> TYPE: PRT
<213> ORGANISM: not required under old rule
<220> FEATURE:
<221> NAME/KEY: UNSURE
<222> LOCATION: (12)
<221> NAME/KEY: UNSURE
<222> LOCATION: (13)..(19)

<400> SEQUENCE: 44

Met Gln Leu Thr Asn Lys Lys Ile Val Val Xaa Val Xaa Xaa Xaa
  1               5                  10                  15

Xaa Xaa Xaa Xaa
            20

<210> SEQ ID NO 45
<211> LENGTH: 20
<212> TYPE: PRT
<213> ORGANISM: not required under old rule
<220> FEATURE:
<221> NAME/KEY: UNSURE
<222> LOCATION: (20)

<400> SEQUENCE: 45

Ser Ile Leu Gly Leu Asn Gly Ala Pro Val Gly Ala Glu Gln Leu Gly
  1               5                  10                  15

Ser Ala Leu Xaa
            20
```

SYNTHETIC ENZYMES FOR THE PRODUCTION OF CONIFERYL ALCOHOL, CONIFERYLALDEHYDE, FERULIC ACID, VANILLIN AND VANILLIC ACID AND THEIR USE

The present invention relates to synthesis enzymes for the production of coniferyl alcohol, coniferylaldehyde, ferulic acid, vanillin and vanillic acid, the use thereof for the production of coniferyl alcohol, coniferylaldehyde, ferulic acid, vanillin and vanillic acid, DNA coding for the aforementioned enzymes and microorganisms transformed therewith.

The first article relating to the degradation of eugenol was written by Tadasa in 1977 (Degradation of eugenol by a microorganism. Agric. Biol. Chem. 41, 925–929). It describes the degradation of eugenol with a soil isolate which was presumed to be Corynebacterium sp. In this process ferulic acid and vanillin were identified as intermediate degradation products and the subsequent degradation was assumed to proceed via vanillic acid and protocatechuic acid.

In 1983 another article by Tadasa and Kyahara appeared (Initial Steps of Eugenol Degradation Pathway of a Microorganism. Agric. Biol. Chem. 47, 2639–2640) on the initial steps of eugenol degradation, this time with a soil isolate which was identified to be Pseudomonas sp. In this article eugenol oxide, coniferyl alcohol and coniferylaldehyde were described as intermediates for the formation of ferulic acid.

Also in 1983 a report by Sutherland et al. appeared (Metabolism of cinnamic, p-coumaric, and ferulic acids by *Streptomyces setonii*. Can. J. Microbiol. 29, 1253–1257) on the metabolism of cinnamic, p-coumaric and ferulic acids by *Streptomyces setonii*. In this process ferulic acid was degraded via vanillin, vanillic acid and protocatechuic acid, the ring-cleaving enzymes catechol 1,2-dioxygenase and protocatechuate 3,4-dioxygenase having been indirectly identified in the cell-free extract.

In 1985 Ötük (Degradation of Ferulic Acid by *Escherichia coli*. J. Ferment. Technol. 63, 501–506) reported on the degradation of ferulic acid by a strain of *Escherichia coli* isolated from decaying bark. Here as well vanillin, vanillic acid and protocatechuic acid were found as degradation products.

In 1987 a German patent application by BASF appeared ["Verfahren zur Gewinnung von Coniferylaldehyd und Mikroorganismus dafur" (A process for obtaining coniferylaldehyde and a microorganism therefor); DE-A 3 606 398] for a process for producing coniferylaldehyde from eugenol using a mutant of *Arthrobacter globiformis*. The aim was to obtain natural vanillin.

Abraham et al. (Microbial transformations of some terpenoids and natural compounds: Bioflavour '87, pp. 399–413) reported at "Bioflavor '87" on the metabolisation of eugenol by various microorganisms. When fungi were used, dimers were predominantly found and only when isoeugenol was used *Aspergillus niger* ATCC 9142 did also form vanillin.

In 1988 Omori et al. described a process (Protocatechuic acid production from trans-ferulic acid by Pseudomonas sp. HF-1 mutants defective in protocatechuic acid catabolism. Appl. Microbiol. Biotechnol. 29, 497–500) for obtaining protocatechuic acid with a mutant of a Pseudomonas sp. HF-1. The only intermediate mentioned was vanillic acid.

In 1989 the metabolism of ferulic acid by two fungi, *Paecilomyces variotii* and *Pestalotia palmarum* was described by Rahouti et al. (Metabolism of ferulic acid by *Paecilomyces variotii* and *Pestalotia palmarum*. Appl. Environ. Microbiol. 55, 2391–2398). It was postulated that degradation to form vanillic acid proceeded via 4-vinylguaiacol and vanillin.

In 1990 two Japanese patent applications by Hasegawa appeared on a new Pseudomonas sp. and a dioxygenase enzyme (Novel Pseudomonas sp. and dioxygenase enzyme. JP 2195-871:25.10.88-JP-267 284 (2.8.90) 9.3.89 as 055111) and on a new method for the production of an aldehyde such as for example vanillin (A new method for the preparation of aldehyde e.g. vanillin. JP 2200-192:25.10.88-JP-267 285 (8.8.90) 9.3.89 as 055112). The method is however not based on eugenol but on various starting compounds such as isoeugenol and coniferyl alcohol. Nor is there any identity between the dioxygenase claimed in the aforementioned patent applications and the enzymes claimed in the present application.

Bacteria of the genera Serratia, Enterobacter or Klebsiella were used in EP-A 405 197 (Production of natural vanillin by microbial oxidation of eugenol or isoeugenol) for the microbial oxidation of eugenol and isoeugenol. However, only when isoeugenol was used the process did produce high conversion rates; the results were very poor using eugenol.

In 1991 EP-A 453 368 appeared ["Production de vanilline par bioconversion de précurseurs benzeniques" (Production of vanillin by the bioconversion of benzene precursors)], in which the reaction to form vanillin from vanillic acid and ferulic acid using a basidiomycete— *Pycnoporus cinnabarinus* CNCM I-937 and I-938—was observed.

In 1992 the Takasago Perfumery Company was granted a Japanese patent (Preparation of vanillin, coniferyl-alcohol and -aldehyde, ferulic acid and vanillyl alcohol—by culturing mutant belonging to Pseudomonas genus in presence of eugenol which is oxidatively decomposed; JP 05 227 980 21.1.1992) for the preparation of vanillin, coniferyl alcohol, coniferylaldehyde, ferulic acid and vanillyl alcohol from eugenol using a Pseudomonas mutant.

Also in 1992 U.S. Pat. No. 5,128,253 by Labuda et al. (Kraft General Foods) (Bioconversion process for the production of vanillin) was granted, in which a biotransformation process for the production of vanillin was described. Here as well the starting material was ferulic acid and the organisms used were *Aspergillus niger, Rhodotorula glutinis* and *Corynebacterium glutamicum*. The crucial feature was the use of sulphydryl components (e.g. dithiothreitol) in the medium. In 1993 the subject matter of the patent also appeared in the form of a publication (Microbial bioconversion process for the production of vanillin; Prog. Flavour Precursor Stud. Proc. Int. Conf. 1992, 477–482).

EP-A 542 348 (Process for the preparation of phenylaldehydes) describes a process for the preparation of phenylaldehydes in the presence of the enzyme lipoxygenase. Eugenol and isoeugenol are for example used as substrates. We have attempted to rework the process using eugenol, but have not succeeded in confirming the results of the reactions.

DE-A 4 227 076 [Verfahren zur Herstellung substituiterter Methoxyphenole und dafür geeigneter Mikroorganismus (Process for the production of substituted methoxyphenols and a microorganism suitable for said process)] describes the production of substituted methoxyphenols with a new Pseudomonas sp. The starting material used is eugenol and the products are ferulic acid, vanillic acid, coniferyl alcohol and coniferylaldehyde.

Also in 1995 a comprehensive review by Rosazza et al. (Biocatalytic transformation of ferulic acid: an abundant aromatic natural product; J. Ind. Microbiol. 15, 457–471) appeared on possible methods of biotransformation using ferulic acid.

Figure 1:
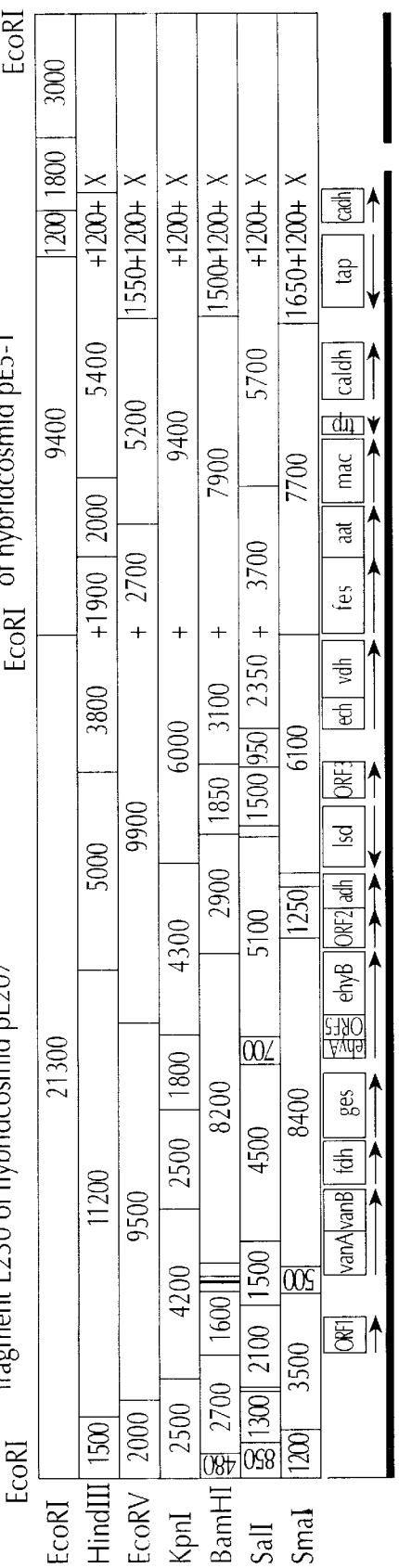
FIG. 1 is a physical map of cloned fragments, subfragments, and sequenced areas.

The present invention relates to synthetic enzymes for the production of coniferyl alcohol, coniferylaldehyde, ferulic acid, vanillin and vanillic acid from eugenol.

Synthetic enzymes according to the invention are for example:

a) eugenol hydroxylase,
b) coniferyl alcohol dehydrogenase,
c) coniferylaldehyde dehydrogenase,
d) ferulic acid deacylase and
e) vanillin dehydrogenase.

The invention also relates to DNA coding for the above-mentioned enzymes and cosmid clones containing this DNA as well as vectors containing this DNA and microorganisms transformed with the DNA or the vectors. It also relates to the use of the DNA for the transformation of microorganisms for the production of coniferyl alcohol, coniferylaldehyde, ferulic acid, vanillin and vanillic acid. The invention also relates to partial sequences of the DNA and functional equivalents. Functional equivalents are understood to be those derivatives in which individual nucleobases have been substituted (wobble substitutions) without resulting in any functional changes. In relation to proteins, amino acids can also be substituted without resulting in any functional changes.

The invention also relates to the individual steps for the production of coniferyl alcohol, coniferylaldehyde, ferulic acid, vanillin and vanillic acid from eugenol, i.e. in concrete terms:

a) the process for the production of coniferyl alcohol from eugenol carried out in the presence of eugenol hydroxylase;
b) the process for the production of coniferylaldehyde from coniferyl alcohol carried out in the presence of coniferyl alcohol dehydrogenase;
c) the process for the production of ferulic acid from coniferylaldehyde carried out in the presence of coniferylaldehyde dehydrogenase;
d) the process for the production of vanillin from ferulic acid carried out in the presence of ferulic acid deacylase;
e) the process for the production of vanillic acid from vanillin carried out in the presence of vanillin dehydrogenase.

After NMG mutagenesis mutants with defects in individual stages of the catabolism of eugenol were obtained from the eugenol-utilising Pseudomonas sp. strain HR 199 (DSM 7063). Using total DNA of wild-type Pseudomonas sp. HR 199 partially digested with EcoRI a gene library was constructed in the pVK100 cosmid, which has a broad host spectrum and can also be replicated in stable form in pseudomonads. After packaging in 1-phage particles the hybrid cosmids were transduced to *E. coli* S17-1. The gene library comprised 1330 recombinant *E. coli* S17-1 clones. The hybrid cosmid of each clone was transferred by conjugation into two eugenol-negative mutants (mutants 6164 and 6165) of the Pseudomonas sp. HR 199 strain and tested for a possible capacity for complementation. In this test two hybrid cosmids (pE207 and pE115) were identified, the obtainment of which restored mutant 6165's capacity to utilise eugenol. One hybrid cosmid (pE5-1) resulted in the complementation of mutant 6164.

The complementing capacity of plasmids pE207 and pE115 was attributed to a 23 kbp EcoRI fragment (E230). A physical map of this fragment was prepared and the fragment completely sequenced. The genes vanA and vanB which code for vanillate demethylase were localised in a 11.2 kbp HindIII subfragment (H110).

Another open reading frame (ORF) was found to be homologous to g-glutamyl cysteine synthetase produced by *Escherichia coli*. An additional ORF, which was homologous to formaldehyde dehydrogenases, was identified between the aforementioned ORF and the vanB gene. Two additional ORF's were found to be homologous to the cytochrome C subunit or the flavoprotein subunit of p-cresol methylhydroxylase, respectively produced by *Pseudomonas putida*. In the Pseudomonas sp. HR 199 strain, these ORF's code for a new not previously described eugenol hydroxylase which converts eugenol into coniferyl alcohol via a quinone methide derivative by a process analogous to the reaction mechanism of p-cresol methyl hydroxylase. Another ORF of an unknown function was identified between the genes of the two subunits of eugenol hydroxylase. An ORF which was homologous to lignostilbene-a,b-dioxygenase was identified in a 5.0 kbp HindIII subfragment (H50). In addition one ORF was identified which was homologous to alcohol dehydrogenases. The structural gene vdh of vanillin dehydrogenase was identified in a 3.8 kbp HindIII/EcoRI subfragment. Upstream of this gene an ORF was localised which was homologous to enoyl-CoA hydratases produced by various organisms.

The complementing capacity of plasmid pE5-1 was attributed to the joint obtainment of the 1.2 and 1.8 kbp EcoRI fragments (E12 and E18). Fragment E 12 was completely, and fragment E 18 partially, sequenced. The structural gene cadh of coniferyl alcohol dehydrogenase, which contained an EcoRI cleavage site, was localised in these fragments. Using chromatographic methods the enzyme was isolated from the soluble fraction of the crude extract of cells of Pseudomonas sp. HR 199 grown on eugenol. An oligonucleotide sequence was deduced from the specific N-terminal amino acid sequence. A corresponding DNA probe hybridised with fragment E12, in which the region of the cadh gene encoding the N-terminus was localised.

A eugenol- and ferulic acid-negative mutant (mutant 6167) was complemented by obtaining a 9.4 kbp EcoRI fragment (E 94) of the hybrid cosmid pE5-1. A physical map of this fragment was prepared. The complementing property was localised in a 1.9 kbp EcoRI/HindIII subfragment. This fragment had incomplete ORF's (they extended beyond the EcoRI and HindIII cleavage sites) which were homologous to acetyl-CoA acetyl transferases of various organisms and to the "medium-chain acyl-CoA synthetase" produced by *Pseudomonas oleovorans*. Fragment E 94 was completely sequenced. Downstream of the aforementioned ORF's an ORF was located which was homologous to β-ketothiolases. The structural gene of coniferylaldehyde dehydrogenase (caldh) was localised in a central position of fragment E 94. Using chromatographic methods the enzyme was isolated from the soluble fraction of the crude extract of cells of Pseudomonas sp. HR 199 grown on eugenol.

The conjugative transfer of hybrid cosmid pE207 into a large number of Pseudomonas strains resulted in the heterologous expression of the van A, van B and vdh genes and the eugenol-hydroxylase genes in the transconjugants obtained. The obtainment of the plasmid of one strain allowed it to grow using eugenol as its carbon and energy source.

Materials and Methods

Growth conditions of the bacteria. Strains of *Escherichia coli* were grown at 37° C. in a Luria-Bertani (LB) or M9 mineral medium (Sambrook, J. E. F. Fritsch and T. Maniatis. 1989. Molecular cloning: a laboratory manual. 2nd Edition, Cold Spring Harbor Laboratory Press, Cold Spring Harbor, N.Y.). Strains of Pseudomonas sp. and *Alcaligenes eutrophus* were grown at 30° C. in a nutrient broth (NB, 0.8% by weight) or in a mineral medium (MM) (Schlegel, H. G. et al. 1961. Arch. Mikrobiol. 38: 209–222). Ferulic acid, vanillin, vanillic acid and protocatechuic acid were dissolved in dimethyl sulphoxide and added to the respective medium in a final concentration of 0.1% by weight. Eugenol was added to the medium directly in a final concentration of 0.1 vol.-%, or applied on filter paper (circular filters 595, Schleicher & Schuell, Dassel, Germany) to the lids of MM agar plates. For the growth of transconjugants of Pseudomonas sp., tetracyline and kanamycin were used in final concentrations of 25 µg/ml and 300 µg/ml, respectively.

Nitrosoguanidine mutagenesis. The nitrosoguanidine mutagenesis of Pseudomonas sp. HR 199 was carried out using a modified method according to Miller (Miller, J. H. 1972. Experiments in molecular genetics. Cold Spring Harbor Laboratory, Cold Spring Harbor, N.Y.). Instead of the citrate buffer, a potassium phosphate (PP) buffer (100 mM, pH 7.0) was used. The final concentration of N-methyl-N'-nitro-N-nitrosoguanidine was 200 µg/ml. The mutants obtained were screened with regard to the loss of their capacity to utilise eugenol, ferulic acid, vanillin and vanillic acid as growth substrates.

Qualitative and quantitative detection of metabolic intermediates in culture supernatants. Culture supernatants were analysed by high-pressure liquid chromatography (Knauer HPLC) either directly or after dilution with twice-distilled water. Chromatography was carried out on Nucleosil-100 C18 (7 µm, 250×4 mm). The solvent used was 0.1 vol.-% formic acid and acetonitrile.

Purification of coniferyl alcohol dehydrogenase and coniferylaldehyde dehydrogenase. The purification processes were carried out at 4° C.

Crude extract. Cells of Pseudomonas sp. HR 199 grown on eugenol were washed in a 10 mM sodium phosphate buffer with a pH of 7.5, resuspended in the same buffer and disrupted by being passed through a French press (Amicon, Silver Spring, Md., USA) twice at a pressure of 1,000 psi. The cell homogenate was subjected to ultracentrifugation (1 h, 100,000×g, 4° C.), the soluble fraction of the crude extract being obtained as the supernatant.

Anion exchange chromatography on DEAE Sephacel. The soluble fraction of the crude extract was dialysed overnight against a 10 mM sodium phosphate buffer with a pH of 7.5 containing 100 mM NaCl. The dialysate was applied to a DEAE Sephacel column (2.6 cm×35 cm, bed volumn [BV]: 186 ml) equilibrated with a 10 mM sodium phosphate buffer of a pH of 7.5 containing 100 mM NaCl at a flow rate of 0.8 ml/min. The column was washed with two bed volumes of a 10 mM sodium phosphate buffer with a pH of 7.5 containing 100 mM NaCl. The elution of coniferyl alcohol dehydrogenase (CADH) and coniferylaldehyde dehydrogenase (CALDH) was carried out with a linear salt gradient of 100 to 500 mM NaCl in a 10 mM sodium phosphate buffer with a pH of 7.5 (2×150 ml). 5 ml fractions were collected. Fractions with high CADH and CALDH activities were combined in the corresponding DEAE pools respectively.

Gel filtration chromatography on Sephadex G200. The CADH DEAE pool was concentrated in a 50 ml Amicon ultrafiltration chamber via a Diaflo ultrafiltration membrane PM 30 (both from AMICON CORP., Lexington, USA) at a pressure of 290 kPa to a volume corresponding to approx. 2% of the Sephadex G200-BV. The concentrated protein solution was applied to a Sephadex G200 column (BV: 138 ml) equilibrated with a 10 mM sodium phosphate buffer with a pH of 7.5 containing 100 mM NaCl and eluted with the same buffer at a flow rate of 0.2 ml/min. 2 ml fractions were collected. Fractions with a high CADH activity were combined in the Sephadex G200 pool.

Hydrophobic interaction chromatography on butyl Sepharose 4B. The CADH Sephadex G200 pool was adjusted to 3 M NaCl and then applied to a butyl Sepharose 4B column (BV: 48 ml) equilibrated with a 10 mM sodium phosphate buffer with a pH of 7.5 containing 3 M NaCl (flow rate: 0.5 ml/min). The column was then washed with 2 BV of a 10 mM sodium phosphate buffer with a pH of 7.5 containing 3 M NaCl (flow rate: 1.0 ml/min). CADH was eluted with a linearly decreasing NaCl gradient of 3 to 0 M NaCl in a 10 mM sodium phosphate buffer with a pH of 7.5 (2×50 ml). 4 ml fractions were collected. Fractions with a high CADH activity were combined in the HIC pool and concentrated as described above.

Chromatography on hydroxyapatite. The CALDH DEAE pool was concentrated to 10 ml in a 50 ml Amicon ultrafiltration chamber via a Diaflo ultrafiltration membrane PM 30 (both from AMICON CORP., Lexington, USA) at a pressure of 290 kPa. The concentrated protein solution was applied to a hydroxyapatite column (BV: 80 ml) equilibrated with a buffer (10 mM NaCl in a 10 mM sodium phosphate buffer with a pH of 7.0) (flow rate: 2 ml/min). The column was then washed with 2.5 bed volumes of a buffer (flow rate: 2 ml/min). CALDH was eluted with a linearly increasing sodium phosphate gradient of 10 to 400 mM NaP (in each case containing 10 mM NaCL) (2×100 ml). 10 ml fractions were collected. Fractions with high CALDH activity were combined in the CALDH HA pool.

Gel filtration chromatography on Superdex HR 200 10/30. The CALDH HA pool was concentrated to 200 µl (Amicon ultrafiltration chamber, ultrafiltration membrane PM 30) and applied to a Superdex HR 200 10/30 column (BV: 23.6 ml) equilibrated with a 10 mM sodium phosphate buffer with a pH of 7.0. CALDH was eluted with the same buffer at a flow rate of 0.5 ml/min. 250 µl fractions were collected. Fractions with high CALDH activity were combined in the CALDH Superdex pool.

Determination of coniferyl alcohol dehydrogenase activity. The CADH activity was determined at 30° C. by means of an optical enzymatic test according to Jaeger et al. (Jaeger, E., L. Eggeling and H. Sahm. 1982. Current Microbiology. 6: 333–336) with the aid of a ZEISS PM 4 spectrophotometer fitted with a TE converter (both from ZEISS, Oberkochen, Germany) and a recorder. The reaction mixture with a volume of 1 ml contained 0.2 mmol of Tris/HCl (pH 9.0), 0.4 µmol of coniferyl alcohol, 2 µmol of AND, 0.1 mmol of semicarbazide and a solution of the enzyme ("Tris"=tris(hydroxymethyl)-aminomethane). The reduction of AND was monitored at 1=340 nm (e=6,3 $cm^2/\mu mol$). The enzyme activity was recorded in units (U), 1 U corresponding to that quantity of enzyme which metabolises 1 µmol of substrate per minute. The protein concentrations in the samples were determined according to the method described by Lowry et al. (Lowry, O. H., N. J. Rosebrough, A. L. Farr and R. J. Randall. 1951. J. Biol. Chem. 193: 265–275).

Determination of the coniferylaldehyde dehydrogenase activity. The CALDH activity was determined at 30° C. by an optical enzymatic test with the aid of a ZEISS PM 4 spectrophotometer fitted with a TE converter (both from ZEISS, Oberkochen, Germany) and a recorder. The reaction mixture of a volume of 1 ml contained a 10 mM Tris/HCl buffer (pH 8.8), 5.6 mM coniferylaldehyde, 3 mM AND and a solution of the enzyme. The oxidation of coniferylaldehyde to form ferulic acid was monitored at 1=400 nm (e=34 $cm^2/\mu mol$). The enzyme activity was recorded in units (U), 1 U corresponding to that quantity of enzyme which metabolises 1 $\mu mol$ of substrate per minute. The protein concentration in the samples was determined according to the method described by Lowry et al. (Lowry, O. H., N. J. Rosebrough, A. L. Farr and R. J. Randall. 1951. J. Biol. Chem. 193: 265–275).

Electrophoretic methods. The separation of protein-containing extracts was carried out in 7.4% by weight polyacrylamide gels under native conditions according to the method described by Stegemann et al. (Stegemann et al. 1973. Z. Naturforsch. 28c: 722–732) and under denaturing conditions in 11.5% by weight polyacrylamide gels according to the method described by Laemmli (Laemmli, U. K. 1970. Nature (London) 227: 680–685). Serva Blue R was used for non-specific protein staining. For specifically staining coniferyl alcohol, coniferylaldehyde and vanillin dehydrogenase the gels were placed for 20 mins in a new 100 mM PP buffer (pH 7.0) and then incubated at 30° C. in the same buffer, to which 0.08% by weight of AND, 0.04% by weight of p-nitroblue-tetrazolium chloride, 0.003% by weight of phenazine methosulphate and 1 mM of the respective substrate had been added, until the corresponding coloured bands appeared.

The transfer of proteins from polyacrylamide gels to PVDF membranes. Proteins were transferred from SDS polyacrylamide gels to PVDF membranes (Waters-Milipore, Bedford, Mass., USA) with the aid of a semidry fast blot device (B32/33 from Biometra, Göttingen, Germany) according to the manufacturer's instructions.

Determination of N-terminal amino acid sequences. The determination of N-terminal amino acid sequences was carried out with the aid of a protein peptide sequencer (of type 477 A, Applied Biosystems, Foster City, USA) and a PTH analyser, according to the manufacturer's instructions.

Isolation and manipulation of DNA. The isolation of genomic DNA was carried out by the method described by Marmur (Marmur, J. 1961. Mol. Biol. 3: 208–218). Megaplasmid DNA was isolated according to the method described by Nies et al. (Nies, D., et al. 1987. J. Bacteriol. 169: 4865–4848). The isolation and analysis of other plasmid DNA or DNA restriction fragments, the packaging of hybrid cosmids in 1-phage particles and the transduction of E. coli. was carried out by standard methods (Sambrook, J. E. F. Fritsch and T. Maniatis. 1989. Molecular cloning: a laboratory manual. 2nd Edition, Cold Spring Harbor Laboratory Press, Cold Spring Harbor, N.Y.).

Transfer of DNA. The preparation and transformation of competent *Escherichia coli* cells was carried out by the method described by Hanahan (Hanahan, D. 1983. J. Mol. Biol. 166: 557–580). Conjugative plasmid transfer between plasmid-containing *Escherichia coli* S17-1 strains (donor) and Pseudomonas sp. strains (recipient) and *Alcaligenes eutrophus* (recipient) was carried out on NB agar plates according to the method described by Friedrich et al. (Friedrich, B. et al. 1981. J. Bacteriol. 147: 198–205) or by a "minicomplementation method" on MM agar plates using 0.5% by weight of gluconate as the carbon source and 25 $\mu g/ml$ of tetracylin or 300 $\mu g/ml$ of kanamycin. In this process cells of the recipient were applied in one direction in the form of an inoculation line. After 5 minutes cells of the donor strains were then applied in the form of inoculation lines crossing the recipient inoculation line. After incubation for 48 h at 30° C. the transconjugants grew directly downstream of the crossing point, whereas neither the donor nor the recipient strain was capable of growth.

Hybridisation experiments. DNA restriction fragments were electrophoretically separated in an 0.8% by weight agarose gel in a 50 mM Tris, 50 mM boric acid and 1.25 mM EDTA buffer (pH 8.5) (Sambrook, J. E. F. Fritsch and T. Maniatis. 1989. Molecular cloning: a laboratory manual. 2nd Edition, Cold Spring Harbor Laboratory Press, Cold Spring Harbor, N.Y.). The transfer of the denatured DNA from the gel to a positively charged nylon membrane (pore size: 0.45 $\mu m$, Pall Filtrationstechnik, Dreieich, Germany), the subsequent hybridisation with biotinylated or $^{32}P$-labelled DNA probes and the production of these DNA probes was carried out according to standard methods (Sambrook, J. E. F. Fritsch and T. Maniatis. 1989. Molecular cloning: a laboratory manual. 2nd Edition, Cold Spring Harbor Laboratory Press, Cold Spring Harbor, N.Y.).

The synthesis of oligonucleotides. Using desoxynucleoside phosphoramidites as the starting material, oligonucleotides were synthesised on a 0.2 $\mu mol$ scale (Beaucage, S. L., and M. H. Caruthers. 1981. Tetrahedron Lett. 22: 1859–1862). The synthesis was carried out in a Gene Assembler Plus according to the manufacturer's instructions (Pharmacia-LKB, Uppsala, Sweden). The elimination of the protecting groups was carried out by incubation for 15 h at 55° C. in a 25 vol.-% aqueous ammonia solution. The oligonucleotides were finally purified in an NAP-5 column (Pharmacia-LKB, Uppsala, Sweden).

DNA sequencing. The determination of nucleotide sequences was carried out by the didesoxy chain termination method described by Sanger et al. (Sanger et al. 1977. Proc. Natl. Acad. Sci. USA 74: 5463–5467) using [$\alpha$-$^{35}S$]dATP and a T7 polymerase sequencing kit (Pharmacia-LKB). 7-Deazaguanosine-5'-triphosphate was used instead of dGTP (Mizusawa, S. et al. 1986. Nucleic Acids Res.14: 1319–1324). The products of the sequencing reactions were separated in a 6% by weight polyacrylamide gel in a 100 mM Tris/HCl, 83 mM boric acid and 1 mM EDTA buffer (pH 8.3) containing 42% by weight urea, an S2 sequencing apparatus (GIBCO/BRL, Bethesda Research Laboratories GmbH, Eggenstein, Germany) being used according to the manufacturer's instructions. After electrophoresis the gels were incubated for 30 mins in 10 vol.-% acetic acid and, after washing briefly in water, dried for 2 hours at 80° C. Kodak X-OMAT AR X-ray films (Eastman Kodak Company, Rochester, N.Y., USA) were used for the autoradiography of the dried gels. In addition DNA sequences were also determined "non-radioactively" with the aid of an "LI-COR DNA Sequencer Model 4000L" (LI-COR Inc., Biotechnology Division, Lincoln, Neb., USA) using a "Thermo Sequenase fluorescent labelled primer cycle sequencing kit with 7-deaza-dGTP" (Amersham Life Science, Amersham International plc, Little Chalfont, Buckinghamshire, England), in each case according to the manufacturer's instructions.

Various sequencing strategies were used: With the aid of synthetic oligonucleotides sequencing was carried out by the "Primer-hopping Strategy" described by Strauss et al. (Strauss, E. C. et al. 1986. Anal. Biochem. 154: 353–360). If only "universal" and "reverse primers" were used hybrid plasmids were used as "template DNA", the inserted DNA fragments of which had been unidirectionally shortened with the aid of an "Exo III/Mung Bean Nuclease Deletion" kit (Stratagene Cloning Systems, La Jolla, Calif., USA) according to the manufacturer's instructions.

Chemicals, biochemicals and enzymes: Restriction enzymes, T4 DNA ligase, lambda DNA and enzymes and substrates for the optical enzymatic tests were obtained from C. F. Boehringer & Söhne (Mannheim, Germany) or from GIBCO/BRL (Eggenstein, Germany). [a-$^{35}$S]dATP and [g-$^{32}$P]ATP were obtained from Amersham/Buchler (Braunschweig, Germany). NA-type agarose was obtained from Pharmacia-LKB (Uppsala, Sweden). All the other chemicals were from Haarmann & Reimer (Holzminden, Germany), E. Merck AG (Darmstadt, Germany), Fluka Chemic (Buchs, Switzerland), Serva Feinbiochemica (Heidelberg, Germany) or Sigma Chemie (Deisenhofen, Germany).

EXAMPLES

Example 1

The isolation of mutants of the Pseudomonas sp. HR 199 strain with defects in the catabolism of eugenol The Pseudomonas sp. HR 199 strain was subjected to nitrosoguanidine mutagenesis in order to isolate mutants with defects in the catabolism of eugenol. The mutants obtained were classified according to their capacity to utilise eugenol, ferulic acid and vanillin as their carbon and energy source. Mutants 6164 and 6165 were no longer capable of utilising eugenol as a carbon and energy source, although, as in the case of the wild type, they were capable of utilising ferulic acid and vanillin. Mutants 6167 and 6202 were no longer capable of utilising eugenol and ferulic acid as their carbon and energy source, although, as in the case of the wild type, they were capable of utilising vanillin. The abovementioned mutants were used in the subsequent molecular-biological analyses.

Example 2

Construction of a Pseudomonas sp. HR 199 gene library in the cosmid vector pVK100

The genomic DNA of the Pseudomonas sp. HR 199 strain was isolated and subjected to partial restriction digestion with EcoRI. The DNA preparation thus obtained was ligated with vector pVK100 cut by EcoRI. The DNA concentrations were relatively high in order to accelerate the formation of concatemeric ligation products. The ligation materials were packaged in 1-phage particles which were subsequently used for transduction of E. coli S17-1. The selection of the transductants was carried out on tetracycline-containing LB agar plates. In this manner 1330 transductants were obtained which contained various hybrid cosmids.

Example 3

The identification of hybrid cosmids containing essential genes of eugenol catabolism The hybrid cosmids of the 1330 transductants were transferred conjugatively to mutants 6164 and 6165 by a mini-complementation process. The resulting transconjugants were examined on MM plates containing eugenol for their capacity to grow again on eugenol (complementation of the respective mutant). Mutant 6164 was complemented by the obtainment of hybrid cosmid pE5-1, which contained a 1.2 kbp, a 1.8 kbp, a 3 kbp, a 5.8 kbp and a 9.4 kbp EcoRI fragment in cloned form. The E. coli S17-1 strain containing this hybrid cosmid was deposited at the "Deutsche Sammlung von Mikroorganismen und Zellkulturen GmbH" (DSM) under the number DSM 10440. Mutant 6165 was complemented by the obtainment of the hybrid cosmids pE207 or pE115 respectively. The complementing capacity was attributed to a 23 kbp EcoRI fragment which was contained in cloned form in the hybrid cosmid pE207 as the only EcoRI fragment, whereas hybrid cosmid pE115 additionally contained a 3 kbp and a 6 kbp EcoRI fragment. The E. coli S17-1 strain containing hybrid cosmid pE207 was deposited at the DSM under the number DSM 10439.

Example 4

The analysis of the 23 kbp EcoRI fragment (E230) of the hybrid cosmid pE207 Fragment E230 was isolated preparatively from EcoRI-digested hybrid cosmid pE207 and ligated to pBluescript SK$^-$-DNA digested with EcoRI. Using the ligation material E. coli XL1-Blue was transformed. Following "blue-white" selection on LB-Tc-Amp agar plates containing X-Gal and IPTG, "white" transformants were obtained whose hybrid plasmids pSKE230 contained the fragment E230 in cloned form. With the aid of this plasmid and by using various restriction enzymes a physical map of the fragment E230 was prepared (FIG. 1).

By cloning subfragments of E230 in vectors pVK101 and pMP92, both of which have a broad host specturm and are also stable in pseudomonads, followed by conjugative transfer into mutant 6165, the region complementing mutant 6165 was localised in a 1.8 kbp KpnI fragment (K18). After cloning this fragment in pBluescript SK$^-$ the nucleotide sequence was determined, the gene of the cytochrome C subunit of eugenol hydroxylase being identified. The gene product of 117 amino acids had an N-terminal leader peptide (MMNVNYKAVGASLLLAFISQGAWA) and 32.9% identity (via a region of 82 amino acids) with the cytochrome C subunit of p-cresol methylhydroxylase produced by Pseudomonas putida (McIntire et al. 1986. Biochemistry 25:5975–5981).

By cloning the KpnI subfragments of E230 adjacent to K18 in pBluescript SK$^-$ and sequencing, additional open reading frames (ORF) were identified, one of which codes for the flavoprotein subunit of eugenol hydroxylase and was highly homologous to the flavoprotein subunit of p-cresol methylhydroxylase produced by Pseudomonas putida. An additional ORF was found to be highly homologous to g-glutamyl cysteine synthetase (the first enzyme in the biosynthesis of glutathione) produced by Escherichia coli (Watanabe et al. 1986. Nucleic Acids Res. 14: 4393–4400).

In the soluble fraction of the crude extract of E. coli (pSKE230) vanillin dehydrogenase was detected by specific activity staining in a polyacrylamide gel. By subcloning in pBluescript SK_ and analysis of soluble fractions of the crude extracts of the transformants obtained, the vanillin dehydrogenase gene (vdh) was localised in a 3.8 kbp HindIII/EcoRI subfragment of E230. The complete nucleotide sequence of this fragment was determined. The molecular weight of the vanillin dehydrogenase was 50,779, as confirmed by SDS polyacrylamide gel electrophoresis. The amino acid sequence was highly homologous to other aldehyde dehydrogenases of various origins.

Upstream of the vdh gene an additional ORF was identified which was homologous to enoyl-CoA hydratases. The calculated molecular weight of 27,297 was confirmed by SDS polyacrylamide gel electrophoresis.

By sequencing the 5.0 kbp HindIII subfragment of E230, which had also been cloned in pBluescript SK$^-$, an ORF was identified which was highly homologous to the lignostilbene-a,b-dioxygenase produced by *Pseudomonas paucimobilis*. By complete sequencing of the fragment E230 two additional ORF's were identified which were homologous to formaldehyde-dehydrogenases (fdh) and alcohol dehydrogenases (adh) (cf. FIG. 1).

Example 5

The analysis of the region of hybrid cosmid pE5-1 complementing mutant 6164

Mutant 6164 was complemented by the obtainment of hybrid cosmid pE5-1 which contained a 1.2 kbp (E12), a 1.8 kbp (E18), a 3 kbp (E30), a 5.8 kbp (E58) and a 9.4 kbp (E94) EcoRI fragment in cloned form (FIG. 1). By digesting pE5-1 with EcoRI and subsequent religation a derivative (pE106) of this hybrid cosmid was obtained which only contained fragments E12, E18 and E30. Following conjugative transfer into mutant 6164 this plasmid was however capable of complementing the latter, as a result of which corresponding transconjugants were once again capable of growing on eugenol as a carbon and energy source.

After digesting plasmid pE106 with EcoRI, gel-electrophoretic separation of the digestion material in a 0.8% by weight agarose gel and transfer of the DNA to a nylon membrane, hybridisation was carried out with a $^{32}$P-labelled oligonucleotide probe of the following sequence:

```
                        SEQ ID NO: 43
ATG CAA CTC ACC AAC AAA AAA ATC GT-3'
     G   G   C   T   G   G   T

G   G   C       G   G

G   T   G   G       G

G       G   G

T       G   G
```

The sequence of this gene probe had been deduced from the N-terminal amino acid sequence of coniferyl alcohol dehydrogenase (CADH) (see below) purified from Pseudomonas sp. HR 199. With the aid of this probe the region of the cadh gene encoding the N-terminus of the CADH was localised in fragment E12. This fragment and parts of the adjacent fragment E 18 were also sequenced and the complete sequence of the cadh gene thus determined. The amino acid sequence deduced from cadh was homologous to other alcohol dehydrogenases of class I, group II (according to Matthew and Fewson. 1994. Critical Rev. Microbiol. 20(1): 13–56).

Example 6

Purification and Characterisation of Coniferyl Alcohol Dehydrogenase Pseudomonas sp. HR 199 was grown on eugenol. The cells were harvested, washed and disrupted with the aid of a French press. The soluble fraction of the crude extract obtained after ultracentrifugation had a specific activity of 0.24 U/mg of protein. By means of chromatography on DEAE Sephacel an 11.7-fold enrichment of CADH was obtained in a yield of 83.7%. By means of chromatography on Sephadex G200 a 6.8-fold enrichment of CADH was obtained in a yield of 11.2%. By means of chromatography on butyl Sepharose 4B a 70.6-fold enrichment of CADH was obtained in a yield of 7.8%.

With the aid of this method a preparation was obtained which displayed a band at 27 kDa according to SDS polyacrylamide gel electrophoresis. The purification factor was 64 and the yield 0.8%.

Optimum Temperature and Thermal Stability

The optimum temperature for the reaction catalysed with CADH was 42° C. The enzyme was however sensitive to heat. The half-lives were as follows: $T_{1/2}$ (34° C.)=5 mins, $T_{1/2}$ (39° C.)=1 min, $T_{1/2}$ (42° C.)<1 min.

Optimum pH

The optimum pH for the reaction catalysed by CADH was 10.9 in a 25 mM MOPS buffer. At higher pH values a decrease in activity due to denaturation was observed.

Apparent Molecular Weight

The molecular weight of native CADH was determined with the aid of FPLC by gel filtration on Superdex 200HR 10/30 at 54.9 kDa, which suggests a $a_2$ subunit structure.

N-terminal Amino Acid Sequence

The determination of the N-terminal amino acid sequence of the purified protein revealed the following result:

```
                                                SEQ ID NO: 45
    1         5         10        15        20
M Q L T N K K I V V V (G) V (S) ? (R) (I) ? (A) (E)
                         (V)     (V)
```

(Sequence in the single letter code; ?: definition not possible; ( ): not certain; in the second row an amino acid is mentioned which may also apply)

Example 7

Purification and Characterisation of Coniferylaldehyde Dehydrogenase

Pseudomonas sp. HR 199 was grown on eugenol. The cells were harvested, washed and disrupted with the aid of a French press. The soluble fraction of the crude extract obtained after ultracentrifugation displayed a specific activity of 0.43 U/mg protein. By chromatography on DEAE Sephacel a 6.6-fold enrichment of CALDH was obtained in a yield of 65.3%. By chromatography on hydroxy-apatite a 63-fold enrichment of CALDH was obtained in a yield of 33%. By chromatography on Superdex HR 200 an 81-fold enrichment of CALDH was obtained in a yield of 13%. With the aid of this method a preparation was obtained which, according to SDS polyacryamide gel electrophoresis, displayed a band at approx. 49 kDa.

Optimum Temperature and Thermal Stability

The optimum temperature of the reaction catalysed by CALDH was 26° C. The enzyme was sensitive to heat. The half-lives were as follows: $T_{1/2}$ (31° C.)=5 mins, $T_{1/2}$ (34° C.) =2.5 mins, $T_{1/2}$ (38° C.)=1 min.

Optimum pH

The optimum pH for the reaction catalysed by CALDH was 8.8 in a 100 mM Tris/HCl buffer. At this pH value the enzyme is however already unstable (87% decrease in activity within 5 mins). At lower pH values the enzyme is more stable (e.g. pH 6.0: 50% decrease in activity within 4 hours).

Substrate Specificity

The enzyme not only accepts coniferylaldehyde (100%) but also transcinnamaldehyde (96.7%), sinapyl aldehyde (76.7%), p-anisaldehyde (23.1%), benzaldehyde (17.8%), 3,5-dimethoxy-benzaldehyde (7.6%) and 3-hydroxy-benzaldehyde (1.7%) as substrates.

The $K_M$ value of CALDH for coniferylaldehyde is in the range between 0.007 and 0.012 mM at a $V_{max}$ of approx. 9 to 15 U/ml. The $K_M$ value of CALDH for AND is 0.334 mM at a $V_{max}$ of 14.2 U/ml. Compared with AND, NADP is accepted at a rate of 4.3%.

N-terminal Amino Acid Sequence

The determination of the N-terminal amino acid sequence of the purified protein revealed the following result:

SILGLNGAPVGAEQLGSAL (D) 20 SEQ ID NO:45

(seqence in the one-letter code; ( ): not certain).

Example 8

Localisation and sequencing of the coniferylaldehyde dehydrogenase gene (caldh)

The N-terminal amino acid sequence was definitively assigned to an amino acid sequence deduced from the DNA sequence of fragment E94 of plasmid pE5-1. Thus the CALDH structural gene caldh is localised in E94. The amino acid sequence deduced from caldh was homologous to other aldehyde dehydrogenases.

Example 9

The complementation of other mutants displaying defects in the catabolism of eugenol using hybrid cosmids pE207 and pE5-1

Following NMG mutagenesis, mutants 6167 and 6202 had been obtained which were no longer capable of utilising eugenol and ferulic acid as their carbon and energy source (see above). The obtainment of plasmid pE207 meant that, after conjugative transfer, mutant 6202 was once again capable of utilising the aforementioned substrates. This mutant is complemented by the gene homologous to enoyl-CoA hydratase.

The obtainment of plasmid pE5-1 meant that, after conjugative transfer, mutant 6167 was once again capable of utilising the abovementioned substrates. By individually cloning the EcoRI fragments of pE5-1 in pHP 1014 and the conjugative transfer of these plasmids into mutant 6167 the complementing property was localised in fragment E94. A physical map of fragment E94 was prepared after cloning in pBluescript SK- and digestion with various restriction enzymes. By cloning subfragments of E94 in the vectors pVK101 and pMP92, followed by conjugative transfer into mutant 6167, the region complementing mutant 6167 was localised in a 1.9 kbp EcoRI/HindIII fragment (EH19). After cloning this fragment in pBluescript SK⁻ and sequencing, 2 ORF's were identified which were homologous to acetyl-CoA acetyltransferases and to "medium-chain acyl-CoA synthetase" produced by *Pseudomonas oleovorans*. By com-pletely sequencing fragment E94, additional ORF's were identified which were homologous to regulator proteins and a chemotaxis protein (cf. FIG. 1).

Example 10

Determination of the chromosomal coding of the genes for the catabolism of eugenol in Pseudomonas sp. HR 199

Since Pseudomonas sp. HR 199 has a megaplasmid of a size of approx. 350 kbp, a hybridisation experiment was carried out to examine whether the genes for the catabolism of eugenol were localised in this megaplasmid or in the chromosome. For this purpose megaplasmid preparations of the wild type and of the mutants were separated in an 0.8% by weight agarose gel. The chromosomal and megaplasmid DNA was blotted onto a nylon membrane and then hybridised against a biotinylated HE38 DNA probe. A hybridisation signal was only obtained with the chromosomal DNA and not with the megaplasmid DNA. Thus the genes for the catabolism of eugenol in Pseudomonas sp. HR 199 are coded in the chromosome.

Example 11

The heterologous expression of genes for the catabolism of eugenol from Pseudomonas sp. HR 199 in other Pseudomonas strains and in *Alcaligenes eutrophus*.

The plasmid pE207 and a pVK101 hybrid plasmid containing fragment H110 (pVKH110) were conjugatively transferred to *A. eutrophus* and into Pseudomonas strains which were not capable of metabolising eugenol, vanillin or vanillic acid. The transconjugants obtained were not only examined for their capacity to grow on MM agar plates containing eugenol, vanillin or vanillic acid but also some transconjugants were incubated with eugenol in an MM liquid medium. By means of HPLC analysis of the culture supernatants some of the transconjugants were found to metabolise eugenol.

In this analysis the functional expression of the vdh gene in transconjugants of *P. stutzeri, P. asplenii*, Pseudomonas sp. DSM13, Pseudomonas sp. DSM15a and Pseudomonas sp. D1 was determined.

Transconjugants of the strain Pseudomonas sp. D1, which contained the plasmid pE207, were capable of growing using eugenol as their carbon and energy source.

In corresponding transconjugants of *P. testosteroni* LMD3324, *P. fluorescens* TypeB, *P. stutzeri* DSM 50027, Pseudomonas sp. DSM 1455 and *P. fragi* DSM3456 functional expression of the eugenol hydroxylase genes was also observed which resulted in the secretion of intermediates of the catabolism of eugenol (coniferyl alcohol, coniferylaldehyde, ferulic acid, vanillin, vanillic acid) into the culture medium. Growth of these transconjugants on eugenol was however not observed.

What is claimed is:

1. An isolated eugenol hydroxylase comprising two subunits wherein one subunit comprises a cytochrome C which is encoded by SEQ ID NO: 11 and wherein the second subunit comprises a flavoprotein which is encoded by SEQ ID NO: 15.

2. An isolated DNA coding for the enzyme according to claim 1 comprising SEQ ID NO: 11.

3. A cosmid clone comprising an isolated DNA according to claim 2.

4. A vector comprising an isolated DNA according to claim 2.

5. A microorganism transformed with the isolated DNA according to claim 2.

6. A process of converting eugenol to coniferyl alcohol comprising subjecting eugenol to the eugenol hydroxylase according to claim 1 for a period of time sufficient to convert the eugenol to coniferyl alcohol and recovering the alcohol thus formed.

7. An isolated DNA coding for the enzyme according to claim 1 comprising SEQ ID NO: 15.

* * * * *